US010849345B2

(12) United States Patent
Tanner et al.

(10) Patent No.: US 10,849,345 B2
(45) Date of Patent: Dec. 1, 2020

(54) BARLEY WITH VERY LOW LEVELS OF HORDEINS

(71) Applicants: COMMONWEALTH SCIENTIFIC AND INDUSTRIAL RESEARCH ORGANISATION, Campbell (AU); GRAINS RESEARCH AND DEVELOPMENT CORPORATION, Barton (AU)

(72) Inventors: Gregory John Tanner, Elwood (AU); Crispin Alexander Howitt, Evatt (AU); Michelle Lisa Colgrave, Everton Hills (AU); Malcolm James Blundell, Gordon (AU)

(73) Assignees: COMMONWEALTH SCIENTIFIC AND INDUSTRIAL RESEARCH ORGANISATION, Acton (AU); GRAINS RESEARCH AND DEVELOPMENT CORPORATION, Barton (AU)

( * ) Notice: Subject to any disclaimer, the term of this patent is extended or adjusted under 35 U.S.C. 154(b) by 411 days.

(21) Appl. No.: 14/897,616

(22) PCT Filed: Jun. 13, 2014

(86) PCT No.: PCT/AU2014/000619
§ 371 (c)(1),
(2) Date: Dec. 10, 2015

(87) PCT Pub. No.: WO2014/197943
PCT Pub. Date: Dec. 18, 2014

(65) Prior Publication Data
US 2016/0128345 A1 May 12, 2016

(30) Foreign Application Priority Data

Jun. 13, 2013 (AU) ................................ 2013902140
Jul. 11, 2013 (AU) ................................ 2013902565

(51) Int. Cl.
A23L 7/10 (2016.01)
A23L 11/20 (2016.01)
A23L 7/20 (2016.01)
A01H 6/46 (2018.01)

(52) U.S. Cl.
CPC ................. *A23L 7/198* (2016.08); *A23L 7/10* (2016.08); *A23L 7/20* (2016.08); *A23L 11/20* (2016.08)

(58) Field of Classification Search
None
See application file for complete search history.

(56) References Cited

U.S. PATENT DOCUMENTS 4,945,050 A 7/1990 Sanford et al.
5,004,863 A 4/1991 Umbeck et al.
5,104,310 A 4/1992 Saltin et al.
5,141,131 A 8/1992 Miller et al.
5,159,135 A 10/1992 Umbeck et al.
5,177,010 A 1/1993 Goldman et al.
5,362,865 A 11/1994 Austin et al.
5,384,253 A 1/1995 Krzyzek et al.
5,416,011 A 5/1995 Hinchee et al.
5,451,513 A 9/1995 Maliga et al.
5,463,174 A 10/1995 Moloney et al.
5,472,869 A 12/1995 Krzyzek et al.
5,518,908 A 5/1996 Corbin et al.
5,545,818 A 8/1996 McBride et al.
5,569,834 A 10/1996 Hinchee et al.
5,589,617 A 12/1996 Nehra et al.
5,859,347 A 1/1999 Brown et al.
5,877,402 A 3/1999 Maliga et al.
5,932,479 A 8/1999 Daniell et al.
6,100,447 A 8/2000 Wu et al.
6,541,257 B2 4/2003 Lemaux et al.
7,074,986 B1 7/2006 Hirota et al.
7,652,202 B2 1/2010 Clark et al.
8,642,846 B2 2/2014 Tanner et al.
9,133,427 B2 9/2015 Tanner et al.
2011/0017072 A1 1/2011 Frigeri
2011/0135784 A1* 6/2011 Tanner .................... A01H 5/10
426/2
2012/0034339 A1 2/2012 Guiliani et al.
2016/0130539 A1 5/2016 Tanner et al.

FOREIGN PATENT DOCUMENTS

AU 667939 4/1996
CA 2092588 9/1994
EP 0465572 6/1995
EP 1 210 869 6/2002

(Continued)

OTHER PUBLICATIONS

Ohlund et al, 2010, J Hum Nutr Diet, 23: 294-300.*
Howard et al, 1996, J. Cereal Sci., 24:47-53.*
USDA Deposit information for RISO Mutant 56, accession No. PI384986.
USDA Deposit information for RISO Mutant 1508, accession No. PI384988.
Supplementary European Search Report and Search Opinion dated Dec. 9, 2010 in connection with European Patent Application No. 08782920.6.
Response to Search Opinion filed on Jul. 6, 2011 in connection with European Patent Application No. 08782920.6.
European Examination Report dated Dec. 15, 2011 in connection with European Patent Application No. 08782920.6.

(Continued)

*Primary Examiner* — Jason Deveau Rosen
(74) *Attorney, Agent, or Firm* — John P. White; Gary J. Gershik

(57) ABSTRACT

The present invention relates to methods of producing a food or malt-based beverage suitable for consumption by a subject with Coeliac's disease. In particular, the present invention relates to methods of producing a food or malt-based beverage with very low levels of hordeins. Also provided are barley plants which produce grain that can be used in the methods of the invention.

18 Claims, 14 Drawing Sheets

Figure 1:
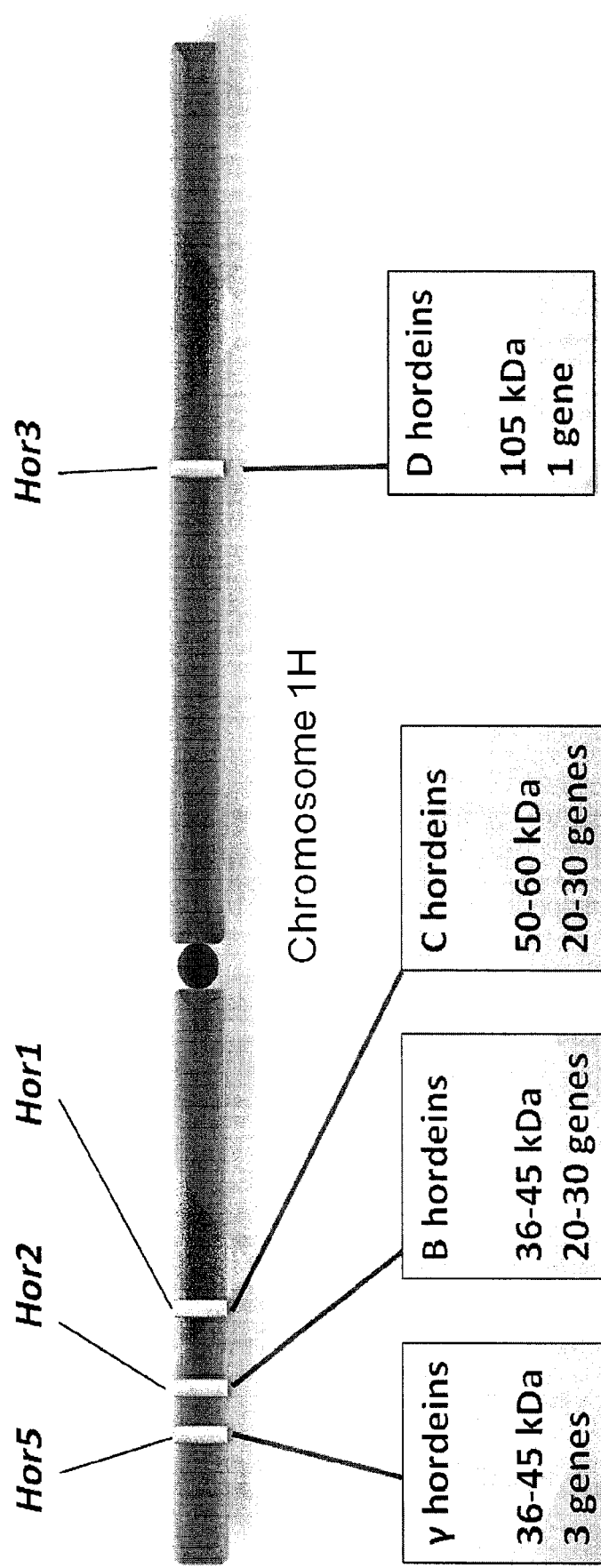

Specification includes a Sequence Listing.

(56) References Cited

FOREIGN PATENT DOCUMENTS

| WO | WO 84/02913 | 8/1984 |
|---|---|---|
| WO | WO 87/06614 | 11/1987 |
| WO | WO 92/09696 | 6/1992 |
| WO | WO 93/21335 | 10/1993 |
| WO | WO 94/019930 | 9/1994 |
| WO | WO 97/20936 | 6/1997 |
| WO | WO 97/048814 | 12/1997 |
| WO | WO 99/05265 | 2/1999 |
| WO | WO 99/14314 | 3/1999 |
| WO | WO 99/32619 | 6/1999 |
| WO | WO 99/49029 | 9/1999 |
| WO | WO 99/53050 | 10/1999 |
| WO | WO 2000/058453 | 10/2000 |
| WO | WO 01/34815 | 5/2001 |
| WO | WO 2005/021765 | 3/2005 |
| WO | WO 2005/027953 | 3/2005 |
| WO | WO 2006/051093 | 5/2006 |
| WO | WO 2009/021285 | 2/2009 |
| WO | WO 2013/063653 | 1/2013 |
| WO | WO 2014/197943 | 12/2014 |

OTHER PUBLICATIONS

Response filed to the Examination Report filed on Jun. 25, 2012 in connection with European Patent Application No. 08782920.6.
Jun. 6, 2013 Summons to Attend Oral Proceedings, issued in connection with European Patent Application No. 08782920.6.
Oct. 24, 2013 Result of Consultation in connection with European Patent Application No. EP 08 782 920.6.
New Zealand Examination Report dated Nov. 24, 2010 in connection with New Zealand Patent Application No. 583466.
Response filed to New Zealand Examination Report filed on May 16, 2012 in connection with New Zealand Patent Application No. 583466.
Second New Zealand Examination Report dated Jun. 1, 2012 in connection with New Zealand Patent Application No. 583466.
Response filed to New Zealand Examination Report filed on Aug. 13, 2012 in connection with New Zealand Patent Application No. 583466.
Australian Examination Report dated Jun. 7, 2010 in connection with Australian Patent Application No. 2008286698.
Feb. 25, 2013 Response filed in connection with Australian Patent Application No. 2008286698.
Apr. 30, 2013, Examination Report, issued in connection with Australian Patent Application No. 2008286698.
Jul. 5, 2013 Response, filed in connection with Australian Patent Application No. 2008286698.
English Language Translation of Chinese Office Action dated Jan. 30, 2012 in connection with Chinese Patent Application No. 200880111180.3.
Response filed to Chinese Office Action filed on Jun. 14, 2012 in connection with Chinese Patent Application No. 200880111180.3, with English Language Filed Claims.
Second Chinese Office Action dated Dec. 11, 2012 in connection with Chinese Patent Application No. 200880111180.3, including English Language Translation.
Russian Office Action dated Jun. 6, 2011 in connection with Russian Patent Application No. 2010109421, including English Language Translation.
Response filed to Russian Office Action filed in connection with Russian Patent Application No. 2010109421, with English Language Claims.
Second Russian Office Action dated May 21, 2012 in connection with Russian Patent Application No. 2010109421, including English Language Translation.
Response filed to Second Russian Office Action filed in connection with Russian Patent Application No. 2010109421, with English Language Claims.
Third Russian Office Action dated Aug. 22, 2012 in connection with Russian Patent Application No. 2010109421.
Third Russian Office Action dated Aug. 22, 2012 in connection with Russian Patent Application No. 2010109421, including English Language Translation.
Apr. 22, 2013 Office Action, issued in connection with Russian Patent Application No. 2010109421, including English Language translation.
Ukrainian Office Action dated Jun. 13, 2012 in connection with Ukrainian Patent Application No. 2010 02764.
Response filed to Ukrainian Office Action filed on Aug. 30, 2012 in connection with Ukrainian Patent Application No. 2010 02764.
Ukrainian Office Action dated Jun. 13, 2012 in connection with Ukrainian Patent Application No. 2010 02764, including English Language Translation.
International Search Report issued by the International Searching Authority (ISA/AU) dated May 8, 2009 in connection with International Application No. PCT/AU2008/001172.
Feb. 16, 2010 International Preliminary Report on Patentability, issued in connection with PCT International Patent Application No. PCT/AU2008/001172.
European Patent Application No. EP 1,210,869 A1, published Jun. 5, 2002 (Sapporo Breweries LTD.).
Mar. 13, 2013 Response filed in connection with Chinese Patent Application No. 20080111180.3.
Jul. 30, 2012 Office Action, issued in connection with U.S. Appl. No. 12/733,139.
Aug. 30, 2013 Response, filed in connection with U.S. Appl. No. 12/733,139.
Sep. 4, 2012 Office Communication, issued in connection with U.S. Appl. No. 12/733,139.
Sep. 5, 2012 Response, filed in connection with U.S. Appl. No. 12/733,139.
Nov. 5, 2012 Office Action, issued in connection with U.S. Appl. No. 12/733,139.
Feb. 5, 2013 Response, filed in connection with U.S. Appl. No. 12/733,139.
Apr. 9, 2013 Final Office Action, issued in connection with U.S. Appl. No. 12/733,139.
Jul. 5, 2013 Response, filed in connection with U.S. Appl. No. 12/733,139.
Sep. 20, 2013 Notice of Allowance and Summary of Examiner Interview, issued in connection with U.S. Appl. No. 12/733,139.
Jan. 30, 2014 Response, filed in connection with Japanese Patent Application No. 2010-520-382.
Mar. 25, 2014 First Office Action, issued in connection with Mexican Patent Application No. MX/a/2010/01734.
Jun. 4, 2014 Response, filed in connection with Mexican Patent Application No. MX/a/2010/01734.
English Language Translation of Aug. 6, 2014 Office Action, issued in connection with Japanese Patent Application No. 2010-520382.
Dec. 11, 2014 Response, filed in connection with Japanese Patent Application No. 2010-520382, including English Language amended claims; Apr. 20, 2015 Decision of Rejection, issued in connection with Japanese Patent Application No. 2010-520382.
Apr. 20, 2015 Decision to Dismiss the Amendments, issued in connection with Japanese Patent Application No. 2010-520382.
Sep. 18, 2014 Office Action, issued in connection with Canadian Patent Application No. 2,696,250.
Mar. 18, 2015 Response, filed in connection with Canadian Patent Application No. 2,696,250.
Sep. 11, 2014 Search Report, issued in connection with PCT International Patent Application No. PCT/AU2014/000619, filed Jun. 13, 2014.
Sep. 11, 2014 Written Opinion, issued in connection with PCT International Patent Application No. PCT/AU2014/000619, filed Jun. 13, 2014.
Aug. 10, 2015 First Examination Report, issued in connection with Australian Patent Application No. 2013280204.
Notification on the result of preliminary examination that issued for corresponding Vietnamese patent application 1-2016-00155.

(56) References Cited

OTHER PUBLICATIONS

Aastrup S. (1983) "Selection and Characterization of Low Beta Glucan Mutants from Barley" Carlsberg Research Communications, vol. 48, No. 4, pp. 307-316.
Abdullah et al. (1986) "Efficient Plant Regeneration from Fice Protoplasts Through Somatic Embryogenesis" Biotechnology 4:1087.
Allred et al. (2014) "Evaluation of Qualitative and Quantitative Immunoassays to Detect Barley Contamination in Gluten-Free Beer with Confirmation Using LC/MS/MS" Journal of AOAC International 97(6): 1615.
Almeida and Allshire (2005) "RNA silencing and genome regulation" TRENDS Cell Biol 15: 251-258.
Anderson et al. (2000) "In vivo antigen challenge in coeliac disease identifies a single transglutaminase-modified peptide as the dominant A-gliadin T-cell epitope" Nature Medicine 6: 337-342.
Anderson et al. (2005) "T cells in peripheral blood after gluten challenge in coeliac disease" Gut 54:1217-1223.
Aventz-Hansen (2000) "The Intestinal T Cell Response to a-Gliadin in Adult Coeliac Disease Is Focused on a Single Deamidated Glutamine Targeted by Tissue Transglutaminase" Journal of Experimental Medicine 191: 603-612.
Biagi et el. (2004) "A Milligram of Gluten a Day Keeps the Mucosal Recovery Away: A Case Report" Nutrition Reviews 62:360-363.
Bourque (1995) "Antisense strategies for genetic manipulations in plants" Plant Sci. 105: 125-149.
Bradford (1976) "A Rapid and Sensitive Method for the Quantitation of Microgram Quantities of Protein Utilizing the Principle of Protein-Dye Binding" Analytical Chemistry 72: 248-254.
Brandt et al. (1990) "A plant serpin gene Structure, organization and expression of the gene encoding barley protein $Z_4$" Eur J Biochem 194:499-505.
Campbell et al. (2001) "Identification of a juvenile hormone esterase gene by matching its peptide mass fingerprint with a sequence from the *Drosophila* genome project" Insect Biochemistry and Molecular Biology 31: 513-520.
Capecchi (1980) "High Efficiency Transformation by Direct Microinjection of DNA into Cultured Mammalian Cells" Cell 22:479-488.
Catassi et al. (2007) "A prospective, double-blind, placebo-controlled trial to establish a safe gluten threshold for patients with coeliac disease" Am. J. Clin. Nutr. 85:160-166.
Cheng et al. (1996) "Production of fertile transgenic peanut (*Arachis hypogaea* L.) plants using Agrobacterium tumefaciens" Plant Cell Rep. 15:653-657.
Clapp (1993) "The 16-Kilodalton N-Terminal Fragment of Human Prolactin Is a Potent Inhibitor of Angiogenesis" Clin. Perinatol. 20:155-168.
Collin et al. (2004) "The safe threshold for gluten contamination in gluten-free products. Can trace amounts be accepted in the treatment of coeliac disease?" Aliment Pharmacol Ther 19:1277-1283.
Comai et al. (2004) "Efficient discovery of DNA polymorphisms in natural populations by Ecotilling" Plant J 37: 778-786.
Dailey et al (1988) "Hordein Gene Expression in a Low Protein Barley Cultivar" Plant Physiol 88:450-453.
Davies et al. (1993) "Spatial and Temporal Patterns of B Hordein Synthesis in Developing Barley (*Hordeum vulgare* L.) Caryopses" Cell Biology International Reports 17:195-202.
De Angelis et al., (2007) "Probiotic Preparation Has the Capacity To Hydrolyze Proteins Responsible for Wheat Allergy" Journal of Food Protection, vol. 70, No. 1, pp. 135-144.
(1980) "A nearly non-functional mutant allele of the storage protein locus Hor2 in barley" Hereditas 93:217-222.
Doll (1983) Barley seed proteins and possibilities for their improvement. In "Seed Proteins: Biochemistry, Genetics, Nutritional Value", Gottschalk W, Muller HP (eds). Martinus Nijhoff, The Hague:207-223.
Doll and Oram (1989) "Deviating Mendelian segregation of barley gene lys 3a" Hereditas 110:97-99.
Doll et al (1973) "Hans Doll: Inheritance of the high-lysine character of a barley mutant" Barley Genetics Newsletter 3:12-13.
Doll et al. (1980) "A nearly non.functional mutant allele of the storage protein locus Hor2 in barley" Hereditas 93: 217-222.
Dostalek et al. (2006) "Immunochemical determination of gluten in malts and beers" Food Additives and Contaminants 23:1074-1078.
Douliez et al. (2000) "Structure, Biological and Technological Functions of Lipid Transfer Proteins and Indolines, the Major Lipid Binding Proteins from Cereal Kernels" J Cereal Sci 32:1-20.
Ellis et al. (1990) "Detection and estimation of the barley prolamin content of beer and malt to assess their suitability for patients with coeliac disease" Clin Chim Acta 189: 123-130.
Evans et al (2002) "Don't Be Fobbed Off: The Substance of Beer Foam—A Review" J. Am. Soc. Brew. Chem. 61:55-62.
Fasano et al. (2003) "Prevalence of Coeliac Disease in At-Risk and Not-At-Risk Groups in the United States" Archives of Internal Medicine 163: 286-292.
Field et al. (1982) "The Purification and Characterization of Homologous High Molecular Weight Storage Proteins from Grain of Wheat, Rye and Barley" Theoretical and Applied Genetics 62:329-336.
Folich et al. (1957) "A Simple Method for the Isolation and Purification of Total Lipides from Animal Tissues" J Biol Chem. 226:497-509.
Garcia-Casado et al. (2001) "Isolation and characterization of barley lipid transfer protein and protein Z as beer allergens" J. Allergy Clin. Immunol. 108:647-9.
Gellrich et al. (2003) "Biochemical Characterization and Quantification of the Storage Protein (Secalin) Types in Rye Flour" Cereal Chem. 80(1):102-109.
Graham et al. (1973) "Transformation of Rat Cells by DNA of Human Adenovirus" Virology 54:536-539.
Grant et al. (1995) "Transformation of peas (*Pisum sativum* L.) using immature cotyledons" Plant Cell Rep. 15:254-258.
Green et al., (1997) "Grain Development Mutants of Barley" Plant Physiol. 114:203-212.
Hadjivassiliou et al. (2004) "The immunology of gluten sensitivity: beyond the gut" Trends Immunol 25:578-82.
Haseloff and Gerlach (1988) "Simple RNA enzymes with new and highly specific endoribonuclease activities" Nature 334:585-591.
Hejgaard et al. (1985) "Sequence homology between barley endosperm protein Z and protease inhibitors of the $a_1$-antitrypsin family" FEBS 180:89-94.
Hejaard and Boisen (1980) "High-lysine proteins in Hiproly barley breeding: Identification, nutritional significance and new screening methods" Hereditas 93: 311-320.
Henikoff et al. (2004) "Tilling. Traditional Mutagenesis Meets Functional Genomics" Plant Physiol 135: 630-636.
Hogberg et al. (2004) "Oats to children withi newly diagnosed coeliac disease: a randomized double blind study" Gut 53: 649-654.
Howard et al. (1996) The Relationship Between D Hordein and Malting Quality in Barley. Journal of Cereal Science, 24:47-53.
Ingerversen et al. (1973) "Induced Seed Protein Mutant of Barley" Experientia 29:1151-1152.
Jaradat (1991) "Grain protein variability among populations of wild barley (*Hordeum spontaneum* C. Koch.) from Jordan" Theor Appl Genet 83:164-168.
Kanerva et al. (2005) "Determination of Prolamins in Beers by ELISA and SDS-PAGE" J Instit Brewing 111: 61-64.
Kapp and Bamforth (2002) "The foaming properties of proteins isolated from barley" J. Sic. Food Agric. 82:1276-1281.
Karlsson (1977) "Linkage studies in a gene for high lysine content in Riso barley mutant 1508." Barley Genetics Newsletter, vol. 7, II. Research Notes.
Kasarda et al. (1984) "Nucleic acid (cDNA) and amino acid sequences of a-type gliadins from wheat (*Triticum aestivum*)" PNAS 81:4712-4716.
Kim et al. (2004) "Structural basis for HLA-DQ2-mediated presentation of gluten epitopes in celiac disease" Proc Natl Acad Sci USA 101:4175-9.
Klemsdal (1987) "The barley high lysine genes of mutants 1508 and 527 alter hordein polypeptide composition quantitatively, but not qualitatively" Hereditas 107: 107-114.
Koziel et al. (1996) "Optimizing expression of transgenes with an emphasis on post-transcriptional events" Plant Mol. Biol. 32:393-405.

(56) References Cited

OTHER PUBLICATIONS

Kreis and Doll (1980) "Starch and prolamin level in single and double high-lysine barley mutants" Physiol. Plant 48:139-143.
Kreis and Shewry (1989) "Unusual Features of Cereal Seed Protein Structure and Evolution" BioEssays 10:201-207.
Kreis et al. (1983) "Molecular Analysis of a Mutation conferring the High-Lysine Phenotype on the Grain of Barley (Hordeum vulgare)" Cell 34:161-177.
Kreis et al. (1984) "Molecular Analysis of the Effects of the lys 3a Gene on the Expression of Hor Loci in Developing Endosperms of Barley (Hordeum vulgare L.)" Biochem. Genetics 22: 231-255.
Kucharska et al., (1998) "Estimation of induced mutation rates for four esterase genes in barley (Hordeum vulgare L.)" J. Appl. Genet. 39(2):141-145.
Laitilan Wirvoitusjuomatehdas: "Laitilan Kukko-oluet sopivat myös keliakiaakikoille", Sep. 6, 2005, retrieved from: www.deski.fi/page.php?page_id=9&tiedote_id=1017, including English Language Translation.
Laitilan Wirvoitusjuomatehdas: "Laitilan Kukko-Oluet Sopivat Myös Keliaakikoille" (retrieved Sep. 18, 2014) URL: deski.fi/page.php?page_id=9&tiedote_id=1017, published Jan. 22, 2012 as per Wayback Machine, including English Language.
Lewis (2005) "Celiac Disease, Beer, and Brewing" TIBBA TQ 42:45-48.
Lombardia et al. (2007) "A Competitive R5-ELISA For Measurements of Hydrolyzed Barley and Wheat Prolamins: Analysis of Beer" Proceedings of the EBC Congress—CD-ROM Edition; 31; 146; European Brewery Convention.
Lu et al. (1993) "High Efficiency Retroviral Mediated Gene Transduction into Single Isolated Immature and Replatable $CD34^{3+}$ Hematopoietic Stem/Progenitor Cells from Human Umbilical Cord Blood" J. Exp. Med. 178:2089-2096.
Lundin et al. (2003) "Oats induced villous atrophy in coeliac disease" Gut 52: 1649-1652.
Marti et al. (2005) "Prolyl Endopeptidase-Mediated Destruction of T Cell Epitopes in Whole Gluten: Chemical and Immunological Characterization" J Pharmacal Exp Therapeut 312:19-26.
Mena et al. (1998) "An endosperm-specific DOF protein from barley, highly conserved in wheat, binds to and activates transcription from the prolamin-box of native B-hordien promoter in barley endosperm" Plant J. 16:53-62.
Millar and Waterhouse (2005) "Plant and animal microRNAs: similarities and differences" Funct Integr Genomics 5:129-135.
Mullins et al. (1999) "Isolation of mutants exhibiting altered resistance to Sclerotinia sclerotiorum from small M2 populations of an oilseed rape (Brassica napus) variety" Eur J Plant Pathol 105:465-475.
Munck et al. (1970) "Gene for Improved Nutritional Value in Barley Seed Protein" Science 168:985-987.
Olsen (1977) "Diallel analysis of high lysine barley, Hordeurn vulgare L." Hereditas 87: 11-20.
Onishi et al. (1999) "Monoclonal Antibody Probe for Assessing Beer Foam Stabilizing Proteins" J. Agric. Food Chem. 47:3044-3049.
Pasquinelli et al. (2005) "MicroRNAs: a developing story" Curr Opin Genet Develop 15: 200-205.
Peraaho et al. (2004a) "Oats Can Diversify a Gluten-Free Diet in Celiac Disease and Dermatitis Herpetiformis" Journal of the American Dietetic Association 104: 1148-1150.
Peraaho et al. (2004b) "Effect of an Oats-Containing Gluten-free Diet on Symptoms and Quality of Life in Coeliac Disease. A Randomized Study" Scandinavian Journal of Gastroenterology 39: 27-31.
Perriman et al. (1992) "Extended target-site specificity for a hammerhead ribozyme" Gene 113: 157-163.
Perrocheau et al (2005) "Probing heat-stable water-soluble proteins from barley to malt and beer" Proteomics 5:2849-2858.
Peters et al. (2003) "Causes of Death in Patients With Celiac Disease in a Population-Based Swedish Cohort" Arch Intern Med 163-1566-1572.

Pynnonen et al. (2004) "Mental Disorders in Adolescents With Celiac Disease" Psychosomatics 45: 325-335.
Rasmussen et al., (1998) "Identification of two low-phytate barley (Hordeum vulgare L.) grain mutants by TLC and genetic analysis" Hereditas 129:107-112.
Senior (1998) "Uses of Plant Gene Silencing" Biotech. Genet. Engin. Revs. 15: 79-119.
Shan et al. (2002) "Structural Basis for Gluten Intolerance in Celiac Sprue" Science 297: 2275-2279.
Shewry and Halford (2002) "Cereal seed storage proteins: structures, properties and role in grain utilization" Journal of Experimental Botany 53:947-958.
Shewry et al (1979) "Protein Metabolism in Developing Endosperms of High-Lysine and Normal Barley" Cereal Chem. 56:110-117.
Shewry et al (1987) "Characterization and Genetic Control of the Prolamins of Haynaldia villosa: Relationship to Cultivated Species of the Triticeae (Rye, Wheat, and Barley)" Biochem. Genetics 25:309-325.
Shewry et al. (1978) "An Evaluation of Techniques for the Extraction of Hordein and Glutelin from Barley Seed and a Comparison of the Protein Composition of Bomi and Riso 1508" Journal of Experimental Botany 29:677-692.
Shewry et al. (1980) "Effect of High-Lysine Mutations on the Protein Fractions of Barley Grain" Biochemical Genetics 18:33-151.
Shippy et al. (1999) "The Hairpin Ribozyme" Mol. Biotech. 12: 117-129.
Skerritt (1988) "Hydrolysis of Barley Endosperm Storage Proteins During Malting. I. Analysis Using Monoclonal Antibodies" J. Cereal Science 7:251-263.
Slade and Knauf (2005) "TILLING moves beyond functional genomics into crop improvement" Transgenic Res 14: 109-115.
Smith et al. (2000) "Total silencing by intronspliced hairpin RNAs" Nature 407: 319-320.
Sollid (2002) "Coeliac Disease: Dissecting a Complex Inflammatory Disorder" Nature Reviews Immunology 2: 647-655.
Sorell et al. (1998) "An innovative sandwich ELISA system based on an antibody cocktail for gluten analysis" FEEBS Letts 439:46-50.
Sorensen (1992) "Methylation of B-hordein genes in barley endosperm is inversely correlated with gene activity and affected by the regulatory gene Lys3" PNAS 89:4119-4123.
Sorensen et al. (1996) "Hordein promoter methylation and transcriptional activity in wild-type and mutant barley endosperm" Mol Gen Genet 250:750-760.
Stepniak et al. (2006) "Highly efficient gluten degradation with a newly identified prolyl endoprotease: implications for celiac disease" Am J Physiol—Gastrointest Liver Physiol 291:621-629.
Tallberg (1977) "The amino-acid composition in endosperm and embryo of a barley variety and its high lysine mutant" Hereditas 87: 43-46.
Tanner et al. (2013) "Quantification of Hordeins by ELISA: The Correct Standard Makes a Magnitude of Difference" PLOS One 8(2): e56456 (1-14).
Thompson (2001) "Wheat starch, gliadin, and the gluten-free diet" J. Amer Diet Assoc 101: 1456-1459.
Tingay et al. (1997) "Agrobacterium tumefaciens-mediated barley transformation" Plant J 11:1369-1376.
Toriyama et al. (1986) "Haploid and diploid plant regeneration from protoplasts of anther callus in rice" Theor. Appl. Genet. 205:34.
Treem (2004) "Emerging concepts in celiac disease" Current Opinion in Pediatrics 16: 552-559.
Ullrich and Eslick (1977) "Inheritance of the shrunken endosperm character, sex3c, of Bomi Riso mutant 1508 and its association with lysine content." Barley Genetics Newsletter 7:66-73.
Ullrich and Eslick (1978) "Inheritance of the Associated Kernel Characters, High Lysine and Shrunken Endosperm, of the Barley Mutant Bomi, Riso 1508" Barley Genetics Newsletter 8:114-125.
Vader et al. (2003) "Characterization of Cereal Toxicity for Disease Patients Based on Protein Homology in Grains" Gastroenterology 125: 1105-1113.

(56) References Cited

OTHER PUBLICATIONS

Verkarre et al. (2004) "Gluten-Free Diet, Chromosomal Abnormalities, and Cancer Risk in Coeliac Disease" J Pediatric Gastroenterology and Nutrition 38: 140-142.
Wagner et al. (1992) "Coupling of adenovirus to transferrin-polylysine/DNA complexes greatly enhances receptor-mediated gene delivery and expression of transfected genes" Proc. Natl. Acad. Sci. USA 89:6099-6103.
Waterhouse et al. (1998) "Virus resistance and gene silencing in plants can be induced by simultaneous expression of sense and antisense RNA" Proc. Natl. Acad. Sci. USA 95: 13959-13964.
Wieser et al. (1994) Quantitative Determination of Gliadin Subgroups from Different Wheat Cultivars Journal of Cereal Science 19, 149-155.
Sep. 11, 2014 PCT International Search Report and Written Opinion issued in connection with PCT/AU2014/000619.
May 8, 2015 International Preliminary Report on Patentability issued in connection with PCT/AU2014/000619.
Colgrave et al., (2012) "What is in a Beer? Proteomic Characterization and Relative Quantification of Hordein (Gluten) in Beer" J. Froteome Res. 11: 386-396.
Fowell et al. (2006) "The epidemiology of coeliac disease in East Dorset 1993-2002: An assessment of the 'coeliac iceberg'. And preliminary evidence of case clustering" QJMed—an International Journal of Medicine 99:453-460.
Green and Jabri (2006) "Celiac Disease" Annual Review of Medicine 57:207-221.
et al. (2003) "Structural organization of the barley D-hordein locus in comparison with its orthologous regions of wheat genomes" Genome 46:1084-1097.
Hausch et al. (2002) "Intestinal digestive resistance of immunodominant gliadin peptides" Gastroenterology 122:A180.
Kahlenberg et al. (2006) "Monoclonal antibody R5 for detection of putatively coeliac-toxic gliadin peptides" European Food Research Technology. 222:78-82.
Lanzini et al. (2009) "Complete recovery of intestinal mucosa occurs very rarely in adult coeliac patient despite adherence to gluten-free diet" Alimentary Pharmacology & Therapeutics 29:1299-1308.
Ohlund et al. (2010). "Dietary shortcoming in children on a gluten-free diet" Journal of Human Nutrition and Dietetics 23:294-300.
Skovbjerg et al., (2004). "Deamidation and cross-linking of gliadin peptides by transglutaminases and the relation to celiac disease" Biochim. et Biophys. Acta—Mol. Bas.of Dis. 1690:220-230.
Tanner et al., (2010). "Dissecting the T-cell response to hordeins in coeliac disease can develop barley with reduced immunotoxicity" Aliment Pharmacol Ther. 32: 1184-1191.
Tye-Din et al. (2010) "Compregensive, Quantitative Mapping of T Cell Epitopes in Gluten in Celiac Disease" Science Translational Medicine 2:41-51.
Anderson O. D. (2013) "The B-hordein prolamin family of barley" NRC Research Press Genome 56: 179-185.
Brennan et al. (1998) "The Production and Characterisation of Hor 3 Null Lines of Barley Provides New Information on the Relationship of D Hordein to Malting Performance" Journal of Cereal Science 28: 291-299.
Cameron-Mills V and Brandt A (1988) "A γ-hordein gene" Plant Molecular Biology 11:449-461.
Fasoli et al. (2010) "Les Maitres de l'Orge: The Proteome Content of Your Beer Mug" Journal of Proteome Research 9: 5262-5269.
Kristoffersen HE and Flengsrud R (2000) "Separation and characterization of basic barley seed proteins" Electrophoresis 21: 3693-3700.
Picarello et al. (2011) "Proteomic and peptidomic characterization of beer: Immunological and technological implications" Food Chemistry 124: 1718-1726.
Arendt et al. (2008) "Gluten-free breads" Gluten-Free Cereal Products and Beverages Ed. Arendt and Bello, Elsevier Inc. Chapter 8: pp. 289-321.

Wieser H (2008) "Detection of gluten" Gluten-Free Cereal Products and Beverages Ed. Arendt and Bello, Elsevier Inc. Chapter 3: pp. 47-80.
Apr. 10, 2017 Office Action, issued in connection with Eurasian Patent Application No. 201690013, including English language translation.
Accession No. 1103203A, Forde et al. (1985).
Accession No. 110320313, Forde et al. (1985).
Accession No. 1103203C, Forde et al. (1985).
Accession No. 1210226A, Fabrijanski et al. (1988).
Accession No. 1307151A, Rasmussen et al. (1986).
Accession No. 1307151B, Rasmussen et al. (1986).
Accession No. 1411172A, Cameron-Mills and Brandt (1988).
Accession No. 1502200A, Fabrijanski et al. (1988).
Accession No. 1604464A, Egorov (1988).
GenBank Accession No. AAA32713, Fabrijanski et al. (1988).
GenBank Accession No. AAA32714, Chesnut et al. (1989).
GenBank Accession No. AAA32715, Chesnut et al. (1989).
GenBank Accession No. AAA32716, Chesnut et al. (1989).
GenBank Accession No. AAA32942, Forde et al. (1985).
GenBank Accession No. AAA32943, Rasmussen and Brandt (1986).
GenBank Accession No. AAA32944, Rasmussen and Brandt (1986).
GenBank Accession No. AAA32955, Cameron-Mill and Brandt (1988).
GenBank Accession No. AAA32967, Rasmussen et al. (1983).
GenBank Accession No. AAA92333, Entwistle (1988).
GenBank Accession No. AAF14232, Vrinten et al. (1999).
GenBank Accession No. AAB28161, Sainova et al. (1993).
GenBank Accession No. AAB71678, Skadsen et al. (1997).
GenBank Accession No. AAB71679, Skadsen et al. (1997).
GenBank Accession No. AAP31050, Gu et al. (2003).
GenBank Accession No. AAP31051, Gu et al. (2003).
GenBank Accession No. AAQ63842, Piston et al. (2003).
GenBank Accession No. AAQ63843, Piston et al. (2003).
GenBank Accession No. AAQ63844, Piston et al. (2003).
GenBank Accession No. AAQ63845, Piston et al. (2003).
GenBank Accession No. AAQ63846, Piston et al. (2003).
GenBank Accession No. AAQ63847, Piston et al. (2003).
GenBank Accession No. AAQ63848, Piston et al. (2003).
GenBank Accession No. AAQ63850, Piston et al. (2003).
GenBank Accession No. AAQ63851, Piston et al. (2003).
GenBank Accession No. AAQ63852, Piston et al. (2003).
GenBank Accession No. AAQ63853, Piston et al. (2003).
GenBank Accession No. AAQ63854, Piston et al. (2003).
GenBank Accession No. AAQ63855, Piston et al. (2003).
GenBank Accession No. AAQ63866, Piston et al. (2003).
GenBank Accession No. AAQ63867, Piston et al. (2003).
GenBank Accession No. AAQ63868, Piston et al. (2003).
GenBank Accession No. AAQ63869, Piston et al. (2003).
GenBank Accession No. AAQ63870, Piston et al. (2003).
GenBank Accession No. AAQ63871, Piston et al. (2003).
GenBank Accession No. AAQ63872, Piston et al. (2003).
GenBank Accession No. AAU06227, Hou et al. (2004).
GenBank Accession No. AAU06228, Hou et al. (2004).
GenBank Accession No. AAU06229, Hou et al. (2004).
GenBank Accession No. AAZ76368, Han et al. (2005).
GenBank Accession No. AAB23365, Rocher et al. (1992).
GenBank Accession No. AAB32025, Egorov et al. (1994).
GenBank Accession No. ABD14148, Potier (1993).
GenBank Accession No. ABA06537, Han et at. (2005).
GenBank Accession No. ABB82613, Han et al. (2005).
GenBank Accession No. ABB82614, Han et al. (2005).
GenBank Accession No. ABH01262, Han et al. (2006).
GenBank Accession No. AF016237, Skadsen et al. (1997).
GenBank Accession No. AF016238, Skadsen et al. (1997).
GenBank Accession No. AH005570, Skadsen et al. (1997).
GenBank Accession No. AJ580585, Snegaroff (2003).
GenBank Accession No. AY268139, Gu et al. (2003).
GenBank Accession No. AY338365, Piston et al. (2003).
GenBank Accession No. AY338366, Piston et al. (2003).
GenBank Accession No. AY338367, Piston et al. (2003).
GenBank Accession No. AY338368, Piston et al. (2003).
GenBank Accession No. AY338369, Piston et al. (2003).

(56) References Cited

OTHER PUBLICATIONS

GenBank Accession No. AY338370, Piston et al. (2003).
GenBank Accession No. AY338371, Piston et al. (2003).
GenBank Accession No. AY338372, Piston et al. (2003).
GenBank Accession No. AY338373, Piston et al. (2003).
GenBank Accession No. AY338374, Piston et al. (2003).
GenBank Accession No. AY338375, Piston et al. (2003).
GenBank Accession No. AY338376, Piston et al. (2003).
GenBank Accession No. AY338377, Piston et al. (2003).
GenBank Accession No. AY338378, Piston et al. (2003).
GenBank Accession No. AY338379, Piston et al. (2003).
GenBank Accession No. AY338380, Piston et al. (2003).
GenBank Accession No. AY338381, Piston et al. (2003).
GenBank Accession No. AY338382, Piston et al. (2003).
GenBank Accession No. AY338383, Piston et al. (2003).
GenBank Accession No. AY338384, Piston et al. (2003).
GenBank Accession No. AY338385, Piston et al. (2003).
GenBank Accession No. AY695367, Hou et al. (2004).
GenBank Accession No. AY695368, Hou et al. (2004).
GenBank Accession No. AY695369, Hou et al. (2004).
GenBank Accession No. AY700807, Piston et al. (2004).
GenBank Accession No. AY998005, Piston et al. (2005).
GenBank Accession No. AY998008, Piston et al. (2005).
GenBank Accession No. AY998009, Piston et al. (2005).
GenBank Accession No. AY998010, Piston et al. (2005).
GenBank Accession No. BAA11642, Hirota (1996).
GenBank Accession No. CAA25509, Rasmussen et al. (1983).
GenBank Accession No. CAA25912, Forde et al. (1985).
GenBank Accession No. CAA25913, Forde et al. (1985).
GenBank Accession No. CAA25914, Forde et al. (1985).
GenBank Accession No. CAA26889, Forde et al. (1985).
GenBank Accession No. CAA31861, Cameron-Mill and Brandt.
GenBank Accession No. CAA37729, Vincente (1990).
GenBank Accession No. CAA42642, Entwistle (1991).
GenBank Accession No. CAA48209, Halford (1992).
GenBank Accession No. CAA51204, Rechinger et al. (1993).
GenBank Accession No. CAA59104, Sorensen (1995).
GenBank Accession No. CAA60681, Brandt et al. (1985).
GenBank Accession No. CAE45747, Snegaroff (2003).
GenBank Accession No. CAE85306, Kock and Bauer (2003).
GenBank Accession No. CAE85351, Bauer (2003).
GenBank Accession No. D82941, Glass et al. (2000).
GenBank Accession No. DQ148297, Han et al. (2005).
GenBank Accession No. DQ178602, Han et al. (2005).
GenBank Accession No. DQ189997, Han et al. (2005).
GenBank Accession No. DQ267476, Han et al. (2005).
GenBank Accession No. DQ267477, Han et al. (2005).
GenBank Accession No. DQ267478, Han et al. (2005).
GenBank Accession No. DQ267479, Han et al. (2005).
GenBank Accession No. DQ267480, Han et al. (2005).
GenBank Accession No. DQ267481, Han et al. (2005).
GenBank Accession No. DQ826387, Han et al. (2006).
GenBank Accession No. J01237, Forde et al. (1981).
GenBank Accession No. K03147, Forde et al. (1985).
GenBank Accession No. M23836, Rasmussen et al. (1983).
GenBank Accession No. M23869, Rasmussen et al. (1983).
GenBank Accession No. M35610, Rasmussen et al. (1986).
GenBank Accession No. M35611, Rasmussen and Brandt (1986).
GenBank Accession No. M36378, Cameron-Mill and Brandt (1988).
GenBank Accession No. M36941, Entristle (1988).
Accession No. P06470, Forde et al. (1985).
Accession No. P06471, Forde et al. (1985).
Accession No. P06472, Forde et al. (1985).
Accession No. P17990, Cameron-Mills and Brandt (1988).
Accession No. P17991, Rasmussen et al. (1986).
Accession No. P17992, Rasmussen et al. (1986).
Accession No. P29835, Shorrosh et al. (1992).
Accession No. P80198, Rechinger et al. (1993).
Accession No. P27919, Fabijanski et al. (1988).
Accession No. P80356, Chesnut et al. (1989).
Accession No. P06293, Brandt et al. (1990).
Accession No. Q09095, Pernollet et al. (1987).
Accession No. Q09097, Pernollet et al. (1987).
Accession No. Q09114, Bietz et al. (1982).
GenBank Accession No. 66938, Sainova et al. (1993).
Accession No. S06211, Pernollet et al. (1987).
Accession No. S07621, Pernollet et al. (1987).
Accession No. S07622, Pernollet et al. (1987).
GenBank Accession No. X01024, Rasmussen et al. (1983).
GenBank Accession No. X01777, Forde et al. (1985).
GenBank Accession No. X01778, Forde et al. (1985).
GenBank Accession No. X01779, Forde et al. (1985).
GenBank Accession No. X03103, Forde et al. (1985).
GenBank Accession No. X13508, Cameron-Mill and Brandt (1988).
GenBank Accession No. X53690, Vincente (1990).
GenBank Accession No. X53691, Vincente (1990).
GenBank Accession No. X60037, Entistle et al. (1991).
GenBank Accession No. X68072, Halford (1992).
GenBank Accession No. X72628, Rechinger et al. (1993).
GenBank Accession No. X84368, Sorensen (1995).
GenBank Accession No. X87232, Brandt et al. (1985).
U.S. Appl. No. 60/964,672, filed Aug. 13, 2007, Tanner et al.
Aug. 15, 2016 First Office Action, issued in connection with Japanese Patent Application No. 2015-162679, including English language translation.
Nov. 18, 2016 First Office Action, issued in relation to Indian Patent Application No. 689/KOLNP/2010.
Jan. 17, 2017 First Examination Report, issued in connection with New Zealand Patent Application No. 631602.
Mar. 29, 2017 First Examination Report issued in connection with Australian Patent Application No. 201480852.
Jan. 23, 2017 Extended European Search Report, issued in connection with corresponding European Patent Application No. 14810699.0.
Brannan et al. (1998) "The production and characterization of Hor 3 null lines of barley provides new information on the relationship of D hordein to malting performance" Journal of Cereal Science 28(3): 291-299.
Tanner et al. (2010) "Dissecting the T-cell response to hordeins in coeliac disease can develop barley with reduced immunotoxicity" Alimentary Pharmacology & Therapeutics 32(9): 1184-1191.
Mar. 1, 2017 First Office Action, issued in connection with Chinese Patent Application No. 201480041134.6, including English language translation.
Jan. 5, 2016 Response, filed in connection with European Patent Application No. 08782920.6.
Feb. 5, 2016 Response, filed in connection with Canadian Patent Application No. 2,696,250.
Aug. 8, 2016 First Office Action, issued in connection with Japanese Patent Application No. 2015-162679, including English.
Jan. 25, 2017 Annex C—Notification of Stay Proceedings, issued in connection with European Patent Application No. 08782920.6.
English Language Translation of Jun. 6, 2017 Office Action, issued in connection with Brazilian Patent Application No. PI0815474-0.
Response filed Aug. 17, 2017 to Nov. 18, 2016 First Examination Report issued in connection with Indian Patent Application No. 689/KOLNP/2010.
Tallberg (1981) "Protein and lysine content in high-lysine double-recessives of barley. I. Combinations between mutant 1508 and a Hiproly back-cross" Hereditas 94: 253-260.
Tallberg (1982) "Characterization of high-lysine barley genotypes" Hereditas 96: 229-245.
Office Action dated Apr. 11, 2018 which issued in connection with corresponding Chilean Patent Application No. 201503590.
Apr. 26, 2019 Office Action in connection with corresponding Malaysian Patent Application No. PI2015704513.
2019 Communication pursuant to Article 94(3) EPC issued by the European Patent Office in connection with related European Patent Application No. 14810699.0.
Jul. 22, 2019 Office Action issued by the Eurasian Patent Office in connection with related Eurasian Patent Application No. 201690013, including English translation thereof.

(56) References Cited

OTHER PUBLICATIONS

Aug. 22, 2019 Office Action issued by the Intellectual Property Office of the Philippines in connection with related Philippine Patent Application No. 1-2015-502764.
Apr. 12, 2019 Office Action issued in connection with Philippine Patent Application No. 1-2015-502764.
Feb. 28, 2019 Office Action issued in connection with Chinese Patent Application No. 201480041134.6 including English language translation thereof.
Nov. 18, 2019 Office Action issued in connection with corresponding Japanese Patent Application No. 2016-518803, including English translation thereof.
Mar. 18, 2019 Office Action issued in connection with corresponding Japanese Patent Application No. 2016-518803, including English translation thereof.
Oct. 8, 2019 Office Action and its English translation which issued in connection with corresponding Mexican patent application MX/a/2015/01700.
Apr. 21, 2020 Office Action which issued in connection with corresponding Israeli Patent Application 242929 including English translation thereof.
Apr. 14, 2020 Response to Communication under Article 94(3) EPC filed in connection with corresponding European Patent Application No. EP 14810699.0.
Tanner, G. J., et al. (2016). Creation of the first ultra-low gluten barley (*Hordeum vulgare* L.) for coeliac and gluten-intolerant populations. *Plant biotechnology journal*, 14(4), 1139-1150.
Moehs, C. P., et al. (2019). Development of decreased-gluten wheat enabled by determination of the genetic basis of lys3a barley. *Plant physiology*, 179(4), 1692-1703.
Office Action dated Jan. 16, 2019 in connection with corresponding Chilean patent application No. 201503590 including English language translation thereof.
Office Action dated Feb. 22, 2019 in connection with corresponding Mexican Patent Application No. MX/a/2015/017009 including English language translation thereof.
Office Action dated May 7, 2018 in connection with Japanese Patent Application No. 2016-518803.
May 29, 2020 Office Action which issued in connection with corresponding Canadian Patent Application No. 2,914,687.
English translation of Jun. 23, 2020 Pre-Appeal Examination Report issued in connection with corresponding Japanese Patent Application No. 2016-518803.
English translation of Jul. 30, 2020 Office Action issued in connection with corresponding Mexican Patent Application No. MX/a/2015/017009.
Apr. 21, 2020 Response to Office Action filed in connection with corresponding Israeli Patent Application No. 242929.
Office Action dated Jan. 30, 2018 issued in connection with counterpart Eurasian Patent Application No. 201690013.
Office Action dated Aug. 10, 2018 in connection with Chinese Patent Application No. 201480041134.6, including English language translation thereof.
English translation of Office Action dated Oct. 19, 2018 in connection with corresponding Eurasian Patent Application No. 201690013.
English translation of Jul. 31, 2020 Office Action issued in connection with corresponding Vietnamese Patent Application No. 1-2016-00155.
English translation of Aug. 5, 2020 Office Action issued in connection with corresponding Ukrainian Patent Application No. 201600247.
Aug. 24, 2020 Office Action issued in connection with corresponding Philippine Patent Application No. 1-2015-502764.

\* cited by examiner

```
                      10        20        30        40        50        60        70        80
              ....|....|....|....|....|....|....|....|....|....|....|....|....|....|....|....|
Sloop con     MAKRLVLFVAVIVALVALTTAEREINGNNIFLDSRSRQLQCERELQESSLEACRRVVDQQLVGQLPWSTGLQMQCCQQLR
D-null con    MAKRLVLFVAVIVALVALTTAEPEINGNNIFLDSRSGQLQCERELQESSLEACRRVVDQQLVGQLPWSTGLQMQCCQQLR 90       100       110       120       130       140       150       160
              ....|....|....|....|....|....|....|....|....|....|....|....|....|....|....|....|
Sloop con     DVSPECRPVALSQVVRQYEQQTEVPSKGGSFYPGGTAPPLQQGGWWGTSVKWYYPDQTSSQQSWQGQQGYHQSVTSSQQP
D-null con    DVSPECRPVALSQVVRQYEQQTEVPSKGGSFYPGGTAPPLQQGGWWGTSVKWYYPDQTSSQQSWQGQQG*

170       180       190       200       210       220       230       240
              ....|....|....|....|....|....|....|....|....|....|....|....|....|....|....|....|
Sloop con     GQGQQGSYPGSTFPQQPGQGQQPGQRQPWSYPSATFPQQPGQ~~GQGQQGYYPGATSLLQPGQGQQGPYQSATSPQQPGQ 250       260       270       280       290       300       310       320
              ....|....|....|....|....|....|....|....|....|....|....|....|....|....|....|....|
Sloop con     GQGHQETYQFATSPHQPGQWQQPGQGQQGYYPSVTSPQQSGQGQTGYPSTTSPQQSGQGQQLGQGQQPGQGQQGYPSATF 330       340       350       360       370       380       390       400
              ....|....|....|....|....|....|....|....|....|....|....|....|....|....|....|....|
Sloop con     PQQPGQWQQGSYPSTTSPQQSGQGQQGYNPSGTSTQQPGQVQQLGQGQQGYYPIATSPQQPGQGQQLGQGQQPGHGQQLV 410       420       430       440       450       460       470       480
              ....|....|....|....|....|....|....|....|....|....|....|....|....|....|....|....|
Sloop con     QGQQQGQGQQGHYPSMTSPHQTGQGQKGYYPSAISPQQSGQGQQGYQPSGASSQGSVQGACQHSTSSPQQQAQGCQASSP 490       500       510       520       530       540       550       560
              ....|....|....|....|....|....|....|....|....|....|....|....|....|....|....|....|
Sloop con     KQGLGSLYYPSGAYTQQKPGQGYNPGGTSPLHQQGGGFGGGLTTEQPQGGKQPFHCQQTTVSPHQGQQTTVSPHQGQQTT 570       580       590       600       610       620       630       640
              ....|....|....|....|....|....|....|....|....|....|....|....|....|....|....|....|
Sloop con     VSPHQGQQTTVSPHQGQQTTVSPHQGQQTTVSPHQGQQTTVSPHPGQQTTVSPHQGQQTTVSPHPGQQTTVSPHQGQQTT 650       660       670       680       690       700       710       720
              ....|....|....|....|....|....|....|....|....|....|....|....|....|....|....|....|
Sloop con     VSPHQGQQTTVSPHQGQQTTVSPHQGQQPGEQPCGFPGQQTTVSLHHGQQSNELYYGSPYHVSVEQPSAS 730       740       750
              ....|....|....|....|....|.
Sloop con     LKVAKAQQLAAQLPAMCRLEGGGGLLASQ*
```

Figure 3

```
              10        20        30        40        50        60        70
         ....|....|....|....|....|....|....|....|....|....|....|....|....|....|
Sloop con    GACACATATTCTGCCAAAACCCCAGAACAATAATCACTTCTCGTAGATGAAGAGAACAGACCAAGATACA
D-null con   ......................................................................

80        90       100       110       120       130       140
         ....|....|....|....|....|....|....|....|....|....|....|....|....|....|
Sloop con    AACGTCCACGCTTCAGCAAACAGTACCCCAGAACTAGGATTAAGCCGATTACGCGGCTTTAGCAGACCGT
D-null con   ......................................................................

150       160       170       180       190       200       210
         ....|....|....|....|....|....|....|....|....|....|....|....|....|....|
Sloop con    CCAAAAAAACTGTTTTGCAAAGCTCCAATTCCTCCTTGCTTATCCAATTTCTTTTGTGTTGGCAAACTGC
D-null con   ......................................................................

220       230       240       250       260       270       280
         ....|....|....|....|....|....|....|....|....|....|....|....|....|....|
Sloop con    ACTTGTCCAACCGATTTTGTTCTTCCCGTGTTTCTTCTTAGGCTAACTAACACAGCCGTGCACATAGCCA
D-null con   ....C.....................A..........................................

290       300       310       320       330       340       350
         ....|....|....|....|....|....|....|....|....|....|....|....|....|....|
Sloop con    TGGTCCGGAATCTTCACCTCGTCCCTATAAAAGCCCAGCCAATCTCCACAATCTCATCATCACCGAGAAC
D-null con   ..........C...........................................................

360       370       380       390       400       410       420
         ....|....|....|....|....|....|....|....|....|....|....|....|....|....|
Sloop con    ACCGAGAACCACAAAACTAGAGATCAATTCATTGACAGTCCACCGAGATGGCTAAGCGGCTGGTCCTCTT M  A  K  R  L  V  L  F
D-null con   ......................................................................
                                                              M  A  K  R  L  V  L  F 430       440       450       460       470       480       490
         ....|....|....|....|....|....|....|....|....|....|....|....|....|....|
Sloop con    TGTGGCGGTAATCGTCGCCCTCGTGGCTCTCACCACCGCTGAACGTGAGATCAATGGGAACAACATTTTC V  A  V  I  V  A  L  V  A  L  T  T  A  E  R  E  I  N  G  N  N  I  F
D-null con   ..............................................C.......................
             V  A  V  I  V  A  L  V  A  L  T  T  A  E  P  E  I  N  G  N  N  I  F 500       510       520       530       540       550       560
         ....|....|....|....|....|....|....|....|....|....|....|....|....|....|
Sloop con    CTTGATAGCCGCTCTAGGCAGCTACAGTGTGAGCGCGAGCTCCAGGAGAGCTCGCTCGAGGCGTGCCGGC
             L  D  S  R  S  R  Q  L  Q  C  E  R  E  L  Q  E  S  S  L  E  A  C  R  R
D-null con   ...............G......................................................
             L  D  S  R  S  G  Q  L  Q  C  E  R  E  L  Q  E  S  S  L  E  A  C  R  R 570       580       590       600       610       620       630
         ....|....|....|....|....|....|....|....|....|....|....|....|....|....|
Sloop con    GGGTCGTGGACCAACAGCTGGTTGGCCAGCTGCCATGGAGCACGGGGCTCCAGATGCAGTGCTGCCAGCA
             V  V  D  Q  Q  L  V  G  Q  L  P  W  S  T  G  L  Q  M  Q  C  C  Q  Q
D-null con   ......................................................................
             V  V  D  Q  Q  L  V  G  Q  L  P  W  S  T  G  L  Q  M  Q  C  C  Q  Q 640       650       660       670       680       690       700
         ....|....|....|....|....|....|....|....|....|....|....|....|....|....|
Sloop con    GCTTCGGGACGTCAGCCCCGAGTGCCGCCCCGTCGCCCTCAGCCAGGTCGTGAGGCAATACGAGCAGCAA
                                                              5' D null marker
             L  R  D  V  S  P  E  C  R  P  V  A  L  S  Q  V  V  R  Q  Y  E  Q  Q
D-null con   ......................................................................
             L  R  D  V  S  P  E  C  R  P  V  A  L  S  Q  V  V  R  Q  Y  E  Q  Q
```

Figure 4

```
              710       720       730       740       750       760       770
           ....|....|....|....|....|....|....|....|....|....|....|....|....|....|
Sloop con  ACCGAGGTGCCATCCAAGGGAGGATCCTTCTACCCGGGCGGGACCGCACCGCCGCTGCAGCAAGGAGGAT
            T  E  V  P  S  K  G  G  S  F  Y  P  G  G  T  A  P  P  L  Q  Q  G  G  W
D-null con ........................................................................
            T  E  V  P  S  K  G  G  S  F  Y  P  G  G  T  A  P  P  L  Q  Q  G  G  W 780       790       800       810       820       830       840
           ....|....|....|....|....|....|....|....|....|....|....|....|....|....|
Sloop con  GGTGGGGAACCTCTGTAAAATGGTACTACCCAGACCAAACTTCTTCGCAACAGTCATGGCAAGGGCAACA
            W  G  T  S  V  K  W  Y  Y  P  D  Q  T  S  S  Q  Q  S  W  Q  G  Q  Q
D-null con ........................................................................
            W  G  T  S  V  K  W  Y  Y  P  D  Q  T  S  S  Q  Q  S  W  Q  G  Q  Q 850       860       870       880       890       900       910
           ....|....|....|....|....|....|....|....|....|....|....|....|....|....|
Sloop con  AGGGTACCACCAAAGCGTAACTTCTTCCCAGCAGCCAGGACAAGGGCAGCAAGGGTCCTACCCAGGTTCA
             KpnI
            G  Y  H  Q  S  V  T  S  S  Q  Q  P  G  Q  G  Q  Q  G  S  Y  P  G  S
D-null con ......G.................................................................
            G  *

920       930       940       950       960       970       980
           ....|....|....|....|....|....|....|....|....|....|....|....|....|....|
Sloop con  ACTTTCCCGCAGCAGCCAGGACAAGGACAACAACCAGGACAGAGGCAGCCATGGTCCTATCCAAGTGCAA
                                     3' D null marker
            T  F  P  Q  Q  P  G  Q  G  Q  Q  P  G  Q  R  Q  P  W  S  Y  P  S  A  T
D-null con ........................................................................

990      1000      1010      1020      1030      1040      1050
           ....|....|....|....|....|....|....|....|....|....|....|....|....|....|
Sloop con  CTTTCCCACAACAGCCAGGGC------AAGGGCAAGGGCAACAAGGGTACTACCCAGGCGCAACTTCCCT
            F  P  Q  Q  P  G  Q        G  Q  G  Q  Q  G  Y  Y  P  G  A  T  S  L
D-null con ....................AAGGGC.............................................

1060      1070      1080      1090      1100      1110      1120
           ....|....|....|....|....|....|....|....|....|....|....|....|....|....|
Sloop con  GCTGCAGCCAGGACAAGGGCAACAAGGGCCCTACCAGAGTGCAACTTCTCCACAGCAGCCAGGACAAGGA
            L  Q  P  G  Q  G  Q  Q  G  P  Y  Q  S  A  T  S  P  Q  Q  P  G  Q  G
D-null con ................................A......................................

1130      1140      1150      1160      1170      1180      1190
           ....|....|....|....|....|....|....|....|....|....|....|....|....|....|
Sloop con  CAGGGACACCAAGAGACCTATCAATTTGCAACTTCCCCGCATCAGCCAGGACAATGGCAACAACCAGGAC
            Q  G  H  Q  E  T  Y  Q  F  A  T  S  P  H  Q  P  G  Q  W  Q  Q  P  G  Q
D-null con ........A......C......C.A...............................................

1200      1210      1220      1230      1240      1250      1260
           ....|....|....|....|....|....|....|....|....|....|....|....|....|....|
Sloop con  AAGGGCAACAAGGGTACTACCCAAGTGTAACTTCTCCACAACAGTCGGGACAAGGGCAAACAGGGTACCC
            G  Q  Q  G  Y  Y  P  S  V  T  S  P  Q  Q  S  G  Q  G  Q  T  G  Y  P
D-null con ..............................................................CA........

1270      1280      1290      1300      1310      1320      1330
           ....|....|....|....|....|....|....|....|....|....|....|....|....|....|
Sloop con  AAGTACAACTTCTCCACAACAATCGGGGCAAGGGCAACAGCTGGGACAAGGGCAACAACCAGGACAAGGG
            S  T  T  S  P  Q  Q  S  G  Q  G  Q  Q  L  G  Q  G  Q  Q  P  G  Q  G
D-null con ........................................................................

1340      1350      1360      1370      1380      1390      1400
           ....|....|....|....|....|....|....|....|....|....|....|....|....|....|
Sloop con  CAACAAGGGTACCCAAGTGCAACTTTTCCACAACAGCCAGGACAATGGCAACAAGGGTCCTACCCAAGTA
            Q  Q  G  Y  P  S  A  T  F  P  Q  Q  P  G  Q  W  Q  Q  G  S  Y  P  S  T
D-null con ........................................................................
```

Figure 4 (continued)

```
                         1410      1420      1430      1440      1450      1460      1470
                    ....|....|....|....|....|....|....|....|....|....|....|....|....|....|
Sloop con           CAACTTCTCCGCAGCAGTCAGGACAAGGGCAACAAGGGTACAACCCAAGTGGAACTTCTACGCAGCAGCC
                     T  S  P  Q  Q  S  G  Q  G  Q  Q  G  Y  N  P  S  G  T  S  T  Q  Q  P
D-null con          ........................................................................

1480      1490      1500      1510      1520      1530      1540
                    ....|....|....|....|....|....|....|....|....|....|....|....|....|....|
Sloop con           GGGACAAGTGCAACAGTTGGGACAAGGGCAACAAGGGTACTACCCAATTGCAACTTCTCCGCAGCAGCCA
                     G  Q  V  Q  Q  L  G  Q  G  Q  Q  G  Y  Y  P  I  A  T  S  P  Q  Q  P
D-null con          ........................................................................

1550      1560      1570      1580      1590      1600      1610
                    ....|....|....|....|....|....|....|....|....|....|....|....|....|....|
Sloop con           GGACAAGGGCAACAGCTAGGACAAGGGCAACAACCAGGACATGGGCAACAGCTAGTGCAAGGGCAACAAC
                     G  Q  G  Q  Q  L  G  Q  G  Q  Q  P  G  H  G  Q  Q  L  V  Q  G  Q  Q
D-null con          ........................................................................

1620      1630      1640      1650      1660      1670      1680
                    ....|....|....|....|....|....|....|....|....|....|....|....|....|....|
Sloop con           AAGGACAAGGGCAACAAGGACACTACCCAAGTATGACTTCTCCGCACCAAACAGGACAAGGGCAAAAAGG
                     G  Q  G  Q  Q  G  H  Y  P  S  M  T  S  P  H  Q  T  G  Q  G  Q  K  G
D-null con          ........................................................................

1690      1700      1710      1720      1730      1740      1750
                    ....|....|....|....|....|....|....|....|....|....|....|....|....|....|
Sloop con           ATACTACCCAAGTGCAATTTCTCCGCAGCAGTCAGGACAAGGACAACAAGGATACCAGCCTAGTGGAGCT
                     Y  Y  P  S  A  I  S  P  Q  Q  S  G  Q  G  Q  Q  G  Y  Q  P  S  G  A
D-null con          ........................................................................

1760      1770      1780      1790      1800      1810      1820
                    ....|....|....|....|....|....|....|....|....|....|....|....|....|....|
Sloop con           TCTTCACAGGGGTCGGTGCAAGGGGCGTGCCAGCACAGCACATCTTCTCCGCAGCAGCAAGCACAAGGGT
                     S  S  Q  G  S  V  Q  G  A  C  Q  H  S  T  S  S  P  Q  Q  Q  A  Q  G  C
D-null con          ............................A...........................................

1830      1840      1850      1860      1870      1880      1890
                    ....|....|....|....|....|....|....|....|....|....|....|....|....|....|
Sloop con           GCCAAGCTTCTTCACCAAAGCAAGGGCTAGGGTCGTTGTACTACCCGAGTGGAGCTTATACACAACAGAA
                     Q  A  S  S  P  K  Q  G  L  G  S  L  Y  Y  P  S  G  A  Y  T  Q  Q  K
D-null con          ........................................................................

1900      1910      1920      1930      1940      1950      1960
                    ....|....|....|....|....|....|....|....|....|....|....|....|....|....|
Sloop con           ACCAGGGCAAGGGTACAACCCAGGTGGAACTTCTCCGCTGCACCAGCAAGGGGGAGGGTTCGGCGGCGGG
                     P  G  Q  G  Y  N  P  G  G  T  S  P  L  H  Q  Q  G  G  G  F  G  G  G
D-null con          ........................................................................

1970      1980      1990      2000      2010      2020      2030
                    ....|....|....|....|....|....|....|....|....|....|....|....|....|....|
Sloop con           TTAACGACGGAGCAACCGCAGGGAGGAAAGCAGCCATTCCATTGCCAGCAAACCACTGTCTCCCCTCACC
                     L  T  T  E  Q  P  Q  G  G  K  Q  P  F  H  C  Q  Q  T  T  V  S  P  H  Q
D-null con          ........................................................................

2040      2050      2060      2070      2080      2090      2100
                    ....|....|....|....|....|....|....|....|....|....|....|....|....|....|
Sloop con           AGGGTCAGCAAACCACTGTTTCCCCTCATCAGGGTCAGCAAACCACTGTCTCCCCTCATCAGGGTCAGCA
                     G  Q  Q  T  T  V  S  P  H  Q  G  Q  Q  T  T  V  S  P  H  Q  G  Q  Q
D-null con          ........................C...............................................
```

Figure 4 (continued)

```
                    2110      2120      2130      2140      2150      2160      2170
               ....|....|....|....|....|....|....|....|....|....|....|....|....|
Sloop con      AACCACTGTCTCCCCTCACCAGGGTCAGCAAACCACCGTCTCCCCTCACCAGGGTCAGCAAACCACCGTC
                T  T  V  S  P  H  Q  G  Q  Q  T  T  V  S  P  H  Q  G  Q  Q  T  T  V
D-null con     ..............................------------------------------------

2180      2190      2200      2210      2220      2230      2240
               ....|....|....|....|....|....|....|....|....|....|....|....|....|
Sloop con      TCCCCTCATCAGGGTCAGCAAACCACTGTCTCCCCTCATCCGGGTCAGCAAACCACTGTCTCCCCTCATC
                S  P  H  Q  G  Q  Q  T  T  V  S  P  H  P  G  Q  Q  T  T  V  S  P  H  Q
D-null con     ----------------------------------------------------------------

2250      2260      2270      2280      2290      2300      2310
               ....|....|....|....|....|....|....|....|....|....|....|....|....|
Sloop con      AGGGTCAGCAAACCACTGTCTCCCCTCATCCGGGTCAGCAAACCACTGTCTCCCCTCATCAGGGTCAGCA
                G  Q  Q  T  T  V  S  P  H  P  G  Q  Q  T  T  V  S  P  H  Q  G  Q  Q
D-null con     ----------..................................................

2320      2330      2340      2350      2360      2370      2380
               ....|....|....|....|....|....|....|....|....|....|....|....|....|
Sloop con      AACCACTGTCTCCCCTCATCAGGGTCAGCAAACCACCGTCTCCCCTCATCAGGGTCAGCAAACCACCGTC
                T  T  V  S  P  H  Q  G  Q  Q  T  T  V  S  P  H  Q  G  Q  Q  T  T  V
D-null con     ...........................C.................................

2390      2400      2410      2420      2430      2440      2450
               ....|....|....|....|....|....|....|....|....|....|....|....|....|
Sloop con      TCCCCTCATCAGGGTCAGCAAACCACCGTCTCCCCTCATCAGGGTCAGCAGCCCGGCGAGCAGCCTTGCG
                S  P  H  Q  G  Q  Q  T  T  V  S  P  H  Q  G  Q  Q  P  G  E  Q  P  C  G
D-null con     .................................C.............................

2460      2470      2480      2490      2500      2510      2520
               ....|....|....|....|....|....|....|....|....|....|....|....|....|
Sloop con      GTTTCCCTGGCCAGCAAACCACCGTGTCTCTGCACCATGGTCAGCAGTCCAACGAGTTGTACTACGGCAG
                 F  P  G  Q  Q  T  T  V  S  L  H  H  G  Q  Q  S  N  E  L  Y  Y  G  S
D-null con     .................................................................

2530      2540      2550      2560      2570      2580      2590
               ....|....|....|....|....|....|....|....|....|....|....|....|....|
Sloop con      CCCATACCATGTTAGCGTGGAGCAGCCGTCGGCCAGCCTAAAGGTAGCAAAGGCGCAGCAGCTCGCGGCG
                P  Y  H  V  S  V  E  Q  P  S  A  S  L  K  V  A  K  A  Q  Q  L  A  A
D-null con     ................................................................A 2600      2610      2620      2630      2640      2650      2660
               ....|....|....|....|....|....|....|....|....|....|....|....|....|
Sloop con      CAGCTGCCGGCAATGTGTCGGCTGGAGGGCGGCGGCGGCCTGTTGGCCAGCCAGTAGTAGAACTCTGGCA
                Q  L  P  A  M  C  R  L  E  G  G  G  G  L  L  A  S  Q  *
D-null con     .................................................................

2670      2680      2690      2700      2710      2720      2730
               ....|....|....|....|....|....|....|....|....|....|....|....|....|
Sloop con      GCTCGCATGGTGCTTGGGCATGCATGCATCTTAGCTATACAATAAACGTGACGTGTGCTTGCAGTTTTTC
D-null con     ............................C....................................

2740      2750      2760      2770      2780      2790      2800
               ....|....|....|....|....|....|....|....|....|....|....|....|....|
Sloop con      ATGTAACTAGGGTAAAACCCAACAATAATGCAAAACGGAAAGCTTCTCCATCCAAAAAAAGAACAAAACT
D-null con     .................................................................

2810      2820      2830      2840
               ....|....|....|....|....|....|....|....|....
Sloop con      GGTGCTATATATAGTATGCGCTACATGTCTCAGCTCATTGTCAG
D-null con     ............................................
```

Figure 4 (continued)

Figure 8:
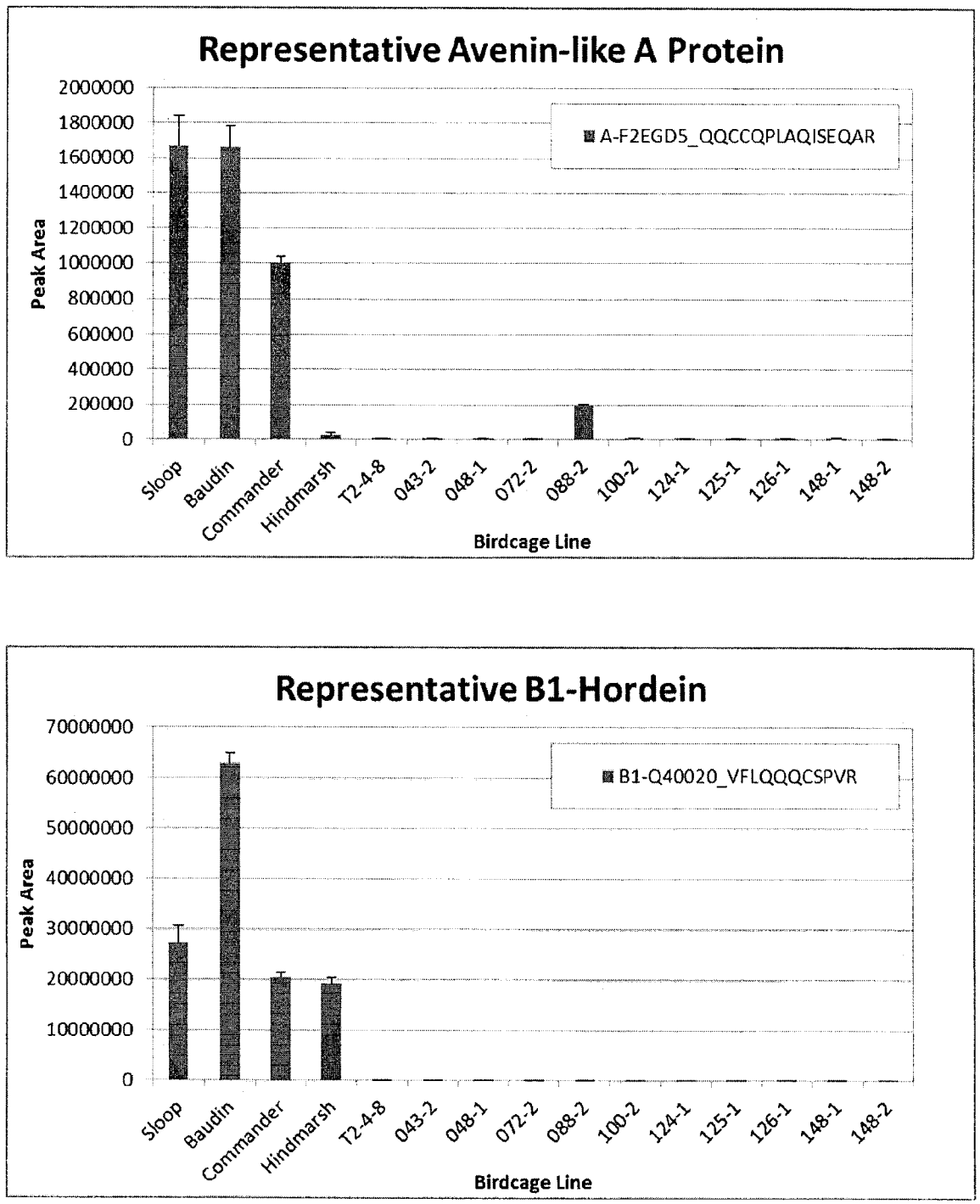
Figure 8:
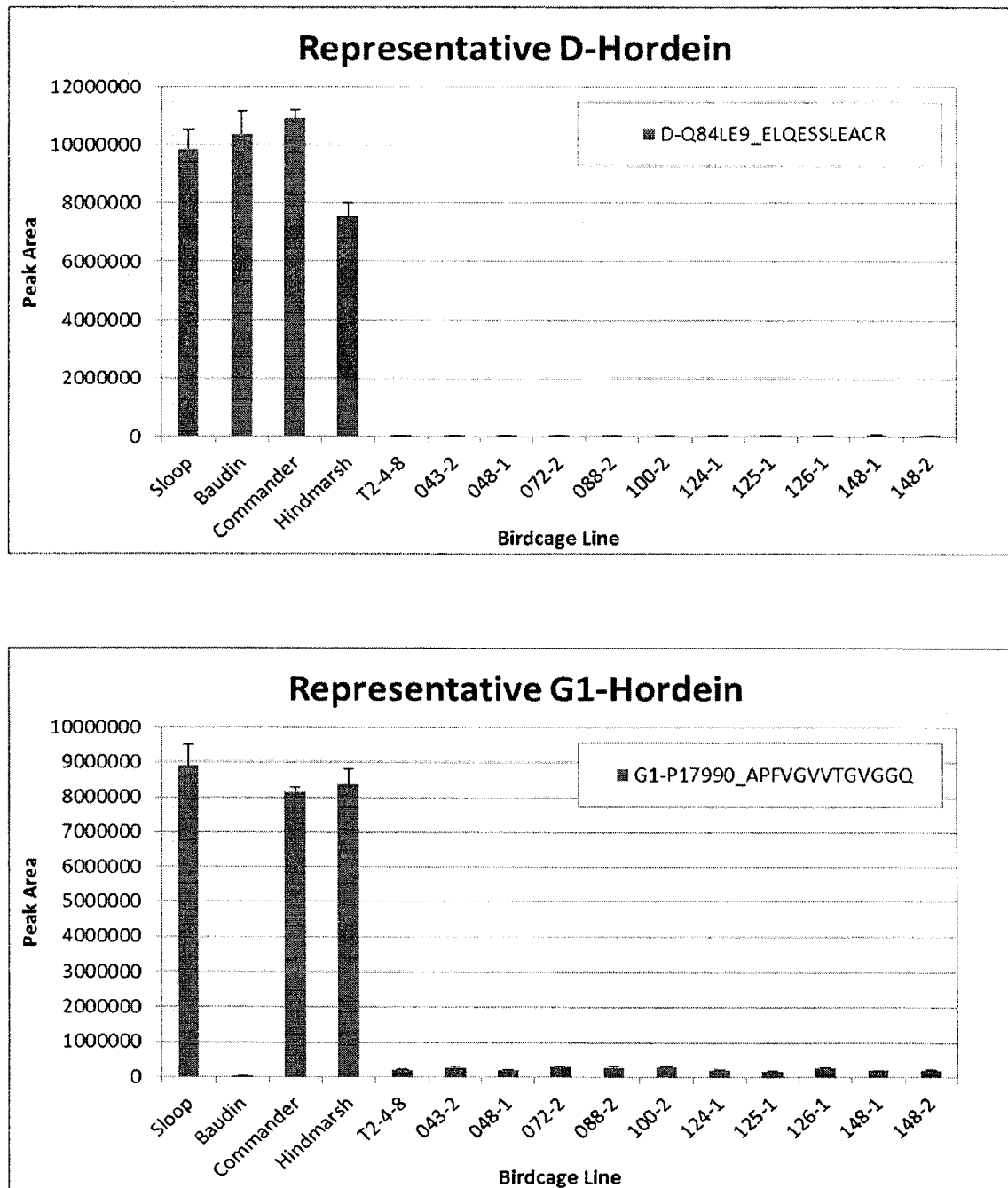
Figure 8:
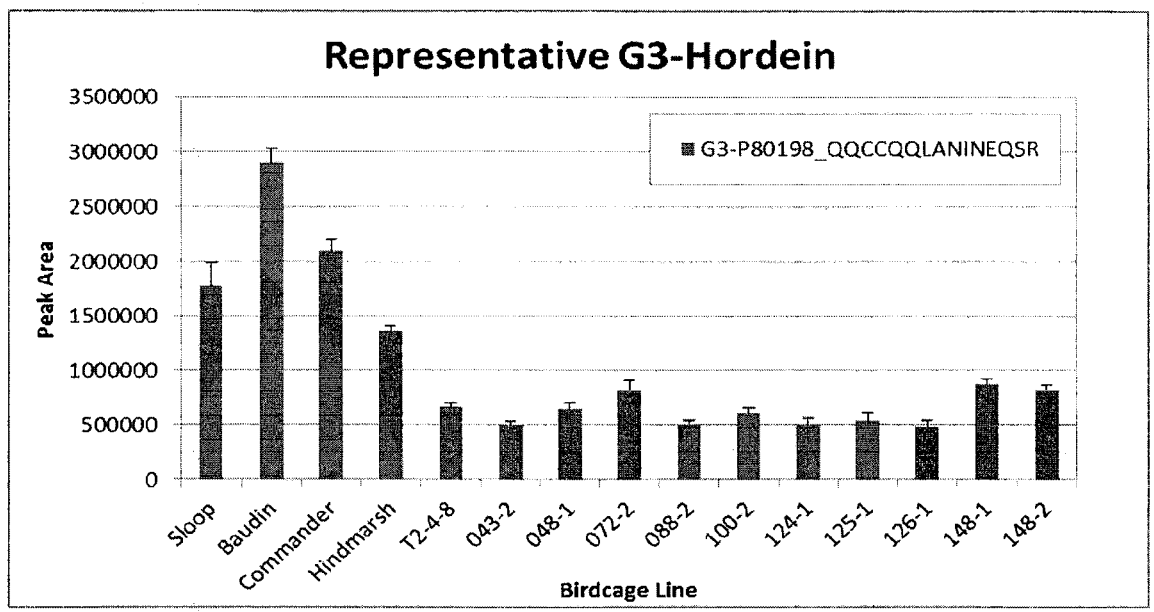

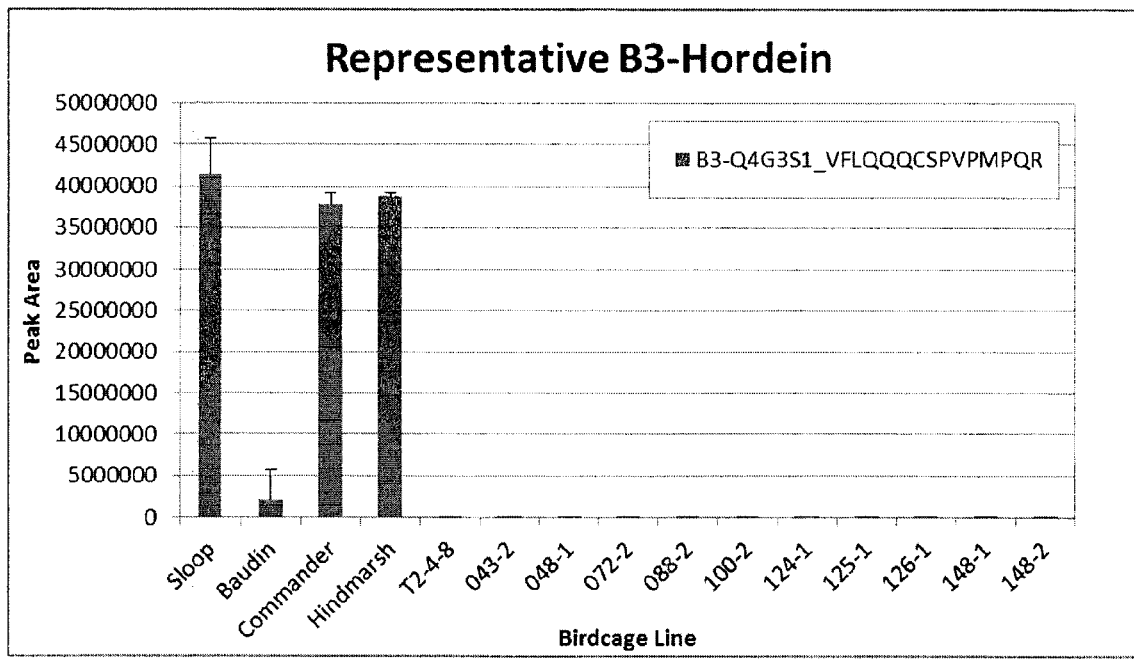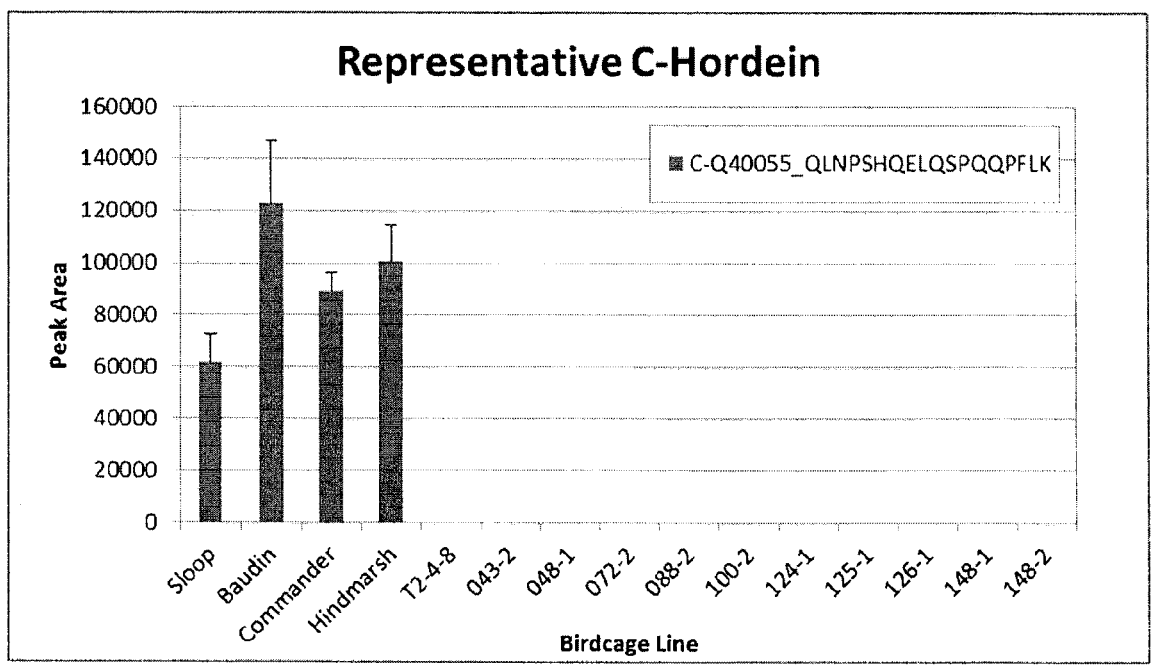
Figure 8 (continued)

```
SEQUENCE LISTING

<160> NUMBER OF SEQ ID NOS: 85

<210> SEQ ID NO 1
<211> LENGTH: 16
<212> TYPE: PRT
<213> ORGANISM: Triticum aestivum

<400> SEQUENCE: 1

Glu Leu Gln Pro Phe Pro Gln Pro Glu Leu Pro Tyr Pro Gln Pro Gln
1               5                   10                  15

<210> SEQ ID NO 2
<211> LENGTH: 15
<212> TYPE: PRT
<213> ORGANISM: Hordeum vulgare

<400> SEQUENCE: 2

Glu Gln Pro Phe Pro Gln Pro Glu Gln Pro Phe Pro Trp Gln Pro
1               5                   10                  15

<210> SEQ ID NO 3
<211> LENGTH: 16
<212> TYPE: PRT
<213> ORGANISM: Hordeum vulgare

<400> SEQUENCE: 3

Glu Pro Glu Gln Pro Ile Pro Glu Gln Pro Gln Pro Tyr Pro Gln Gln
1               5                   10                  15

<210> SEQ ID NO 4
<211> LENGTH: 17
<212> TYPE: PRT
<213> ORGANISM: Triticum aestivum
```

-continued

```
<400> SEQUENCE: 4

Gln Leu Gln Pro Phe Pro Gln Pro Gln Leu Pro Tyr Pro Gln Pro Gln
1               5                   10                  15

Ser

<210> SEQ ID NO 5
<211> LENGTH: 15
<212> TYPE: PRT
<213> ORGANISM: Triticum aestivum

<400> SEQUENCE: 5

Gln Gln Cys Cys Gln Pro Leu Ala Gln Ile Ser Glu Gln Ala Arg
1               5                   10                  15

<210> SEQ ID NO 6
<211> LENGTH: 11
<212> TYPE: PRT
<213> ORGANISM: Hordeum vulgare

<400> SEQUENCE: 6

Met Val Leu Gln Thr Leu Pro Ser Met Cys Arg
1               5                   10

<210> SEQ ID NO 7
<211> LENGTH: 8
<212> TYPE: PRT
<213> ORGANISM: Hordeum vulgare

<400> SEQUENCE: 7

Pro Gln Gln Pro Phe Pro Gln Gln
1               5

<210> SEQ ID NO 8
<211> LENGTH: 16
<212> TYPE: PRT
<213> ORGANISM: Hordeum vulgare

<400> SEQUENCE: 8

Phe Val Gln Pro Gln Gln Pro Phe Pro Leu Gln Pro His Gln Pro
1               5                   10                  15

<210> SEQ ID NO 9
<211> LENGTH: 15
<212> TYPE: PRT
<213> ORGANISM: Hordeum vulgare

<400> SEQUENCE: 9

Tyr Pro Glu Gln Pro Gln Gln Pro Phe Pro Trp Gln Gln Pro Thr
1               5                   10                  15

<210> SEQ ID NO 10
<211> LENGTH: 19
<212> TYPE: PRT
<213> ORGANISM: Hordeum vulgare

<400> SEQUENCE: 10

Leu Glu Arg Pro Gln Gln Leu Phe Pro Gln Trp Gln Pro Leu Pro Gln
1               5                   10                  15

Gln Pro Pro

<210> SEQ ID NO 11
<211> LENGTH: 18
```

```
<212> TYPE: PRT
<213> ORGANISM: Hordeum vulgare

<400> SEQUENCE: 11

Leu Ile Ile Pro Gln Gln Pro Gln Gln Pro Phe Pro Leu Gln Pro His
1               5                   10                  15

Gln Pro

<210> SEQ ID NO 12
<211> LENGTH: 5
<212> TYPE: PRT
<213> ORGANISM: Secale cereale

<400> SEQUENCE: 12

Gln Gln Pro Phe Pro
1               5

<210> SEQ ID NO 13
<211> LENGTH: 5
<212> TYPE: PRT
<213> ORGANISM: Secale cereale

<400> SEQUENCE: 13

Gln Gln Gln Phe Pro
1               5

<210> SEQ ID NO 14
<211> LENGTH: 5
<212> TYPE: PRT
<213> ORGANISM: Secale cereale

<400> SEQUENCE: 14

Leu Gln Pro Phe Pro
1               5

<210> SEQ ID NO 15
<211> LENGTH: 5
<212> TYPE: PRT
<213> ORGANISM: Secale cereale

<400> SEQUENCE: 15

Gln Leu Pro Phe Pro
1               5

<210> SEQ ID NO 16
<211> LENGTH: 16
<212> TYPE: PRT
<213> ORGANISM: Hordeum vulgare

<400> SEQUENCE: 16

Arg Val Val Asp Gln Gln Leu Val Gly Gln Leu Pro Trp Ser Thr Gly
1               5                   10                  15

<210> SEQ ID NO 17
<211> LENGTH: 16
<212> TYPE: PRT
<213> ORGANISM: Hordeum vulgare

<400> SEQUENCE: 17

Val Val Asp Gln Gln Leu Val Gly Gln Leu Pro Trp Ser Thr Gly Leu
1               5                   10                  15

<210> SEQ ID NO 18
<211> LENGTH: 15
```

```
<212> TYPE: PRT
<213> ORGANISM: Hordeum vulgare

<400> SEQUENCE: 18

Val Val Asp Gln Gln Leu Val Gly Gln Leu Pro Trp Ser Thr Gly
1               5                   10                  15

<210> SEQ ID NO 19
<211> LENGTH: 12
<212> TYPE: PRT
<213> ORGANISM: Hordeum vulgare

<400> SEQUENCE: 19

Val Val Asp Gln Gln Leu Val Gly Gln Leu Pro Trp
1               5                   10

<210> SEQ ID NO 20
<211> LENGTH: 12
<212> TYPE: PRT
<213> ORGANISM: Hordeum vulgare

<400> SEQUENCE: 20

Gln Leu Val Gly Gln Leu Pro Trp Ser Thr Gly Leu
1               5                   10

<210> SEQ ID NO 21
<211> LENGTH: 11
<212> TYPE: PRT
<213> ORGANISM: Hordeum vulgare

<400> SEQUENCE: 21

Gln Leu Val Gly Gln Leu Pro Trp Ser Thr Gly
1               5                   10

<210> SEQ ID NO 22
<211> LENGTH: 13
<212> TYPE: PRT
<213> ORGANISM: Hordeum vulgare

<400> SEQUENCE: 22

Leu Val Gly Gln Leu Pro Trp Ser Thr Gly Leu Gln Met
1               5                   10

<210> SEQ ID NO 23
<211> LENGTH: 11
<212> TYPE: PRT
<213> ORGANISM: Hordeum vulgare

<400> SEQUENCE: 23

Leu Val Gly Gln Leu Pro Trp Ser Thr Gly Leu
1               5                   10

<210> SEQ ID NO 24
<211> LENGTH: 10
<212> TYPE: PRT
<213> ORGANISM: Hordeum vulgare

<400> SEQUENCE: 24

Leu Val Gly Gln Leu Pro Trp Ser Thr Gly
1               5                   10

<210> SEQ ID NO 25
<211> LENGTH: 12
<212> TYPE: PRT
<213> ORGANISM: Hordeum vulgare
```

```
<400> SEQUENCE: 25

Val Gly Gln Leu Pro Trp Ser Thr Gly Leu Gln Met
1               5                   10

<210> SEQ ID NO 26
<211> LENGTH: 10
<212> TYPE: PRT
<213> ORGANISM: Hordeum vulgare

<400> SEQUENCE: 26

Val Gly Gln Leu Pro Trp Ser Thr Gly Leu
1               5                   10

<210> SEQ ID NO 27
<211> LENGTH: 15
<212> TYPE: PRT
<213> ORGANISM: Hordeum vulgare
<220> FEATURE:
<221> NAME/KEY: MOD_RES
<222> LOCATION: (1)..(1)
<223> OTHER INFORMATION: Pyroglutamic acid
<220> FEATURE:
<221> NAME/KEY: MOD_RES
<222> LOCATION: (15)..(15)
<223> OTHER INFORMATION: HexNAc

<400> SEQUENCE: 27

Gln Leu Ala Ala Gln Leu Pro Ala Met Cys Arg Leu Glu Gly Ser
1               5                   10                  15

<210> SEQ ID NO 28
<211> LENGTH: 26
<212> TYPE: PRT
<213> ORGANISM: Hordeum vulgare

<400> SEQUENCE: 28

Val Val Arg Gln Tyr Glu Gln Gln Thr Glu Val Pro Ser Lys Gly Gly
1               5                   10                  15

Ser Phe Tyr Pro Gly Gly Thr Ala Pro Pro
            20                  25

<210> SEQ ID NO 29
<211> LENGTH: 15
<212> TYPE: PRT
<213> ORGANISM: Hordeum vulgare

<400> SEQUENCE: 29

Phe Val Leu Pro Gln Gln Gln Ala Gln Phe Lys Val Val Gly Ser
1               5                   10                  15

<210> SEQ ID NO 30
<211> LENGTH: 10
<212> TYPE: PRT
<213> ORGANISM: Hordeum vulgare

<400> SEQUENCE: 30

Phe Val Leu Pro Gln Gln Gln Ala Gln Phe
1               5                   10

<210> SEQ ID NO 31
<211> LENGTH: 16
<212> TYPE: PRT
<213> ORGANISM: Hordeum vulgare

<400> SEQUENCE: 31
```

Ala Ile Val Met Gln Gln Val Gln Gln Val Gly His Gly Phe
1               5                   10                  15

<210> SEQ ID NO 32
<211> LENGTH: 19
<212> TYPE: PRT
<213> ORGANISM: Hordeum vulgare

<400> SEQUENCE: 32

Leu Glu Arg Pro Gln Gln Leu Phe Pro Gln Trp Gln Pro Leu Pro Gln
1               5                   10                  15

Gln Pro Pro

<210> SEQ ID NO 33
<211> LENGTH: 13
<212> TYPE: PRT
<213> ORGANISM: Hordeum vulgare

<400> SEQUENCE: 33

Leu Phe Pro Gln Trp Gln Pro Leu Pro Gln Gln Pro Pro
1               5                   10

<210> SEQ ID NO 34
<211> LENGTH: 12
<212> TYPE: PRT
<213> ORGANISM: Hordeum vulgare

<400> SEQUENCE: 34

Leu Gln Gln Leu Gly Gln Gly Met Pro Ile Gln Leu
1               5                   10

<210> SEQ ID NO 35
<211> LENGTH: 9
<212> TYPE: PRT
<213> ORGANISM: Hordeum vulgare

<400> SEQUENCE: 35

Val Val Gly Ser Leu Val Ile Gln Thr
1               5

<210> SEQ ID NO 36
<211> LENGTH: 19
<212> TYPE: PRT
<213> ORGANISM: Hordeum vulgare

<400> SEQUENCE: 36

Leu Gln Gln Pro Gln His Gln Phe Pro Gln Pro Thr Gln Gln Phe Pro
1               5                   10                  15

Gln Arg Pro

<210> SEQ ID NO 37
<211> LENGTH: 15
<212> TYPE: PRT
<213> ORGANISM: Hordeum vulgare

<400> SEQUENCE: 37

Tyr Pro Glu Gln Pro Gln Gln Pro Phe Pro Trp Gln Gln Pro Thr
1               5                   10                  15

<210> SEQ ID NO 38
<211> LENGTH: 12
<212> TYPE: PRT

```
<400> SEQUENCE: 38

Gly Val Val Gln Pro Gln Gln Leu Ala Gln Met Glu
1               5                   10

<210> SEQ ID NO 39
<211> LENGTH: 17
<212> TYPE: PRT
<213> ORGANISM: Hordeum vulgare
<220> FEATURE:
<221> NAME/KEY: MOD_RES
<222> LOCATION: (1)..(1)
<223> OTHER INFORMATION: Pyroglutamic acid

<400> SEQUENCE: 39

Gln Pro Gln His Gln Phe Pro Gln Pro Thr Gln Gln Phe Pro Gln Arg
1               5                   10                  15
Pro

<210> SEQ ID NO 40
<211> LENGTH: 14
<212> TYPE: PRT
<213> ORGANISM: Hordeum vulgare

<400> SEQUENCE: 40

Phe Val Gln Pro Gln Gln Gln Val Pro Val Glu Ile Thr Arg
1               5                   10

<210> SEQ ID NO 41
<211> LENGTH: 12
<212> TYPE: PRT
<213> ORGANISM: Hordeum vulgare

<400> SEQUENCE: 41

Phe Val Gln Pro Gln Gln Val Pro Val Glu Ile
1               5                   10

<210> SEQ ID NO 42
<211> LENGTH: 18
<212> TYPE: PRT
<213> ORGANISM: Hordeum vulgare

<400> SEQUENCE: 42

Leu Ile Ile Pro Gln Gln Pro Gln Gln Pro Phe Pro Leu Gln Pro His
1               5                   10                  15
Gln Pro

<210> SEQ ID NO 43
<211> LENGTH: 17
<212> TYPE: PRT
<213> ORGANISM: Hordeum vulgare

<400> SEQUENCE: 43

Ile Ile Pro Gln Gln Pro Gln Gln Pro Phe Pro Leu Gln Pro His Gln
1               5                   10                  15
Pro

<210> SEQ ID NO 44
<211> LENGTH: 12
<212> TYPE: PRT
<213> ORGANISM: Hordeum vulgare

<400> SEQUENCE: 44
```

-continued

Val Gln Val Gln Ile Pro Phe Val His Pro Ser Ile
1               5                   10

<210> SEQ ID NO 45
<211> LENGTH: 15
<212> TYPE: PRT
<213> ORGANISM: Hordeum vulgare

<400> SEQUENCE: 45

Ser Phe Gly Gln Pro Gln Gln Val Pro Val Glu Val Met Arg
1               5                   10                  15

<210> SEQ ID NO 46
<211> LENGTH: 28
<212> TYPE: PRT
<213> ORGANISM: Hordeum vulgare

<400> SEQUENCE: 46

Ile Ile Pro Gln Gln Pro Phe Pro Leu Gln Pro Gln Pro Phe Pro Gln
1               5                   10                  15

Gln Pro Gln Gln Pro Leu Pro Gln Pro Gln Gln Pro
            20                  25

<210> SEQ ID NO 47
<211> LENGTH: 14
<212> TYPE: PRT
<213> ORGANISM: Hordeum vulgare
<220> FEATURE:
<221> NAME/KEY: MOD_RES
<222> LOCATION: (6)..(6)
<223> OTHER INFORMATION: dansyl-glutamic acid (DEA)

<400> SEQUENCE: 47

Ile Pro Leu Gln Pro Gln Gln Pro Phe Pro Gln Gln Pro Pro
1               5                   10

<210> SEQ ID NO 48
<211> LENGTH: 14
<212> TYPE: PRT
<213> ORGANISM: Hordeum vulgare

<400> SEQUENCE: 48

Thr Leu Pro Thr Met Cys Ser Val Asn Val Pro Leu Tyr Arg
1               5                   10

<210> SEQ ID NO 49
<211> LENGTH: 16
<212> TYPE: PRT
<213> ORGANISM: Hordeum vulgare

<400> SEQUENCE: 49

Asp Val Ser Pro Glu Cys Arg Pro Val Ala Leu Ser Gln Val Val Arg
1               5                   10                  15

<210> SEQ ID NO 50
<211> LENGTH: 15
<212> TYPE: PRT
<213> ORGANISM: Hordeum vulgare

<400> SEQUENCE: 50

Gln Gln Cys Cys Gln Gln Leu Ala Asn Ile Asn Glu Gln Ser Arg
1               5                   10                  15

<210> SEQ ID NO 51
<211> LENGTH: 17

```
<212> TYPE: PRT
<213> ORGANISM: Hordeum vulgare

<400> SEQUENCE: 51

Cys Thr Ala Ile Asp Ser Ile Val His Ala Ile Phe Met Gln Gln Gly
1               5                   10                  15

Arg

<210> SEQ ID NO 52
<211> LENGTH: 15
<212> TYPE: PRT
<213> ORGANISM: Hordeum vulgare

<400> SEQUENCE: 52

Gln Gln Cys Cys Gln Pro Leu Ala Gln Ile Ser Glu Gln Ala Arg
1               5                   10                  15

<210> SEQ ID NO 53
<211> LENGTH: 11
<212> TYPE: PRT
<213> ORGANISM: Hordeum vulgare

<400> SEQUENCE: 53

Val Phe Leu Gln Gln Gln Cys Ser Pro Val Arg
1               5                   10

<210> SEQ ID NO 54
<211> LENGTH: 15
<212> TYPE: PRT
<213> ORGANISM: Hordeum vulgare

<400> SEQUENCE: 54

Val Phe Leu Gln Gln Gln Cys Ser Pro Val Pro Met Pro Gln Arg
1               5                   10                  15

<210> SEQ ID NO 55
<211> LENGTH: 18
<212> TYPE: PRT
<213> ORGANISM: Hordeum vulgare

<400> SEQUENCE: 55

Gln Leu Asn Pro Ser His Gln Glu Leu Gln Ser Pro Gln Gln Pro Phe
1               5                   10                  15

Leu Lys

<210> SEQ ID NO 56
<211> LENGTH: 11
<212> TYPE: PRT
<213> ORGANISM: Hordeum vulgare

<400> SEQUENCE: 56

Glu Leu Gln Glu Ser Ser Leu Glu Ala Cys Arg
1               5                   10

<210> SEQ ID NO 57
<211> LENGTH: 13
<212> TYPE: PRT
<213> ORGANISM: Hordeum vulgare

<400> SEQUENCE: 57

Ala Pro Phe Val Gly Val Thr Gly Val Gly Gly Gln
1               5                   10
```

```
<210> SEQ ID NO 58
<211> LENGTH: 15
<212> TYPE: PRT
<213> ORGANISM: Hordeum vulgare

<400> SEQUENCE: 58

Gln Gln Cys Cys Gln Gln Leu Ala Asn Ile Asn Glu Gln Ser Arg
1               5                   10                  15

<210> SEQ ID NO 59
<211> LENGTH: 13
<212> TYPE: PRT
<213> ORGANISM: Hordeum vulgare

<400> SEQUENCE: 59

Ala Pro Phe Val Gly Val Val Thr Gly Val Gly Gly Gln
1               5                   10

<210> SEQ ID NO 60
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 60
gacacatatt ctgccaaaac ccc                                          23

<210> SEQ ID NO 61
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 61
acgagggcga cgattaccgc                                              20

<210> SEQ ID NO 62
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 62
gagatcaatt cattgacagt ccacc                                        25

<210> SEQ ID NO 63
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 63
cttgtcctga ctgctgcgga gaaa                                         24

<210> SEQ ID NO 64
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 64
```
gcaacaagga cactacccaa gtatg                                              25

<210> SEQ ID NO 65
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 65
gctgacaatg agctgagaca tgtag                                              25

<210> SEQ ID NO 66
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 66
ggcaatacga gcagcaaac                                                     19

<210> SEQ ID NO 67
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 67
cctctgtcct ggttgttgtc                                                    20

<210> SEQ ID NO 68
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 68
tcgcaggatc ctgtacaacg                                                    20

<210> SEQ ID NO 69
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 69
caacaatgaa gaccttcctc                                                    20

<210> SEQ ID NO 70
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 70
cgagaaggta ccattactcc ag                                                 22

<210> SEQ ID NO 71
<211> LENGTH: 21
<212> TYPE: DNA
<213> ORGANISM: Artificial Sequence

```
<220> FEATURE:
<223> OTHER INFORMATION: Oligonucleotide primer

<400> SEQUENCE: 71
agtaacaatg aaggtccatc g                                              21

<210> SEQ ID NO 72
<211> LENGTH: 2838
<212> TYPE: DNA
<213> ORGANISM: Hordeum vulgare

<400> SEQUENCE: 72
gacacatatt ctgccaaaac cccagaacaa taatcacttc tcgtagatga agagaacaga    60
ccaagataca aacgtccacg cttcagcaaa cagtacccca gaactaggat taagccgatt   120
acgcggcttt agcagaccgt ccaaaaaaac tgttttgcaa agctccaatt cctccttgct   180
tatccaattt cttttgtgtt ggcaaactgc acttgtccaa ccgattttgt tcttcccgtg   240
tttcttctta ggctaactaa cacagccgtg cacatagcca tggtccggaa tcttcacctc   300
gtccctataa aagcccagcc aatctccaca atctcatcat caccgagaac accgagaacc   360
acaaaactag agatcaattc attgacagtc caccgagatg gctaagcggc tggtcctctt   420
tgtggcggta atcgtcgccc tcgtggctct caccaccgct gaacgtgaga tcaatgggaa   480
caacattttc cttgatagcc gctctaggca gctacagtgt gagcgcgagc tccaggagag   540
ctcgctcgag gcgtgccggc gggtcgtgga ccaacagctg gttggccagc tgccatggag   600
cacggggctc cagatgcagt gctgccagca gcttcgggac gtcagcccg agtgccgccc    660 cgtcgccctc agccaggtcg tgaggcaata cgagcagcaa accgaggtgc atccaaggg    720 aggatccttc tacccgggcg ggaccgcacc gccgctgcag caaggaggat ggtggggaac   780
ctctgtaaaa tggtactacc cagaccaaac ttcttcgcaa cagtcatggc aagggcaaca   840
agggtaccac caaagcgtaa cttcttccca gcagccagga caagggcagc aagggtccta   900
cccaggttca actttcccgc agcagccagg acaaggacaa caaccaggac agaggcagcc   960
atggtcctat ccaagtgcaa ctttcccaca cagccagggg caagggcaag gcaacaagg   1020 gtactaccca ggcgcaactt ccctgctgca gccaggacaa gggcaacaag ggccctacca   1080
gagtgcaact tctccacagc agccaggaca aggacaggga caccaagaga cctatcaatt   1140
tgcaacttcc ccgcatcagc caggacaatg gcaacaacca ggacaagggc aacagggta   1200 ctacccaagt gtaacttctc cacaacagtc gggacaaggg caaacagggt acccaagtac   1260
aacttctcca caacaatcgg ggcaagggca acagctggga caagggcaac aaccaggaca   1320
agggcaacaa gggtacccaa gtgcaacttt ccacaacag ccaggacaat ggcaacaagg   1380
gtcctaccca agtacaactt ctccgcagca gtcaggacaa gggcaacaag gtacaaccc   1440 aagtggaact tctacgcagc agccgggaca agtgcaacag ttgggacaag gcaacaagg   1500 gtactaccca attgcaactt ctccgcagca gccaggacaa gggcaacagc taggacaagg   1560
gcaacaacca ggacatgggc aacagctagt gcaagggcaa caacaaggac aagggcaaca   1620
aggacactac ccaagtatga cttcccgca ccaaacagga caagggcaaa aaggatacta    1680
cccaagtgca atttctccgc agcagtcagg acaaggacaa caaggatacc agcctagtgg   1740
agcttcttca caggggtcgg tgcaagggc gtgccagcac agcacatctt ctccgcagca   1800
gcaagcacaa gggtgccaag cttcttcacc aaagcaaggg ctaggggtct tgtactaccc   1860
gagtggagct tatacacaac agaaaccagg gcaagggtac aacccaggtg gaacttctcc   1920
```

```
gctgcaccag caaggggagg ggttcggcgg cgggttaacg acggagcaac cgcagggagg    1980
aaagcagcca ttccattgcc agcaaaccac tgtctcccct caccagggtc agcaaaccac    2040
tgtttcccct catcagggtc agcaaaccac tgtctcccct catcagggtc agcaaaccac    2100
tgtctcccct caccagggtc agcaaaccac cgtctcccct caccagggtc agcaaaccac    2160
cgtctcccct catcagggtc agcaaaccac tgtctcccct catccgggtc agcaaaccac    2220
tgtctcccct catcagggtc agcaaaccac tgtctcccct catccgggtc agcaaaccac    2280
tgtctcccct catcagggtc agcaaaccac tgtctcccct catcagggtc agcaaaccac    2340
cgtctcccct catcagggtc agcaaaccac cgtctcccct catcagggtc agcaaaccac    2400
cgtctcccct catcagggtc agcagcccgg cgagcagcct tgcggtttcc ctggccagca    2460
aaccaccgtg tctctgcacc atggtcagca gtccaacgag ttgtactacg gcagcccata    2520
ccatgttagc gtggagcagc cgtcggccag cctaaaggta gcaaaggcgc agcagctcgc    2580
ggcgcagctg ccggcaatgt gtcggctgga gggcggcggc ggcctgttgg ccagccagta    2640
gtagaactct ggcagctcgc atggtgcttg ggcatgcatg catcttagct atacaataaa    2700
cgtgacgtgt gcttgcagtt tttcatgtaa ctagggtaaa acccaacaat aatgcaaaac    2760
ggaaagcttc tccatccaaa aaaagaacaa aactggtgct atatatagta tgcgctacat    2820
gtctcagctc attgtcag                                                  2838

<210> SEQ ID NO 73
<211> LENGTH: 2724
<212> TYPE: DNA
<213> ORGANISM: Hordeum vulgare

<400> SEQUENCE: 73
gacacatatt ctgccaaaac cccagaacaa taatcacttc tcgtagatga agagaacaga      60
ccaagataca aacgtccacg cttcagcaaa cagtacccca gaactaggat taagccgatt     120
acgcggcttt agcagaccgt ccaaaaaaac tgttttgcaa agctccaatt cctccttgct     180
tatccaattt cttttgtgtt ggcaaactgc acttctccaa ccgattttgt tcttcccatg     240
tttcttctta ggctaactaa cacagccgtg cacatagcca tggtccggaa ccttcacctc     300
gtccctataa aagcccagcc aatctccaca atctcatcat caccgagaac accgagaacc     360
acaaaactag agatcaattc attgacagtc caccgagatg gctaagcggc tggtcctctt     420
tgtggcggta atcgtcgccc tcgtggctct caccaccgct gaacctgaga tcaatgggaa     480
caacattttc cttgatagcc gctctgggca gctacagtgt gagcgcgagc tccaggagag     540
ctcgctcgag gcgtgccggc gggtcgtgga ccaacagctg gttggccagc tgccatggag     600
cacggggctc cagatgcagt gctgccagca gcttcgggac gtcagccccg agtgccgccc     660
cgtcgccctc agccaggtcg tgaggcaata cgagcagcaa accgaggtgc catccaaggg     720
aggatccttc tacccgggcg ggaccgcacc gccgctgcag caaggaggat ggtgggaac     780 ctctgtaaaa tggtactacc cagaccaaac ttcttcgcaa cagtcatggc aagggcaaca     840
agggtagcac caaagcgtaa cttcttccca gcagccagga caagggcagc aagggtccta     900
cccaggttca actttcccgc agcagccagg acaaggacaa caaccaggac agaggcagcc     960
atggtcctat ccaagtgcaa cttcccacac acagccaggg caagggcaag gcaagggca   1020 acaagggtac tacccaggcg caacttccct gctgcagcca ggacaagggc aacaagggcc   1080
ctaccaaagt gcaacttctc cacagcagcc aggacaagga cagggacaac aagagcccta   1140
tccaattgca acttccccgc atcagccagg acaatggcaa caaccaggac aagggcaaca   1200
```

```
aggg tactac ccaagtgtaa cttctccaca acagtcggga caagggcaac aagggtaccc    1260
aagtacaact tctccacaac aatcggggca agggcaacag ctgggacaag ggcaacaacc    1320
aggacaaggg caacaaggt acccaagtgc aactttcca caacagccag gacaatggca     1380
```

```
agggtactac ccaagtgtaa cttctccaca acagtcggga caagggcaac aagggtaccc    1260
aagtacaact tctccacaac aatcggggca agggcaacag ctgggacaag ggcaacaacc    1320
aggacaaggg caacaaggt  acccaagtgc aacttttcca caacagccag gacaatggca    1380
acaagggtcc tacccaagta caacttctcc gcagcagtca ggacaagggc aacaagggta    1440
caacccaagt ggaacttcta cgcagcagcc gggacaagtg caacagttgg gacaagggca    1500
acaagggtac tacccaattg caacttctcc gcagcagcca ggacaagggc aacagctagg    1560
acaagggcaa caaccaggac atgggcaaca gctagtgcaa gggcaacaac aaggacaagg    1620
gcaacaagga cactacccaa gtatgacttc tccgcaccaa acaggacaag ggcaaaaagg    1680
atactaccca agtgcaattt ctccgcagca gtcaggacaa ggacaacaag gataccagcc    1740
tagtggagct tcttcacagg ggtcggtgca agggcgtac  cagcacagca catcttctcc    1800
gcagcagcaa gcacaagggt gccaagcttc ttcaccaaag caagggctag ggtcgttgta    1860
ctacccgagt ggagcttata cacaacagaa accaggcaa  gggtacaacc caggtggaac    1920
ttctccgctg caccagcaag ggggagggtt cggcggcggg ttaacgacgg agcaaccgca    1980
gggaggaaag cagccattcc attgccagca aaccactgtc tcccctcacc agggtcagca    2040
aaccactgtc tcccctcatc agggtcagca aaccactgtc tcccctcatc agggtcagca    2100
aaccactgtc tcccctcacc agggtcagca aaccactgtc tcccctcatc cgggtcagca    2160
aaccactgtc tcccctcatc agggtcagca aaccactgtc tcccctcatc cgggtcagca    2220
aaccaccgtc tcccctcatc agggtcagca aaccaccgtc tcccctcatc agggtcagca    2280
aaccaccgtc tcccctcacc agggtcagca gcccggcgag cagccttgcg gtttccctgg    2340
ccagcaaacc accgtgtctc tgcaccatgg tcagcagtcc aacgagttgt actacggcag    2400
cccataccat gttagcgtgg agcagccgtc ggccagccta aaggtagcaa aggcgcagca    2460
gctcgcggca cagctgccgg caatgtgtcg gctggagggc ggcggcggcc tgttggccag    2520
ccagtagtag aactctggca gctcgcatgg tgcttgggca tgcatgcacc ttagctatac    2580
aataaacgtg acgtgtgctt gcagtttttc atgtaactag ggtaaaaccc aacaataatg    2640
caaaacggaa agcttctcca tccaaaaaaa gaacaaaact ggtgctatat atagtatgcg    2700
ctacatgtct cagctcattg tcag                                          2724
```

<210> SEQ ID NO 74
<211> LENGTH: 747
<212> TYPE: PRT
<213> ORGANISM: Hordeum vulgare

<400> SEQUENCE: 74

Met Ala Lys Arg Leu Val Leu Phe Val Ala Val Ile Val Ala Leu Val
1               5                   10                  15

Ala Leu Thr Thr Ala Glu Arg Glu Ile Asn Gly Asn Asn Ile Phe Leu
            20                  25                  30

Asp Ser Arg Ser Arg Gln Leu Gln Cys Glu Arg Glu Leu Gln Glu Ser
        35                  40                  45

Ser Leu Glu Ala Cys Arg Arg Val Val Asp Gln Gln Leu Val Gly Gln
    50                  55                  60

Leu Pro Trp Ser Thr Gly Leu Gln Met Gln Cys Cys Gln Gln Leu Arg
65                  70                  75                  80

Asp Val Ser Pro Glu Cys Arg Pro Val Ala Leu Ser Gln Val Val Arg
                85                  90                  95

-continued

```
Gln Tyr Glu Gln Gln Thr Glu Val Pro Ser Lys Gly Gly Ser Phe Tyr
            100                 105                 110
Pro Gly Gly Thr Ala Pro Pro Leu Gln Gln Gly Gly Trp Trp Gly Thr
        115                 120                 125
Ser Val Lys Trp Tyr Tyr Pro Asp Gln Thr Ser Ser Gln Gln Ser Trp
    130                 135                 140
Gln Gly Gln Gln Gly Tyr His Gln Ser Val Thr Ser Ser Gln Pro
145                 150                 155                 160
Gly Gln Gly Gln Gln Gly Ser Tyr Pro Gly Ser Thr Phe Pro Gln Gln
                165                 170                 175
Pro Gly Gln Gly Gln Gln Pro Gly Gln Arg Gln Pro Trp Ser Tyr Pro
            180                 185                 190
Ser Ala Thr Phe Pro Gln Gln Pro Gly Gln Gly Gln Gly Gln Gln Gly
        195                 200                 205
Tyr Tyr Pro Gly Ala Thr Ser Leu Leu Gln Pro Gly Gln Gly Gln Gln
    210                 215                 220
Gly Pro Tyr Gln Ser Ala Thr Ser Pro Gln Gln Pro Gly Gln Gly Gln
225                 230                 235                 240
Gly His Gln Glu Thr Tyr Gln Phe Ala Thr Ser Pro His Gln Pro Gly
                245                 250                 255
Gln Trp Gln Gln Pro Gly Gln Gly Gln Gln Gly Tyr Tyr Pro Ser Val
            260                 265                 270
Thr Ser Pro Gln Gln Ser Gly Gln Gly Gln Thr Gly Tyr Pro Ser Thr
        275                 280                 285
Thr Ser Pro Gln Gln Ser Gly Gln Gly Gln Leu Gly Gln Gly Gln
    290                 295                 300
Gln Pro Gly Gln Gly Gln Gly Tyr Pro Ser Ala Thr Phe Pro Gln
305                 310                 315                 320
Gln Pro Gly Gln Trp Gln Gly Ser Tyr Pro Ser Thr Thr Ser Pro
                325                 330                 335
Gln Gln Ser Gly Gln Gly Gln Gly Tyr Asn Pro Ser Gly Thr Ser
            340                 345                 350
Thr Gln Gln Pro Gly Gln Val Gln Gln Leu Gly Gln Gly Gln Gly
        355                 360                 365
Tyr Tyr Pro Ile Ala Thr Ser Pro Gln Gln Pro Gly Gln Gly Gln Gln
    370                 375                 380
Leu Gly Gln Gly Gln Gln Pro Gly His Gly Gln Leu Val Gln Gly
385                 390                 395                 400
Gln Gln Gln Gly Gln Gly Gln Gln Gly His Tyr Pro Ser Met Thr Ser
                405                 410                 415
Pro His Gln Thr Gly Gln Gly Gln Lys Gly Tyr Tyr Pro Ser Ala Ile
            420                 425                 430
Ser Pro Gln Gln Ser Gly Gln Gly Gln Gln Gly Tyr Gln Pro Ser Gly
        435                 440                 445
Ala Ser Ser Gln Gly Ser Val Gln Gly Ala Cys Gln His Ser Thr Ser
    450                 455                 460
Ser Pro Gln Gln Gln Ala Gln Gly Cys Gln Ala Ser Ser Pro Lys Gln
465                 470                 475                 480
Gly Leu Gly Ser Leu Tyr Tyr Pro Ser Gly Ala Tyr Thr Gln Gln Lys
                485                 490                 495
Pro Gly Gln Gly Tyr Asn Pro Gly Gly Thr Ser Pro Leu His Gln Gln
            500                 505                 510
Gly Gly Gly Phe Gly Gly Gly Leu Thr Thr Glu Gln Pro Gln Gly Gly
```

```
            515                 520                 525
Lys Gln Pro Phe His Cys Gln Gln Thr Thr Val Ser Pro His Gln Gly
            530                 535                 540
Gln Gln Thr Thr Val Ser Pro His Gln Gly Gln Gln Thr Thr Val Ser
545                 550                 555                 560
Pro His Gln Gly Gln Gln Thr Thr Val Ser Pro His Gln Gly Gln Gln
                565                 570                 575
Thr Thr Val Ser Pro His Gln Gly Gln Gln Thr Thr Val Ser Pro His
            580                 585                 590
Gln Gly Gln Gln Thr Thr Val Ser Pro His Pro Gly Gln Gln Thr Thr
            595                 600                 605
Val Ser Pro His Gln Gly Gln Gln Thr Thr Val Ser Pro His Pro Gly
            610                 615                 620
Gln Gln Thr Thr Val Ser Pro His Gln Gly Gln Gln Thr Thr Val Ser
625                 630                 635                 640
Pro His Gln Gly Gln Gln Thr Thr Val Ser Pro His Gln Gly Gln Gln
                645                 650                 655
Thr Thr Val Ser Pro His Gln Gly Gln Gln Thr Thr Val Ser Pro His
            660                 665                 670
Gln Gly Gln Gln Pro Gly Glu Gln Pro Cys Gly Phe Pro Gly Gln Gln
            675                 680                 685
Thr Thr Val Ser Leu His His Gly Gln Gln Ser Asn Glu Leu Tyr Tyr
            690                 695                 700
Gly Ser Pro Tyr His Val Ser Val Glu Gln Pro Ser Ala Ser Leu Lys
705                 710                 715                 720
Val Ala Lys Ala Gln Gln Leu Ala Ala Gln Leu Pro Ala Met Cys Arg
                725                 730                 735
Leu Glu Gly Gly Gly Leu Leu Ala Ser Gln
                740                 745

<210> SEQ ID NO 75
<211> LENGTH: 149
<212> TYPE: PRT
<213> ORGANISM: Hordeum vulgare

<400> SEQUENCE: 75

Met Ala Lys Arg Leu Val Leu Phe Val Ala Val Ile Val Ala Leu Val
1               5                   10                  15
Ala Leu Thr Thr Ala Glu Pro Glu Ile Asn Gly Asn Asn Ile Phe Leu
                20                  25                  30
Asp Ser Arg Ser Gly Gln Leu Gln Cys Glu Arg Glu Leu Gln Glu Ser
            35                  40                  45
Ser Leu Glu Ala Cys Arg Arg Val Val Asp Gln Leu Val Gly Gln
        50                  55                  60
Leu Pro Trp Ser Thr Gly Leu Gln Met Gln Cys Cys Gln Gln Leu Arg
65                  70                  75                  80
Asp Val Ser Pro Glu Cys Arg Pro Val Ala Leu Ser Gln Val Val Arg
                85                  90                  95
Gln Tyr Glu Gln Gln Thr Glu Val Pro Ser Lys Gly Gly Ser Phe Tyr
            100                 105                 110
Pro Gly Gly Thr Ala Pro Pro Leu Gln Gln Gly Gly Trp Trp Gly Thr
            115                 120                 125
Ser Val Lys Trp Tyr Tyr Pro Asp Gln Thr Ser Ser Gln Gln Ser Trp
        130                 135                 140
```

Gln Gly Gln Gln Gly
145

<210> SEQ ID NO 76
<211> LENGTH: 2244
<212> TYPE: DNA
<213> ORGANISM: Hordeum vulgare

<400> SEQUENCE: 76

| | | | | |
|---|---|---|---|---|
| atggctaagc | ggctggtcct | ctttgtggcg | gtaatcgtcg | ccctcgtggc tctcaccacc | 60 |
| gctgaacgtg | agatcaatgg | gaacaacatt | ttccttgata | gccgctctag gcagctacag | 120 |
| tgtgagcgcg | agctccagga | gagctcgctc | gaggcgtgcc | ggcgggtcgt ggaccaacag | 180 |
| ctggttggcc | agctgccatg | gagcacgggg | ctccagatgc | agtgctgcca gcagcttcgg | 240 |
| gacgtcagcc | ccgagtgccg | ccccgtcgcc | ctcagccagg | tcgtgaggca atacgagcag | 300 |
| caaaccgagg | tgccatccaa | ggaggatccc | ttctacccgg | gcgggaccgc accgccgctg | 360 |
| cagcaaggag | gatggtgggg | aacctctgta | aatggtact | acccagacca aacttcttcg | 420 |
| caacagtcat | ggcaagggca | caagggtac | caccaaagcg | taacttcttc ccagcagcca | 480 |
| ggacaagggc | agcaagggtc | ctacccaggt | tcaactttcc | cgcagcagcc aggacaagga | 540 |
| caacaaccag | gacagaggca | gccatggtcc | tatccaagtg | caactttccc acaacagcca | 600 |
| gggcaagggc | aagggcaaca | agggtactac | ccaggcgcaa | cttccctgct gcagccagga | 660 |
| caagggcaac | aagggcccta | ccagagtgca | acttctccac | agcagccagg acaaggacag | 720 |
| ggacaccaag | agacctatca | atttgcaact | tccccgcatc | agccaggaca atggcaacaa | 780 |
| ccaggacaag | ggcaacaagg | gtactaccca | agtgtaactt | ctccacaaca gtcgggacaa | 840 |
| gggcaaacag | ggtacccaag | tacaacttct | ccacaacaat | cgggcaagg caacagctg | 900 |
| ggacaagggc | aacaaccagg | acaagggcaa | caagggtacc | caagtgcaac ttttccacaa | 960 |
| cagccaggac | aatggcaaca | agggtcctac | ccaagtacaa | cttctccgca gcagtcagga | 1020 |
| caagggcaac | aagggtacaa | cccaagtgga | acttctacgc | agcagccggg acaagtgcaa | 1080 |
| cagtttgggac | aagggcaaca | agggtactac | ccaattgcaa | cttctccgca gcagccagga | 1140 |
| caagggcaac | agctaggaca | agggcaacaa | ccaggacatg | gcaacagct agtgcaaggg | 1200 |
| caacaacaag | gacaagggca | acaaggacac | tacccaagta | tgacttctcc gcaccaaaca | 1260 |
| ggacaagggc | aaaaggata | ctacccaagt | gcaatttctc | cgcagcagtc aggacaagga | 1320 |
| caacaaggat | accagcctag | tggagcttct | tcacaggggt | cggtgcaagg ggcgtgccag | 1380 |
| cacagcacat | cttctccgca | gcagcaagca | caagggtgcc | aagcttcttc accaaagcaa | 1440 |
| gggctagggt | cgttgtacta | cccgagtgga | gcttatacac | aacagaaacc agggcaaggg | 1500 |
| tacaacccag | gtggaacttc | tccgctgcac | cagcaagggg | gagggttcgg cggcgggtta | 1560 |
| acgacggagc | aaccgcaggg | aggaaagcag | ccattccatt | gccagcaaac cactgtctcc | 1620 |
| cctcaccagg | gtcagcaaac | cactgtttcc | cctcatcagg | gtcagcaaac cactgtctcc | 1680 |
| cctcatcagg | gtcagcaaac | cactgtctcc | cctcaccagg | gtcagcaaac caccgtctcc | 1740 |
| cctcaccagg | gtcagcaaac | caccgtctcc | cctcatcagg | gtcagcaaac cactgtctcc | 1800 |
| cctcatccgg | gtcagcaaac | cactgtctcc | cctcatcagg | gtcagcaaac cactgtctcc | 1860 |
| cctcatccgg | gtcagcaaac | cactgtctcc | cctcatcagg | gtcagcaaac cactgtctcc | 1920 |
| cctcatcagg | gtcagcaaac | caccgtctcc | cctcatcagg | gtcagcaaac caccgtctcc | 1980 |
| cctcatcagg | gtcagcaaac | caccgtctcc | cctcatcagg | gtcagcagcc cggcgagcag | 2040 |

```
cccttgcggtt tccctggcca gcaaaccacc gtgtctctgc accatggtca gcagtccaac    2100
gagttgtact acggcagccc ataccatgtt agcgtggagc agccgtcggc cagcctaaag    2160
gtagcaaagg cgcagcagct cgcggcgcag ctgccggcaa tgtgtcggct ggagggcggc    2220
ggcggcctgt tggccagcca gtag                                           2244
```

<210> SEQ ID NO 77
<211> LENGTH: 450
<212> TYPE: DNA
<213> ORGANISM: Hordeum vulgare

<400> SEQUENCE: 77

```
atggctaagc ggctggtcct ctttgtggcg gtaatcgtcg ccctcgtggc tctcaccacc     60
gctgaacctg agatcaatgg gaacaacatt ttccttgata ccgctctgg gcagctacag    120 tgtgagcgcg agtccaggag gagctcgctc gaggcgtgcc ggcgggtcgt ggaccaacag    180
ctggttggcc agctgccatg gagcacgggg ctccagatgc agtgctgcca gcagcttcgg    240
gacgtcagcc ccgagtgccg ccccgtcgcc ctcagccagg tcgtgaggca atacgagcag    300
caaaccgagg tgccatccaa gggaggatcc ttctacccgg gcgggaccgc accgccgctg    360
cagcaaggag gatggtgggg aacctctgta aaatggtact acccagacca aacttcttcg    420
caacagtcat ggcaagggca acaagggtag                                    450
```

<210> SEQ ID NO 78
<211> LENGTH: 181
<212> TYPE: PRT
<213> ORGANISM: Hordeum vulgare

<400> SEQUENCE: 78

```
Leu Ala Cys Glu Val Leu Lys Glu Arg Ser Val Cys Ile Leu Gln Leu
1               5                   10                  15

His Tyr Val Gln Pro Ser Ile Leu Gln Gln Leu Asn Pro Cys Lys Val
            20                  25                  30

Phe Leu Gln Gln Gln Cys Ser Pro Val Arg Met Pro Gln Leu Ile Ala
        35                  40                  45

Arg Ser Gln Met Leu Gln Gln Ser Ser Cys His Val Leu Gln Gln Gln
    50                  55                  60

Cys Cys Gln Gln Leu Pro Gln Ile Pro Glu Gln Phe Arg His Glu Ala
65                  70                  75                  80

Ile Arg Ala Ile Val Tyr Ser Ile Phe Leu Gln Glu Gln Pro Gln Gln
                85                  90                  95

Ser Val Gln Gly Ala Ser Gln Pro Gln Gln Leu Gln Glu Glu Gln
            100                 105                 110

Val Gly Gln Cys Tyr Phe Gln Gln Pro Gln Pro Gln Leu Gly Gln
        115                 120                 125

Pro Gln Gln Val Pro Gln Ser Val Phe Leu Gln Pro His Gln Ile Ala
    130                 135                 140

Gln Leu Glu Ala Thr Asn Ser Ile Ala Leu Arg Thr Leu Pro Thr Met
145                 150                 155                 160

Cys Asn Val Asn Val Pro Leu Tyr Asp Ile Met Pro Phe Gly Val Gly
                165                 170                 175

Thr Arg Val Gly Val
            180
```

<210> SEQ ID NO 79
<211> LENGTH: 274

<212> TYPE: PRT
<213> ORGANISM: Hordeum vulgare

<400> SEQUENCE: 79

Met Lys Thr Phe Leu Ile Phe Ala Leu Leu Ala Ile Ala Ala Thr Asn
1               5                   10                  15

Thr Ile Ala Gln Gln Pro Phe Pro Gln Gln Pro Gln Pro Tyr Pro
            20                  25                  30

Gln Gln Pro Gln Pro Tyr Pro Gln Gln Pro Phe Pro Pro Gln Gln Pro
                35                  40                  45

Phe Pro Gln Gln Pro Pro Phe Trp Trp Gln Gln Pro Val Gln Ser Gln
50                  55                  60

Gln Gln Pro Cys Gln Gln Gln Thr Pro Leu Pro Gln Gly Gln Gln
65                  70                  75                  80

Tyr Gln Pro Leu Leu Gln Gln Ile Pro Phe Val His Pro Ser Val
                85                  90                  95

Leu Gln Gln Leu Asn Pro Cys Lys Val Phe Leu Gln Gln Cys Ser
                100                 105                 110

Pro Val Pro Met Pro Gln Arg Ile Ala Arg Ser Gln Met Leu Gln Gln
            115                 120                 125

Ser Ser Cys His Val Leu Gln Gln Cys Cys Lys Gln Leu Pro Gln
130                 135                 140

Ile Pro Glu Gln Phe Arg His Glu Ala Ile Arg Ala Ile Ile Tyr Ser
145                 150                 155                 160

Ile Ile Leu Gln Glu Gln Gln Val Gln Asp Phe Val Gln Pro Gln
                165                 170                 175

Gln Gln Gln Pro Gln Gln Ser Val Gln Gly Val Ser Gln Ser Gln Gln
                180                 185                 190

Gln Ser Gln Gln Pro Gln Leu Gly Gln Cys Ser Phe Gln Gln Pro Gln
                195                 200                 205

Leu Gln Gln Leu Gly Gln Gln Pro Gln Gln Gln Val Pro Leu Trp
                210                 215                 220

Ala Phe Leu Gln Pro Gln Gln Met Ala Gln Leu Glu Val Met Thr Ser
225                 230                 235                 240

Val Ala Leu Arg Thr Leu Pro Thr Met Cys Asn Val Asn Val Pro Leu
                245                 250                 255

Tyr Gly Ile Thr Thr Ser Val Pro Leu Ser Val Gly Thr Gly Val Gly
                260                 265                 270

Pro Tyr

<210> SEQ ID NO 80
<211> LENGTH: 347
<212> TYPE: PRT
<213> ORGANISM: Hordeum vulgare
<220> FEATURE:
<221> NAME/KEY: misc_feature
<222> LOCATION: (161)..(161)
<223> OTHER INFORMATION: Xaa can be any naturally occurring amino acid

<400> SEQUENCE: 80

Met Lys Thr Phe Leu Thr Phe Val Leu Leu Ala Met Ala Met Ser Ile
1               5                   10                  15

Val Thr Thr Ala Arg Gln Leu Asn Pro Ser His Gln Glu Leu Gln Ser
            20                  25                  30

Pro Gln Gln Pro Phe Leu Lys Gln Gln Ser Tyr Leu Gln Pro Tyr
                35                  40                  45

```
Pro Gln Gln Pro Tyr Leu Pro Gln Gln Pro Phe Pro Thr Pro Gln Gln
    50                  55                  60

Phe Phe Pro Tyr Leu Pro Gln Gln Thr Phe Pro Pro Ser Gln Gln Pro
65                  70                  75                  80

Asn Pro Leu Gln Pro Gln Gln Pro Phe Pro Leu Gln Pro Gln Pro Pro
                85                  90                  95

Gln Gln Pro Phe Pro Gln Pro Gln Gln Pro Asn Pro Gln Gln Pro Gln
            100                 105                 110

Gln Pro Phe Pro Arg Gln Pro Gln Gln Ile Val Pro Gln Gln Pro Gln
        115                 120                 125

Gln Pro Phe Pro Gln Gln Pro Gln Gln Pro Phe Pro Gln Pro Gln Gln
    130                 135                 140

Pro Phe Ser Trp Gln Pro Gln Gln Pro Phe Leu Gln Pro Leu Gln Leu
145                 150                 155                 160

Xaa Pro Leu Gln Ala Gln Gln Pro Phe Pro Leu Gln Pro Gln Leu Pro
                165                 170                 175

Phe Pro Gln Pro Gln Gln Pro Ile Gly Gln Gln Pro Lys Gln Pro Leu
                180                 185                 190

Leu Gln Gln Pro Gln Gln Thr Ile Pro Gln Gln Pro Gln Gln Pro Phe
        195                 200                 205

Pro Leu Gln Pro Gln Gln Pro Phe Pro Gln Gln Pro Gln Gln Pro Leu
    210                 215                 220

Pro Gln Gln Pro Gln Gln Ile Ile Ser Gln Gln Pro Gln Gln Pro Phe
225                 230                 235                 240

Pro Leu Gln Pro Gln Gln Pro Phe Pro Gln Pro Gln Pro Phe Pro Gln
                245                 250                 255

Glu Gln Pro Gln Gln Ala Phe Pro Leu Gln Pro Gln Gln Pro Phe Pro
            260                 265                 270

Glu Glu Ser Glu Gln Ile Ile Thr Gln Gln Pro Phe Pro Leu Gln Pro
        275                 280                 285

Gln Gln Leu Phe Pro Gln Gln Pro Gln Gln Pro Leu Pro Gln Pro Gln
    290                 295                 300

Gln Pro Phe Arg Gln Leu Pro Lys Tyr Ile Ile Pro Gln Gln Pro Gln
305                 310                 315                 320

Gln Pro Phe Leu Leu Gln Pro His Pro Gln Gln Pro Tyr Ala Gln
                325                 330                 335

Gln Asp Ile Trp Ser Asp Ile Ala Leu Leu Gly
                340                 345

<210> SEQ ID NO 81
<211> LENGTH: 305
<212> TYPE: PRT
<213> ORGANISM: Hordeum vulgare

<400> SEQUENCE: 81

Met Lys Ile Leu Ile Ile Leu Thr Ile Leu Ala Met Ala Thr Thr Phe
1               5                   10                  15

Ala Thr Ser Glu Met Gln Val Asn Pro Ser Val Gln Val Gln Pro Thr
                20                  25                  30

Gln Gln Gln Pro Tyr Pro Glu Ser Gln Gln Pro Phe Ile Ser Gln Ser
            35                  40                  45

Gln Gln Gln Phe Pro Gln Pro Gln Gln Pro Phe Pro Gln Gln Pro Gln
    50                  55                  60

Gln Pro Phe Pro Gln Ser Gln Gln Gln Cys Leu Gln Gln Pro Gln His
65                  70                  75                  80
```

Gln Phe Pro Gln Pro Thr Gln Phe Pro Gln Arg Pro Leu Leu Pro
                85                  90                  95

Phe Thr His Pro Phe Leu Thr Phe Pro Asp Gln Leu Leu Pro Gln Pro
                100                 105                 110

Pro His Gln Ser Phe Pro Gln Pro Pro Gln Ser Tyr Pro Gln Pro Pro
                115                 120                 125

Leu Gln Pro Phe Pro Gln Pro Pro Gln Lys Tyr Pro Glu Gln Pro
130                 135                 140

Gln Gln Pro Phe Pro Trp Gln Gln Pro Thr Ile Gln Leu Tyr Leu Gln
145                 150                 155                 160

Gln Gln Leu Asn Pro Cys Lys Glu Phe Leu Leu Gln Gln Cys Arg Pro
                165                 170                 175

Val Ser Leu Leu Ser Tyr Ile Trp Ser Lys Ile Val Gln Ser Ser
                180                 185                 190

Cys Arg Val Met Gln Gln Cys Cys Leu Gln Leu Ala Gln Ile Pro
                195                 200                 205

Glu Gln Tyr Lys Cys Thr Ala Ile Asp Ser Ile Val His Ala Ile Phe
                210                 215                 220

Met Gln Gln Gly Gln Arg Gln Gly Val Gln Ile Val Gln Gln Pro
225                 230                 235                 240

Gln Pro Gln Gln Val Gly Gln Cys Val Leu Val Gln Gly Gln Gly Val
                245                 250                 255

Val Gln Pro Gln Gln Leu Ala Gln Met Glu Ala Ile Arg Thr Leu Val
                260                 265                 270

Leu Gln Ser Val Pro Ser Met Cys Asn Phe Asn Val Pro Pro Asn Cys
                275                 280                 285

Ser Thr Ile Lys Ala Pro Phe Val Gly Val Val Thr Gly Val Gly Gly
                290                 295                 300

Gln
305

<210> SEQ ID NO 82
<211> LENGTH: 255
<212> TYPE: PRT
<213> ORGANISM: Hordeum vulgare

<400> SEQUENCE: 82

Met Gln Val Asn Pro Ser Val Gln Val Gln Pro Thr Gln Gln Gln Pro
1               5                   10                  15

Tyr Pro Glu Ser Gln Gln Pro Phe Ile Ser Gln Ser Gln Gln Gln Phe
                20                  25                  30

Pro Gln Pro Gln Gln Pro Phe Pro Gln Arg Pro Leu Leu Pro Phe Thr
                35                  40                  45

His Pro Phe Leu Thr Phe Pro Asp Gln Leu Leu Pro Gln Pro Pro His
                50                  55                  60

Gln Ser Phe Pro Gln Pro Pro Gln Ser Tyr Pro Gln Pro Pro Leu Gln
65                  70                  75                  80

Pro Phe Pro Gln Pro Pro Gln Gln Lys Tyr Pro Glu Gln Pro Gln Gln
                85                  90                  95

Pro Phe Pro Trp Gln Gln Pro Thr Ile Gln Leu Tyr Leu Gln Gln Gln
                100                 105                 110

Leu Asn Pro Tyr Lys Glu Phe Leu Leu Gln Gln Cys Arg Pro Val Ser
                115                 120                 125

Leu Leu Ser Tyr Leu Trp Ser Lys Ile Val Gln Gln Ser Ser Cys Arg

```
            130                 135                 140
Val Met Leu Gln Gln Cys Cys Leu Gln Leu Ala Gln Ile Pro Glu Gln
145                 150                 155                 160

Tyr Lys Cys Thr Ala Ile Asp Ser Ile Val His Ala Ile Phe Met Gln
                165                 170                 175

Gln Gly Gln Arg Gln Gly Val Gln Ile Val Gln Gln Pro Gln Gln Pro
                180                 185                 190

Gln Gln Val Gly Gln Cys Val Leu Val Gln Gly Gln Gly Val Val Gln
                195                 200                 205

Pro Gln Gln Leu Ala Gln Met Glu Ala Ile Arg Thr Leu Val Leu Gln
210                 215                 220

Ser Val Pro Ser Met Cys Asn Phe Asn Val Pro Pro Asn Cys Ser Thr
225                 230                 235                 240

Ile Lys Ala Pro Phe Val Gly Val Val Thr Gly Val Gly Gly Gln
                245                 250                 255

<210> SEQ ID NO 83
<211> LENGTH: 289
<212> TYPE: PRT
<213> ORGANISM: Hordeum vulgare

<400> SEQUENCE: 83

Ile Thr Thr Thr Thr Met Gln Phe Asn Pro Ser Gly Leu Glu Leu Glu
1               5                   10                  15

Arg Pro Gln Gln Leu Phe Pro Gln Trp Gln Pro Leu Pro Gln Gln Pro
                20                  25                  30

Pro Phe Leu Gln Gln Glu Pro Glu Gln Pro Tyr Pro Gln Gln Gln Pro
                35                  40                  45

Leu Pro Gln Gln Pro Phe Pro Gln Gln Pro Gln Leu Pro His Gln
50                  55                  60

His Gln Phe Pro Gln Gln Leu Pro Gln Gln Phe Pro Gln Gln Met
65                  70                  75                  80

Pro Leu Gln Pro Gln Gln Gln Phe Pro Gln Gln Met Pro Leu Gln Pro
                85                  90                  95

Gln Gln Gln Pro Gln Phe Pro Gln Lys Pro Phe Gly Gln Tyr Gln
                100                 105                 110

Gln Pro Leu Thr Gln Gln Pro Tyr Pro Gln Gln Pro Leu Ala Gln
                115                 120                 125

Gln Gln Pro Ser Ile Glu Glu Gln His Gln Leu Asn Leu Cys Lys Glu
130                 135                 140

Phe Leu Leu Gln Gln Cys Thr Leu Asp Glu Lys Val Pro Leu Leu Gln
145                 150                 155                 160

Ser Val Ile Ser Phe Leu Arg Pro His Ile Ser Gln Gln Asn Ser Cys
                165                 170                 175

Gln Leu Lys Arg Gln Gln Cys Cys Gln Gln Leu Ala Asn Ile Asn Glu
                180                 185                 190

Gln Ser Arg Cys Pro Ala Ile Gln Thr Ile Val His Ala Ile Val Met
                195                 200                 205

Gln Gln Gln Val Gln Gln Val Gly His Gly Phe Val Gln Ser Gln
                210                 215                 220

Leu Gln Gln Leu Gly Gln Gly Met Pro Ile Gln Leu Gln Gln Pro
225                 230                 235                 240

Gly Gln Ala Phe Val Leu Pro Gln Gln Ala Gln Phe Lys Val Val
                245                 250                 255
```

```
Gly Ser Leu Val Ile Gln Thr Leu Pro Met Leu Cys Asn Val His Val
            260                 265                 270

Pro Pro Tyr Cys Ser Pro Phe Gly Ser Met Ala Thr Gly Ser Gly Gly
            275                 280                 285

Gln

<210> SEQ ID NO 84
<211> LENGTH: 173
<212> TYPE: PRT
<213> ORGANISM: Hordeum vulgare

<400> SEQUENCE: 84

Met Lys Thr Met Leu Ile Leu Ala Leu Ile Ala Phe Ala Ala Thr Ser
1               5                   10                  15

Ala Val Ala Gln Leu Asp Thr Thr Cys Ser Gln Gly Tyr Gly Gln Cys
            20                  25                  30

Gln Gln Gln Pro Gln Gln Met Asn Thr Cys Ala Ala Phe Leu Gln
            35                  40                  45

Gln Cys Ser Arg Thr Pro Tyr Val Gln Ser Gln Met Trp Gln Ala Ser
    50                  55                  60

Gly Cys Gln Leu Met Arg Gln Gln Cys Cys Gln Pro Leu Ala Gln Ile
65                  70                  75                  80

Ser Glu Gln Ala Arg Cys Gln Ala Val Cys Ser Met Ala Gln Val Ile
                85                  90                  95

Met Arg Gln Gln Gln Gly Gln Ser Phe Thr Gln Pro Gln Gln Gln Gln
            100                 105                 110

Ser Gln Ser Phe Gly Gln Pro Gln Gln Val Pro Val Glu Val Met
            115                 120                 125

Arg Met Val Leu Gln Thr Leu Pro Ser Met Cys Ser Val Asn Ile Pro
    130                 135                 140

Gln Tyr Cys Thr Thr Thr Pro Cys Ser Thr Ile Thr Pro Thr Ile Tyr
145                 150                 155                 160

Ser Ile Pro Met Ala Ala Thr Cys Ala Gly Gly Val Cys
                165                 170

<210> SEQ ID NO 85
<211> LENGTH: 13
<212> TYPE: PRT
<213> ORGANISM: Hordeum vulgare

<400> SEQUENCE: 85

Ala Gln Gln Leu Ala Ala Gln Leu Pro Ala Met Cys Arg
1               5                   10
```

BARLEY WITH VERY LOW LEVELS OF HORDEINS

CROSS-REFERENCE TO RELATED APPLICATIONS

The present application is a § 371 national stage of PCT International Application No. PCT/AU2014/000619, filed Jun. 13, 2014, claiming priority of Australian Patent Application No. 2013902565, filed Jul. 11, 2013 and Australian Patent Application No. 2013902140, filed Jun. 13, 2013, the contents of each of which are hereby incorporated by reference in their entirety.

REFERENCE TO A SEQUENCE LISTING

This application incorporates-by-reference nucleotide and/or amino acid sequences which are present in the file named "151210_88101_Sequence_Listing_JAM.txt," which is 48.6 kilobytes in size, and which was created Dec. 4, 2015 in the IBM-PC machine format, having an operating system compatibility with MS-Windows, which is contained in the text file filed Dec. 10, 2015 as part of this application.

FIELD OF THE INVENTION

The present invention relates to methods of producing a food or malt-based beverage suitable for consumption by a subject with Coeliac's disease. In particular, the present invention relates to methods of producing a food or malt-based beverage with very low levels of hordeins. Also provided are barley plants which produce grain that can be used in the methods of the invention.

BACKGROUND OF THE INVENTION

Coeliac disease (CD) is a T-cell mediated enteropathy triggered by the consumption of prolamins from grains such as wheat, barley and rye. Clinical symptoms of CD include fatigue, diarrhoea, abdominal distension, weight loss, anemia and neurological disorders (Green et al., 2006). CD has been associated with increased rates of intestinal malignancy, such as 10-fold increased risk of intestinal cancer, a 3- to 6-fold increase in the risk of non-Hodgkin lymphoma and a 28-fold increased risk of intestinal T-cell lymphoma (Green et al., 2009) as well as increased rates of anemia, osteoporosis, neurologic deficits, and additional autoimmune disorders such as diabetes (Skovbjerg et al., 2005). In the case of the most studied prolamin, α-gliadin, toxicity is largely mediated by a single glutamine in a single peptide (Anderson et al., 2000; Shan et al., 2002) that produces a destructive cascade of reactions that eventually damage the small intestinal villi, reducing nutrient absorption and impacting on health. Coeliac toxic epitopes for all known prolamin proteins from wheat, barley and rye have now been extensively mapped using unbiased T-cell populations isolated from the peripheral blood of HLA-DQ2$^+$ coeliacs following short-term dietary challenge with wheat, barley and rye (Tye-Din et al., 2010). Surprisingly, only three highly immunogenic peptides, derived from α-gliadin (ELQPFPQPELPYPQPQ, SEQ ID NO: 1), ω-gliadin/C-hordein (EQPFPQPEQPFPWQP, SEQ ID NO: 2), and B-hordein (EPEQPIPEQPQPYPQQ, SEQ ID NO: 3), could account for 90% of the coeliac-specific response, elicited by the full complement of wheat, barley and rye proteins.

The only current treatment for CD is lifelong avoidance of dietary gluten, which consists of a family of similar proteins found in wheat (gliadins, glutenins), rye (secalins), barley (hordeins), and oats (avenins). However, such diets are costly (Lee et al., 2007) and associated with low fibre and high sugar intakes (Kupper et al., 2005; Wild et al., 2010; Ohlund et al., 2010), which in themselves are health risks. Avoidance of dietary gluten leads to a normalization of health statistics in most, but not all coeliacs (Lanzini et al., 2009; Rubio-Tapia et al., 2010). Approximately 1% of most populations world-wide suffer from coeliac disease, however, up to 50% of adults remain undiagnosed or do not display overt symptoms (Catassi et al., 1994; Fowell et al., 2006).

The major families of seed proteins in the cereals of the Triciceae are the albumins, globulins and the gluten-like proteins, collectively called prolamins (Shewry and Tatham, 1990). The albumins and globulins are widely distributed amongst flowering plants, but the prolamins are restricted to the grasses, particularly the sub-family Pooideae (Hausch et al., 2002). Prolamins, so named because they contain a high proportion of the amino acids proline and glutamine, resist proteolysis during digestion (Hausch et al., 2002). The α-gliadin gene was the first prolamin gene to be cloned and much is now known about the role of this protein in coeliac disease (Kasarda et al., 1984). The toxicity of this prolamin is focused on a single peptide 57-QLQP-FPQPQLPYPQPQS-73 (SEQ ID NO: 4) with the glutamine residue Q65 being the key amino acid. Mutation of this single glutamine to, for example, a lysine, abolishes the coeliac toxicity of this prolamin (Anderson et al., 2000). Partially hydrolyzed peptides cross the epithelium and access the lamina propria by an unknown mechanism; here Q65 is de-amidated by tissue transglutaminase (tTG) to E65 (glutamate), increasing the immuno-stimulatory potential of the peptide (Skovbjerg et al., 2004). The negative charge facilitates binding of the peptide to DQ2 (or less commonly DQ8) receptors on the surface of Antigen Presenting Cells, allowing presentation of the peptides to particular gluten-specific, DQ2-restricted, CD4+ T-cells, which are targeted to the intestine. Thus activated, the CD4-T cells undergo clonal expansion and in turn assist the expansion of gluten-specific- and TG2-specific-B-cells with the resultant production of anti-TG2 and anti-gluten antibodies characteristic of coeliac disease. A cell-mediated Th1 response also occurs, through the secretion of inflammatory cytokines (Tjon et al., 2010). Thus, a simple protein interaction, facilitated by the introduction of a single negatively charged residue, initiates a series of specific and targeted cascades, ultimately leading to destruction of the intestinal villi.

Barley (*Hordeum vulgare* L.) is a widely grown cereal used to produce malt for the brewing and food industry. Malted barley is the main ingredient in beer, supplying the carbohydrate source for fermentation. Unfortunately for coeliacs, barley beer also contains a low, but coeliac-toxic level of hordein (gluten) (Dostalek et al., 2006). The hordeins account for half of the barley grain protein (Moravcova et al., 2009), and are composed of four multi-gene families: the B-hordeins (30-45 kDa; 70% of hordein content) and the C-hordeins (45-75 kDa; 20% of hordein content) dominate the grain hordein, while the D- (105 kDa) and γ-hordeins (35-40 kDa) are minor components (Shewry et al., 1999). Malted sorghum, millet, and buckwheat are used as gluten-free alternatives for beer production (Wijngaard et al., 2007), however, it is difficult to reproduce the quality and the low cost production of barley beer with these grains.

The WHO standard definition for gluten-free foods adopted by the Codex *Alimentarius* in 2008 requires that food prepared from cereals such as wheat and barley must contain less than 20 mg/kg (20 ppm) gluten to be labeled "gluten-free". An accurate quantitative method to assess the gluten content of food and beverages using mass spectrometry was reported by Colgrave et al. (2012).

WO2009/021285 described the production of barley grain which was reduced in hordein content to less than 10% of the wild-type level, particularly in the hordeins B and C. However, there remains a need for grains with much lower levels of hordeins for the production of food and beverages that can be consumed by people with CD.

There is therefore a need for barley with substantially lower levels of CD-inducing hordeins which could be used in food and drink products for CD-susceptible subjects.

SUMMARY OF THE INVENTION

The present inventors have produced barley grain with very low levels of hordeins. This grain can be used for the production of a wide variety of foods and malt based beverages which can be consumed by subjects who suffer from coeliac disease.

In a first aspect, the present invention provides a method of producing a food or malt-based beverage ingredient, or a food or a malt-based beverage, the method comprising (i) processing barley grain to produce malt, wort, flour or wholemeal, and/or (ii) mixing barley grain, or malt, wort, flour or wholemeal produced from said grain, with at least one other food or beverage ingredient, wherein the barley grain, malt, wort, flour or wholemeal comprises about 50 ppm or less hordeins, thereby producing the food or malt-based beverage ingredient, food or malt-based beverage.

In an embodiment, the grain, malt, wort, flour or wholemeal comprises about 20 ppm or less, about 10 ppm or less, about 5 ppm or less, about 0.05 ppm to about 50 ppm, or about 0.05 ppm to about 20 ppm, about 0.05 ppm to about 10 ppm, about 0.05 ppm to about 5 ppm, about 0.1 ppm to about 5 ppm, about 3.9 ppm, or about 1.5 ppm, hordeins.

In another embodiment, the average weight of the grain is at least about 35 mg, at least about 39 mg, at least about 41 mg, at least about 47 mg, about 35 mg to about 60 mg, about 40 mg to about 60 mg, about 45 mg to about 60 mg, about 39.1 mg, about 41.8 mg or about 47.2 mg.

In a further embodiment, the grain, malt, wort, flour or wholemeal comprises 20 ppm or less hordeins, and the average weight of the grain is about 40 mg to about 60 mg. In another embodiment, the grain, malt, wort, flour or wholemeal comprises 20 ppm or less hordeins, and the average weight of the grain is about 45 mg to about 60 mg. The specific mention of these combinations does not exclude other combinations of these features.

In a further embodiment, at least about 80%, at least about 90%, at least about 95%, about 80% to about 98%, or about 80% to about 93%, of the grain do not pass through a 2.8 mm sieve.

In a further embodiment, the grain, malt, wort, flour or wholemeal comprises 20 ppm or less hordeins, the average weight of the grain is about 40 mg to about 60 mg, and at least about 80% of the grain do not pass through a 2.8 mm sieve. In another embodiment, the grain, malt, wort, flour or wholemeal comprises 20 ppm or less hordeins, the average weight of the grain is about 45 mg to about 60 mg, and at least about 80% of the grain do not pass through a 2.8 mm sieve. The specific mention of these combinations does not exclude other combinations of these features.

In yet a further embodiment, the grain is from a plant which has a harvest index of at least 40%, about 40% to about 60%, about 40% to about 55%, or about 40% to about 50%. In a preferred embodiment, the grain is from a plant which has a harvest index of about 40% to about 50%

In another embodiment, the grain has a length to thickness ratio of less than about 5, less than about 4, less than about 3.8, about 2 to about 5, or about 2.5 to about 3.8.

In a further embodiment, the flour or wholemeal produced from the grain comprises about 10 ppm or less, about 5 ppm or less, about 0.05 ppm to about 10 ppm, or about 0.05 ppm to about 5 ppm, about 3.9 ppm, or about 1.5 ppm, hordeins.

In an embodiment, the malt or wort produced from the grain comprises less than about 50 ppm, or less than about 20 ppm, hordeins.

In a further embodiment, the grain, or malt, wort, flour or wholemeal produced from said grain, has a level of less than 10%, less than 5% or less than 2% of a wild-type level, or is lacking, one or more than one or all of:

i) B-hordeins comprising a sequence of amino acids provided as SEQ ID NO:53, ii) B-hordeins comprising a sequence of amino acids provided as SEQ ID NO:54, iii) C-hordeins comprising a sequence of amino acids provided as SEQ ID NO:55, and iv) D-hordeins comprising a sequence of amino acids provided as SEQ ID NO:56, wherein each of the levels of less than 10%, less than 5% or less than 2% is relative to a wild-type barley grain, or malt, wort, flour or wholemeal produced from said grain, of the barley variety Bomi, Sloop, Baudin, Yagan, Hindmarsh, or Commander.

In an embodiment, the B-hordeins are at least B1-hordein (for example comprising an amino acid sequence provided as SEQ ID NO: 78) and B3-hordein (for example comprising an amino acid sequence provided as SEQ ID NO: 79). In a further example, the C-hordeins comprise an amino acid sequence provided as SEQ ID NO: 80. In yet another example, the D-hordeins comprise an amino acid sequence provided as SEQ ID NO: 76.

In an embodiment, the grain, or malt, wort, flour or wholemeal produced from said grain, further has a level of less than 10%, less than 5% or less than 2% of a wild-type level, or is further lacking;

i) γ-hordeins comprising a sequence of amino acids provided as SEQ ID NO: 57, and/or ii) avenin-like A proteins comprising a sequence of amino acids provided as SEQ ID NO: 52, wherein each of the levels of less than 10%, less than 5% or less than 2% is relative to a wild-type barley grain, or malt, wort, flour or wholemeal produced from said grain, of the barley variety Bomi, Sloop, Baudin, Yagan, Hindmarsh, or Commander. In an example, the γ-hordeins comprise an amino acid sequence provided as SEQ ID NO: 81. In yet another example, the avenin-like A proteins comprise an amino acid sequence provided as SEQ ID NO: 84.

Preferably in the above embodiment the γ-hordeins are γ1-hordeins and γ2-hordeins.

In an embodiment, the grain is homozygous for an allele of the Hor2 locus where most or all of the B-hordein encoding genes have been deleted, or wherein the malt, wort, flour or wholemeal produced from said grain comprises DNA which comprises the allele of the Hor2 locus where most or all of the B-hordein encoding genes have been deleted.

In another embodiment, the grain is homozygous for a null allele of the gene encoding D-hordein at the Hor3 locus, or wherein the malt, wort, flour or wholemeal produced from said grain comprises DNA which comprises the null allele of the gene encoding D-hordein, the null allele preferably comprising a stop codon, splice site mutation, frame-shift mutation, insertion, deletion or encoding a truncated D-hordein, or where most or all of the D-hordein encoding gene has been deleted.

In a further embodiment, the truncated D-hordein has a stop codon at the triplet encoding amino acid number 150.

In another embodiment, the grain is homozygous for an allele at the Lys3 locus of barley which results in the grain lacking C-hordeins, or wherein the malt, wort, flour or wholemeal produced from said grain comprises DNA which comprises the allele at the Lys3 locus.

In a further embodiment, the grain, malt, wort, flour or wholemeal comprises about 1% or less, about 0.01% or less, about 0.007% or less, about 0.0027% or less, about 0.001% to about 1%, about 0.001% to about 0.01%, about 0.007%, or about 0.0027%, of the level of hordeins when compared to grain from a corresponding wild-type barley plant or malt, wort, flour or wholemeal produced in the same manner from grain from a corresponding wild-type barley plant.

In yet another embodiment, the grain is from a plant which has at least 60%, at least 80%, at least 90%, about 60% to 100%, about 70% to 100%, about 80% to 100%, about 60%, about 70%, about 80%, or about 90% of the grain yield of the wild-type barley plant.

In another embodiment, the average weight of the grain is at least about 70%, at least about 80%, at least about 90%, at least about 95%, or about 100%, of grain of the wild-type barley plant.

In yet a further embodiment, the grain, or malt, wort, flour or wholemeal produced from said grain, comprises about 10% or less, about 5% or less, about 2% or less, about 0.1% to about 10%, or about 0.1% to about 10%, of one or more than one or all of the following when compared to the corresponding wild-type barley plant;
  i) B-hordeins comprising a sequence of amino acids provided as SEQ ID NO:53,
  ii) B-hordeins comprising a sequence of amino acids provided as SEQ ID NO:54,
  iii) C-hordeins comprising a sequence of amino acids provided as SEQ ID NO:55, and
  iv) D-hordeins comprising a sequence of amino acids provided as SEQ ID NO:56.

In another embodiment, the grain, or malt, wort, flour or wholemeal produced from said grain, further comprises about 10% or less, about 5% or less, about 1% or less, about 0.1% to about 10%, or about 0.1% to about 10%, of the following when compared to the corresponding wild-type barley plant;
  i) γ-hordeins comprising a sequence of amino acids provided as SEQ ID NO:57, and/or
  ii) avenin-like A proteins comprising a sequence of amino acids provided as SEQ ID NO:52.

In another embodiment, the grain, or malt, wort, flour or wholemeal produced from said grain, further comprises a γ3-hordein, in an amount about 60% or less when compared to the amount in the corresponding wild-type barley plant, the γ3-hordein comprising amino acids whose sequence is provided as SEQ ID NO:58, such as a γ3-hordein comprising amino acids whose sequence is provided as SEQ ID NO:83.

Examples of a wild-type barley plant include, but are not limited to, Bomi, Sloop, Baudin, Yagan, Hindmarsh, or Commander.

In another embodiment, the starch content of the grain is at least about 50% (w/w). More preferably, the starch content of the grain is about 50% to about 70% (w/w).

In a further embodiment, the coeliac toxicity of flour produced from the grain is less than about 5%, or less than about 1%, of flour produced from grain of a corresponding wild-type barley plant.

In a further embodiment, the average grain weight is at least 1.05 fold, at least 1.1 fold, or 1.05 to 1.3 fold, higher than a grain which is
  i) homozygous for an allele of the Hor2 locus where most or all of the B-hordein encoding genes have been deleted,
  ii) homozygous for an allele at the Lys3 locus of barley which results in the grain lacking C hordeins, and
  iii) homozygous for a wild type allele of D hordein encoding a full-length protein.

In yet a further embodiment, the grain is from a plant which has a grain yield which is least 1.20 fold, or at least 1.35 fold, or 1.2 to 1.5 fold, or 1.2 to 2.0 fold higher than the grain yield from a plant which is
  i) homozygous for an allele of the Hor2 locus where most or all of the B-hordein encoding genes have been deleted,
  ii) homozygous for an allele at the Lys3 locus of barley which results in the grain lacking C hordeins, and
  iii) homozygous for a wild type allele of D hordein encoding a full-length protein.

For example, with regard to the two above embodiments, the grain with the features defined in i) to iii) may be G1* grain described in WO 2009/021285.

In another embodiment, at least about 50%, at least about 60%, at least about 70%, at least about 80%, at least about 90%, or at least about 95%, of the genome of the barley grain is identical to the genome of a barley wild type cultivar such as, but not limited to, Sloop, Hindmarsh, Oxford or Maratime.

In an embodiment, the grain is from a non-transgenic plant.

In an alternate embodiment, the grain is from a transgenic plant.

In a further embodiment, the plant comprises a transgene which encodes a polynucleotide which down-regulates the production of at least one hordein in the grain. Preferably, the polynucleotide of this embodiment is an antisense polynucleotide, a sense polynucleotide, a catalytic polynucleotide, an artificial microRNA or a duplex RNA molecule which down-regulates expression of one or preferably more genes encoding hordeins.

In another embodiment, the method comprises producing flour or wholemeal from the grain.

In a further embodiment, the method comprises producing malt from the grain.

In an embodiment, the malt-based beverage is beer and the method comprises germinating the grain or cracked grain derived therefrom. In an embodiment, the method further comprises fractionating dried germinated grain into two or more of an endosperm fraction, an endothelial layer fraction, a husk fraction, an acrospire fraction, and a malt rootlets fraction; and combining and blending predetermined amounts of two or more of the fractions.

In an embodiment, at least about 50% of the grain germinates within 3 days following imbibition.

In a further embodiment, the food ingredient or malt-based beverage ingredient is flour, starch, malt, or wort, or wherein the food is leavened or unleavened breads, pasta, noodles, breakfast cereals, snack foods, cakes, pastries or foods containing flour-based sauces.

In an embodiment, the malt-based beverage is beer or whiskey.

In an embodiment, the food or malt-based beverage is for human consumption.

In a further embodiment, following consumption of the food or drink at least one symptom of coeliac's disease is not developed by a subject with said disease.

In another aspect, the present invention provides a barley plant which produces grain comprising about 50 ppm or less hordeins.

Also provided is grain of a barley plant of the invention.

Grain of the invention and/or grain of a barley plant of the invention may comprise one or more of the features defined above.

In an embodiment, the barley grain is capable of producing a barley plant of the invention In an embodiment, the grain has been processed so that it is unable to germinate. In an embodiment, the grain is hull-less.

In another aspect, the present invention provides a method of producing barley grain, the method comprising;
 a) growing a barley plant of the invention,
 b) harvesting the grain, and
 c) optionally processing the grain.

In an embodiment, the method comprises growing at least 10,000 plants in a field in an area of at least one hectare.

In another aspect, the present invention provides a method of producing flour, wholemeal, starch, malt, wort or other product obtained from grain, the method comprising;
 a) obtaining grain of the invention, and
 b) processing the grain to produce the flour, wholemeal, starch, malt, wort or other product.

Also provided is a product produced from a barley plant of the invention, or grain of the invention.

In one embodiment, the product is a food ingredient, malt-based beverage ingredient, food product or malt-based beverage product.

In an embodiment, the malt-based beverage product is beer or whiskey.

In a further embodiment, the product is a non-food product. Examples include, but are not limited to, films, coatings, adhesives, building materials and packaging materials.

Also provided is a food or malt-based beverage produced using a method of the invention.

In another aspect, provided is beer comprising one or more barley grain proteins and less than 0.9 ppm hordeins.

In an embodiment, the beer comprises at least about 2%, at least about 3%, at least about 4%, or at least about 5%, ethanol.

In another aspect, the present invention provides flour or wholemeal comprising one or more barley grain proteins and less than about 50 ppm, or less than about 20 ppm, hordeins.

In another aspect, the present invention provides malt or wort comprising one or more barley grain proteins and less than about 50 ppm, or less than about 20 ppm, hordeins.

In a further aspect, the present invention provides a method of identifying an allele of a barley D hordein gene which encodes a truncated D hordein, the method comprising
 i) obtaining a sample comprising nucleic acids from a barley plant, and
 ii) analysing the sample for the presence or absence of a guanine residue at position 450 of the open reading frame encoding D hordein, wherein the presence of the guanine indicates the D hordein gene encodes a truncated D hordein.

In an embodiment, step b) comprises amplifying genomic DNA using the primers GGCAATACGAGCAGCAAAC (SEQ ID NO: 66) and CCTCTGTCCTGGTTGTTGTC (SEQ ID NO: 67), or a variant of one or both thereof, and contacting products of the amplification with the restriction enzyme KpnI, wherein the absence of cleavage indicates the D hordein gene encodes a truncated D hordein.

In a further aspect, the present invention provides a method of avoiding or reducing the incidence or severity of coeliac's disease in a subject, the method comprising orally administering to the subject a food or malt-based beverage of the invention, or a grain of the invention, wherein the reduction of the incidence or severity of coeliac's disease is relative to when the subject is orally administered the same amount of a corresponding food or malt-based beverage made from wild-type barley grain.

Also provided is the use of a food or malt-based beverage of the invention, or a grain of the invention, for the manufacture of a food or beverage for orally administering to a subject to avoid or reduce the incidence or severity of coeliac's disease.

In a further aspect, the present invention provides a method for identifying barley grain which can be used to produce a food and/or malt-based beverage for consumption by a subject with coeliac's disease comprising
 a) obtaining one or more of the following materials;
  i) a sample from a plant capable of producing said grain,
  ii) the grain,
  iii) malt produced from the grain, and/or
  iv) an extract of said grain,
 b) analysing the material from step a) for the levels of B, C and D hordeins, peptides derived from B, C and D hordeins, and/or for alleles of B, C and D hordein genes,
 c) selecting grain which comprises about 50 ppm or less hordeins for producing a food and/or malt-based beverage for consumption by a subject with coeliac's disease.

In an embodiment, the material from step a) comprises genomic DNA and step b) comprises identifying the absence or presence of alleles of genes encoding one or more or all of;
 i) B-hordeins comprising a sequence of amino acids provided as SEQ ID NO:53,
 ii) B-hordeins comprising a sequence of amino acids provided as SEQ ID NO:54,
 iii) C-hordeins comprising a sequence of amino acids provided as SEQ ID NO:55, and
 iv) D-hordeins comprising a sequence of amino acids provided as SEQ ID NO:56,
wherein the absence of the alleles identifies grain which comprises about 50 ppm or less hordeins.

Any embodiment herein shall be taken to apply mutatis mutandis to any other embodiment unless specifically stated otherwise.

The present invention is not to be limited in scope by the specific embodiments described herein, which are intended for the purpose of exemplification only. Functionally-equivalent products, compositions and methods are clearly within the scope of the invention, as described herein.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

The invention is hereinafter described by way of the following non-limiting Examples and with reference to the accompanying figures.

BRIEF DESCRIPTION OF THE ACCOMPANYING DRAWINGS

FIG. 1. Schematic representation of barley chromosome 1.

Figure 2:
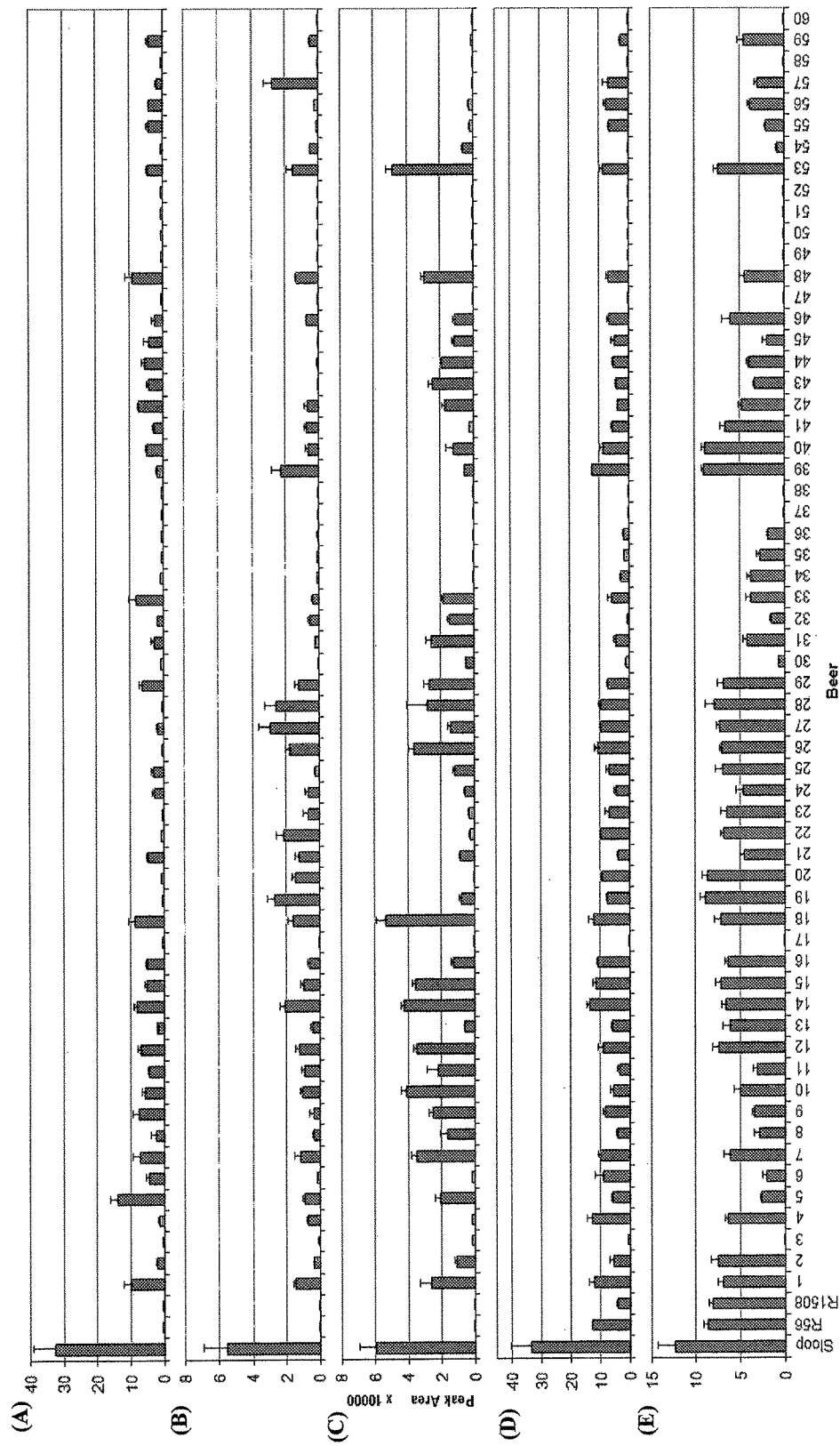

FIG. 2. Relative hordein quantitation in beers. The peak area of selected peptides representing the most abundant hordeins or related polypeptides detected in beer (A) QQCCQPLAQISEQAR (SEQ ID NO: 5) representing avenin-like A protein; (B) VFLQQQCSPVR (SEQ ID NO: 53) representing B1-hordein; (C) VFLQQQCSPVPMPQR (SEQ ID NO: 54) representing B3-hordein; (D) ELQESSLEACR (SEQ ID NO: 56) representing D-hordein; and (E) QQCCQQLANINEQSR (SEQ ID NO: 58) representing γ-hordein-3. These representative peptides were used to illustrate the relative amount of the major hordein proteins in wild-type (Sloop) and two hordein deletion beers made from Risø 56 and Risø 1508, respectively, and in 60 commercial beers. The small peak area seen for the gluten free beers 17, 47, 49-52, 54 was due to a low level of noise in the signal, and not due to detection of hordein.

FIG. 3. Comparison of D hordein amino acid sequences from Sloop (wild type) and Ethiopia R118 (null).

FIG. 4. Comparison of D hordein amino acid and coding nucleotides sequences from Sloop (wild type) and Ethiopia R118 (null). The position of the primers for the detection of each allele is shown along with the KpnI cleavage site only present in the wild type sequence.

Figure 5:
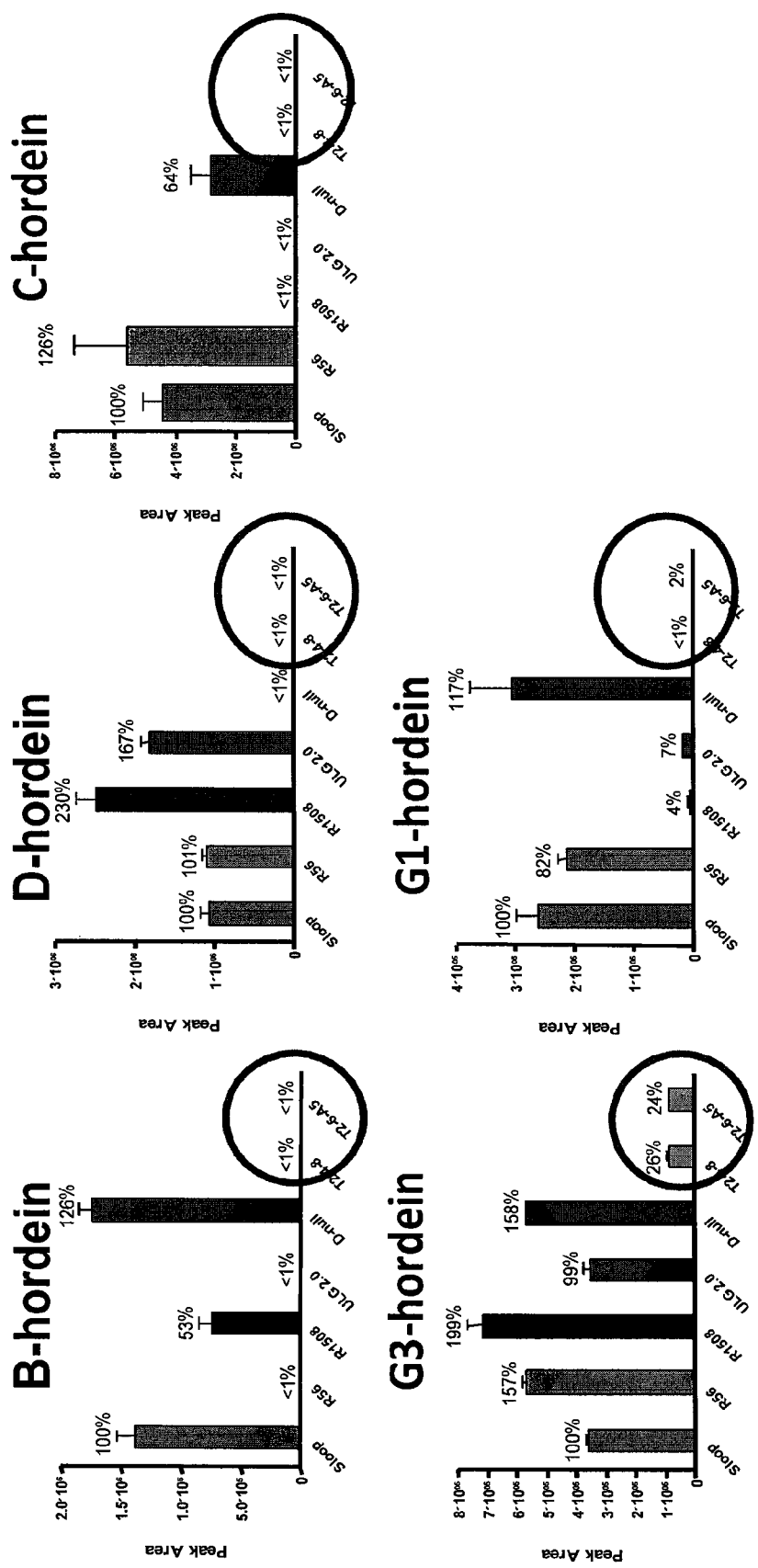

FIG. 5. Determination of hordein content of ULG3.0 lines by MRM MS by peak area, and indicating percentage relative to Sloop (100%).

Figure 6:
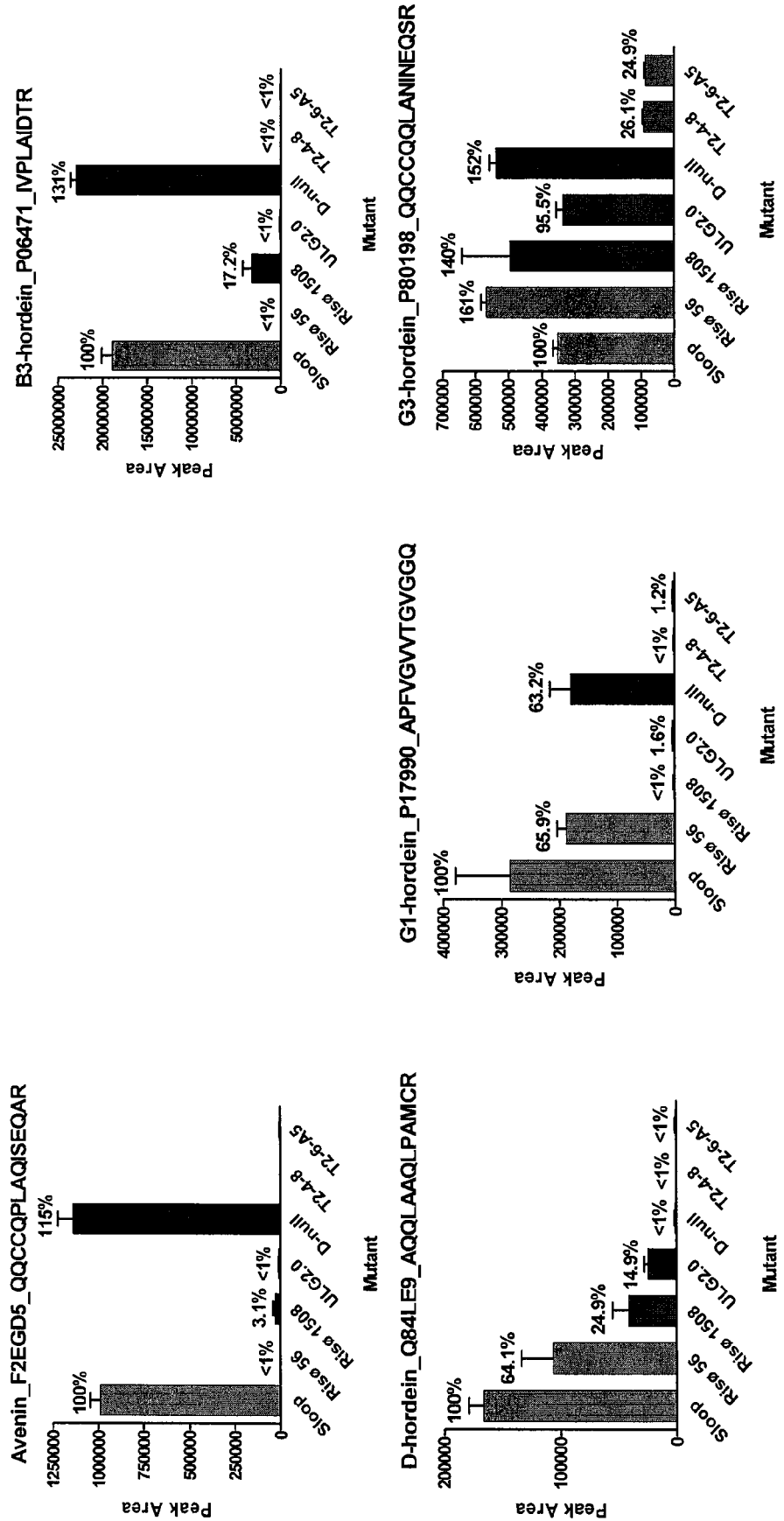

FIG. 6. Determination of hordein content of ULG3.0 lines by MRM MS by peak area, and indicating percentage relative to Sloop (100%).

Figure 7:
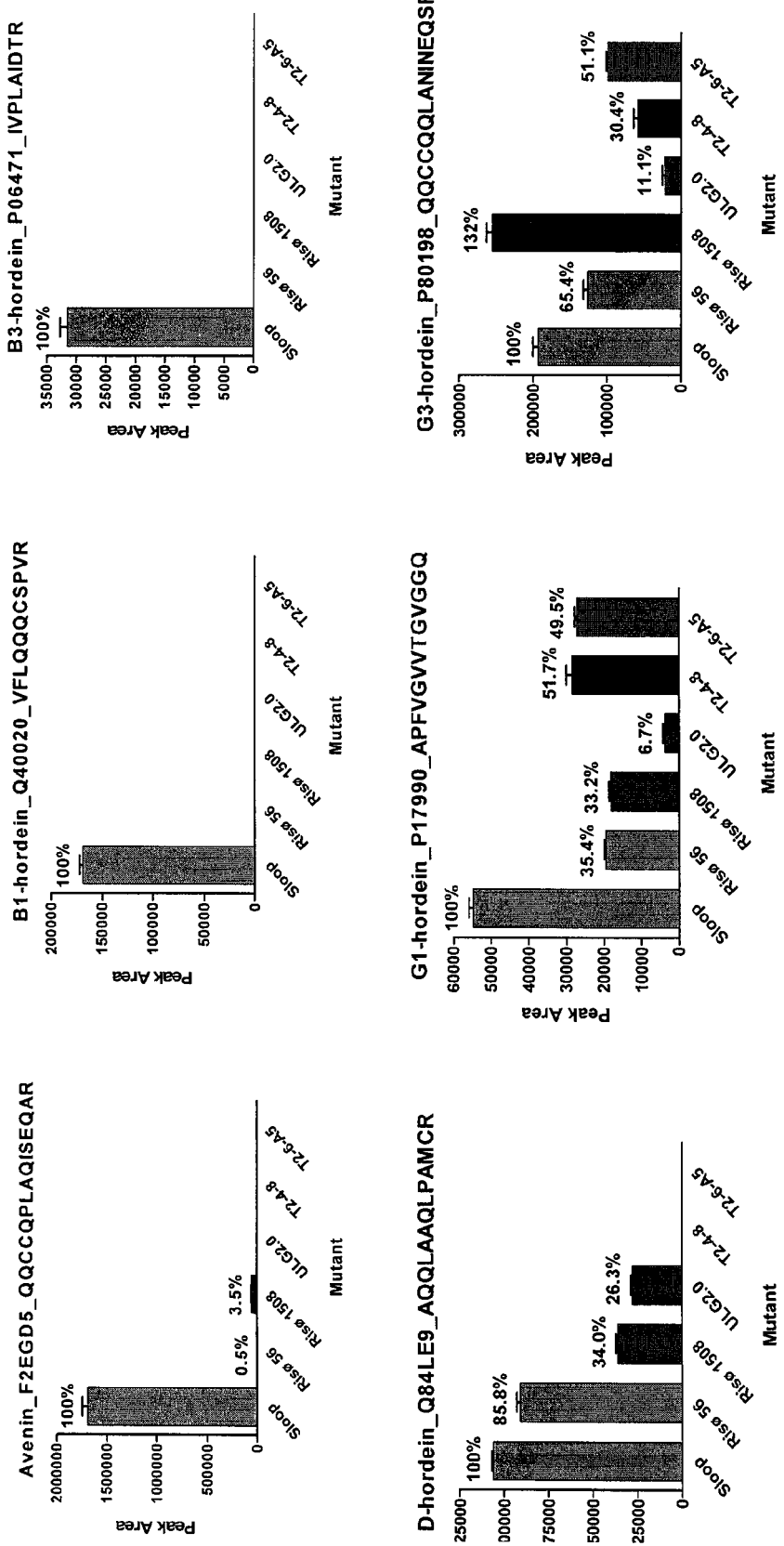

FIG. 7. Determination of hordein content of ULG3.0 beer by MRM MS as peak area for defined peptides. Peak areas are shown, and the percentage relative to Sloop (100%).

FIG. 8. Detection of hordeins and hordein-like proteins by MRM MS in flour from ULG3.0 (T2-4-8) and ULG3.2 candidate lines, compared to wild-type varieties Sloop, Baudin, Commander and Hindmarsh. Each graph shows the mean +/− SD for the summed peak area (3 MRM transitions) for a representative peptide from each hordein family. In each case the peptide (sequence as listed in graph) maps to either an avenin-like A protein, B1-, B3-, C-, D-, γ1- or γ3-hordein. The Uniprot accession number is given in the legend (e.g. F2EGD5 for first example).

KEY TO THE SEQUENCE LISTING

SEQ ID NOs: 1 and 4—Wheat α-gliadin peptides.

SEQ ID NOs 2, 3, 6 to 11, 16 to 59 and 85—Barley hordein peptides.

SEQ ID NO: 5—Wheat avenin-like A peptide.

SEQ ID NOs 12 to 15—Rye prolamin peptides.

SEQ ID NOs 60 to 71—Oligonucleotide primers.

SEQ ID NO: 72—Genomic region encoding barley cv. Sloop D-hordein.

SEQ ID NO: 73—Genomic region encoding barley cv. Ethiopia 8118 D-hordein (null).

SEQ ID NO: 74—Barley cv. Sloop D-hordein.

SEQ ID NO: 75—Barley cv. Ethiopia R1118 D-hordein.

SEQ ID NO: 74—Barley cv. Sloop D-hordein.

SEQ ID NO: 75—Barley cv. Ethiopia 8118 D-hordein.

SEQ ID NO: 76—Open reading frame encoding barley cv. Sloop D hordein.

SEQ ID NO: 77—Open reading frame encoding barley cv. Ethiopia R118 D hordein.

SEQ ID NO: 78—Example of wild type barley B1-hordein (Accession: Q40020).

SEQ ID NO: 79—Example of wild type barley B3-hordein (Accession: Q4G3S1).

SEQ ID NO: 80—Example of wild type barley C-hordein (Accession: Q40055).

SEQ ID NO: 81—Example of wild type barley γ1-hordein (Accession: P17990).

SEQ ID NO: 82—Example of wild type barley γ2-hordein (Accession: Q70IB4).

SEQ ID NO: 83—Example of wild type barley γ3-hordein (Accession: P80198).

SEQ ID NO: 84—Example of wild type barley avenin-like A protein (Accession: F2EGD5).

DETAILED DESCRIPTION OF THE INVENTION

General Techniques and Definitions

Unless specifically defined otherwise, all technical and scientific terms used herein shall be taken to have the same meaning as commonly understood by one of ordinary skill in the art (e.g., in plant breeding, food technology, cell culture, molecular genetics, immunology, protein chemistry, and biochemistry).

Unless otherwise indicated, the recombinant protein, cell culture, and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

A used herein, the term "barley" refers to any species of the Genus *Hordeum*, including progenitors thereof, as well as progeny thereof produced by crosses with other species. A preferred form of barley is the species *Hordeum vulgare*. The grains of most cultivars of barley grown commercially in the world today have covered (hulled) caryopses in which the so-called hull, which is the outer lemma and inner palea, is joined to the pericarp epidermis at maturity. Other cultivars, termed hull-less or naked barleys, are free threshing and the hulls are easily removed in the threshing process. Naked barley grains are preferred for human consumption, although hulled grain can be used after pearling, whereas hulled barley grain is preferred for the brewing industry and for animal feed. The hull-less grain trait is controlled by a single, recessive gene designated nud located on the long arm of chromosome 7H (Kikuchi et al., 2003).

Coeliac disease or celiac disease is an autoimmune disorder of the small intestine that occurs in genetically predisposed individuals in all age groups after early infancy. It affects approximately 1% of Indo-European populations, though it is significantly underdiagnosed. Coeliac disease is caused by a reaction to gliadin, a gluten protein found in wheat (and similar proteins of Triticeae which includes other cultivars such as barley and rye). Upon exposure to gliadin, the enzyme tissue transglutaminase modifies the protein, and the immune system cross-reacts with the bowel tissue, causing an inflammatory reaction. This leads to flattening of the lining of the small intestine, which interferes with the absorption of nutrients. The only effective treatment is a lifelong gluten-free diet. This condition has several other names, including: coeliac disease (with ligature), c(o)eliac sprue, non-tropical sprue, endemic sprue, gluten enteropathy or gluten-sensitive enteropathy, and gluten intolerance. The symptoms of coeliac disease vary widely from person to person. Symptoms of coeliac's disease may include one or more of the following; gas, recurring abdominal bloating and pain, chronic diarrhea, constipation, pale, foul-smelling, or fatty stool, weight loss/weight gain, fatigue, unexplained anemia (a low count of red blood cells causing fatigue), bone or joint pain, osteoporosis, osteopenia, behavioral changes, tingling numbness in the legs (from nerve damage), muscle cramps, seizures, missed menstrual periods (often because of excessive weight loss), infertility, recurrent miscarriage, delayed growth, failure to thrive in infants, pale sores inside the mouth, called aphthous ulcers, tooth discoloration or loss of enamel, and itchy skin rash called dermatitis herpetiformis. Some of the more common symptoms include; tiredness, intermittent diarrhoea, abdominal pain or cramping, indigestion, flatulence, bloating; and weight loss. Ceoliac's disease can be diagnosed, for example, as described in WO 01/025793.

As used herein, the term "null allele of the gene encoding D-hordein at the Hor3 locus" refers to any allele of this locus which does not encode a D-hordein protein, or if a protein is encoded it is not immunogenic to a subject with coeliac's disease (such as the truncated D-hordein provided in FIG. 3).

As used herein, the term "lacking" as used herein in the context of a recited substance means that the substance is absent from the barley grain, or a product derived therefrom, of the invention, or that the substance is not detected in the grain or product of the invention when assays for the substance are performed using a method known in the art. That is, the substance may be present at a level that is insufficient for detection, or within the standard error for the assay for that substance. For example, in the context of a recited hordein, the term "lacking" means that the specific hordein is not detected in an assay such as, for example, an MRM MS assay, an ELISA assay or a 2D-gel electrophoresis assay, such as exemplified herein. The substance that is lacking may be undetected in one type of assay or in multiple types of assays. It would be appreciated that the substance that is said to be lacking in the grain or product of the invention is present, as readily determined by an assay known in the art, in the corresponding wild-type grain or product.

As used herein, the term "hordeins", for example when used in the phrase "about 50 ppm or less hordeins" and similar phrases refers to total hordeins including B-, C-, D- and γ-hordeins.

The terms "seed" and "grain" are used interchangeably herein. "Grain" generally refers to mature, harvested grain but can also refer to grain after processing such as, for example, milling or polishing, where most of the grain stays intact, or after imbibition or germination, according to the context. Mature grain commonly has a moisture content of less than about 18-20%. Wild-type barley grain (whole grain) generally contains 9-12% protein, and about 30-50% of this is prolamin, typically 35%, so wild-type barley grain has about 3-4% prolamin by weight. Prolamins are found almost exclusively in the endosperm, which is about 70% of the wholegrain weight.

As used herein, the term "havest index" refers to the weight of the harvested grain as a percentage of the total weight of the plant.

As used herein, the term "corresponding wild-type" barley plant refers to a plant which comprises at least 50%, more preferably at least 75%, more preferably at least 95%, more preferably at least 97%, more preferably at least 99%, and even more preferably 99.5% of the genotype of a plant of the invention, but produces grain with unmodified hordein levels. In one embodiment, the "corresponding wild-type" barley plant is a cultivar used in plant breeding experiments to introduce genetic variants that result in reduced hordein production in the grain. In another embodiment, the "corresponding wild-type" barley plant is a parental cultivar into which a transgene has been introduced which reduces hordein production in the grain. In a further embodiment, the "corresponding wild-type" barley plant is a cultivar that is used at the date of filing for the commercial production of barley grain such as, but not limited to, Bomi, Sloop, Carlsberg II, K8, L1, Vlamingh, Stirling, Hamelin, Schooner, Baudin, Commander, Gairdner, Buloke, WI3586-1747, WI3416, Flagship, Cowabbie, Franklin, SloopSA, SloopVic, Quasar, VB9104, Grimmett, Cameo*Arupo 31-04, Prior, Schooner, Unicorn, Harrington, Torrens, Galleon, Morex, Dhow, Capstan, Fleet, Keel, Maritime, Yarra, Dash, Doolup, Fitzgerald, Molloy, Mundah, Oxford, Onslow, Skiff, Unicorn, Yagan, Chebec, Hindmarsh, Chariot, Diamant, Korai, Rubin, Bonus, Zenit, Akcent, Forum, Amulet, Tolar, Heris, Maresi, Landora, Caruso, Miralix, Wikingett Brise, Caruso, Potter, Pasadena, Annabell, Maud, Extract, Saloon, Prestige, Astoria, Elo, Cork, Extract, Laura. In an embodiment, the "corresponding wild-type" barley plant produces grain with unmodified hordein levels due to it comprising a full complement of functional hordein genes encoding functional hordein proteins, including the B, C, D and γ-hordeins encoded by the Hor2, Hor1, Hor3, and Hor5 loci.

As used herein, the term "one or more barley grain proteins" refers to naturally occurring proteins produced by barley grain other than hordeins. Examples of such proteins are known to those skilled in the art. Specific examples include, but are not limited to, barley albumins such as the 9 kDa lipid transfer protein 1 (LTP1) (see Douliez et al. (2000) for a review and Swiss-prot Accession No. P07597 as an example), the α-amylase trypsin inhibitors (CMd, CMb, CMa), protein Z (see Brandt et al. (1990) and Genbank Accession No. P06293), and proteins identified in Colgrave et al. (2012), including processed (mature) forms thereof, as well as denatured forms and/or fragments thereof produced as a result of the production of malt, flour, wholemeal, food or malt-based beverage of the invention.

As used herein, "average weight of the grain" is preferably determined by obtaining at least 25, at least 50 or at least 100, more preferably about 100, individual grains from a plant (or genetically identical plants grown under the same conditions) and determining the average weight of the grain.

As used herein, the term "malt" is used to refer to barley malt, "flour" to refer to barley flour, "wholemeal" to refer to barley wholemeal, and "beer" to refer to beer which is produced using barley as its main ingredient providing fermentable carbohydrate, except where the malt, flour, wholemeal or beer is explicitly stated to come from a source other than barley. As used herein, "wort" refers to the liquid extracted from the mashing process during the brewing of beer or whisky. Wort contains the sugars that will be fermented by the brewing yeast to produce alcohol. More specifically, a source of malt, wort, flour, beer, wholemeal, food product etc of the invention is from the processing (for example, milling and/or fermentation) of barley grain. The grain, malt, wort, flour, wholemeal or beer of the invention may be mixed or blended with grain, malt, wort, flour, wholemeal or beer which is not derived from barley. These terms include malt, wort, flour, beer, wholemeal, food product etc produced from a mixture of grains including barley. In a preferred embodiment, at least 10% or at least 50% of the grain used to produce the malt, wort, flour, beer, wholemeal, food product etc is barley grain.

The term "plant" as used herein as a noun refers to a whole plant such as, for example, a plant growing in a field for commercial barley production. A "plant part" refers to plant vegetative structures (for example, leaves, stems), roots, floral organs/structures, seed (including embryo, endosperm, and seed coat), plant tissue (for example, vascular tissue, ground tissue, and the like), cells, starch granules or progeny of the same.

A "transgenic plant", "genetically modified plant" or variations thereof refers to a plant that contains a gene construct ("transgene") not found in a wild-type plant of the same species, variety or cultivar. A "transgene" as referred to herein has the normal meaning in the art of biotechnology and includes a genetic sequence which has been produced or altered by recombinant DNA or RNA technology and which has been introduced into the plant cell. The transgene may include genetic sequences derived from a plant cell. Typically, the transgene has been introduced into the plant by human manipulation such as, for example, by transformation but any method can be used as one of skill in the art recognizes.

"Nucleic acid molecule" refers to a polynucleotide such as, for example, DNA, RNA or oligonucleotides. It may be DNA or RNA of genomic or synthetic origin, double-stranded or single-stranded, and combined with carbohydrate, lipids, protein, or other materials to perform a particular activity defined herein.

"Operably linked" as used herein refers to a functional relationship between two or more nucleic acid (e.g., DNA) segments. Typically, it refers to the functional relationship of transcriptional regulatory element (promoter) to a transcribed sequence. For example, a promoter is operably linked to a coding sequence, such as a polynucleotide defined herein, if it stimulates or modulates the transcription of the coding sequence in an appropriate cell. Generally, promoter transcriptional regulatory elements that are operably linked to a transcribed sequence are physically contiguous to the transcribed sequence, i.e., they are cis-acting. However, some transcriptional regulatory elements, such as enhancers, need not be physically contiguous or located in close proximity to the coding sequences whose transcription they enhance.

As used herein, the term "gene" is to be taken in its broadest context and includes the deoxyribonucleotide sequences comprising the protein coding region of a structural gene and including sequences located adjacent to the coding region on both the 5' and 3' ends for a distance of at least about 2 kb on either end and which are involved in expression of the gene. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region which may be interrupted with non-coding sequences termed "introns" or "intervening regions" or "intervening sequences." Introns are segments of a gene which are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide. The term "gene" includes a synthetic or fusion molecule encoding all or part of the proteins of the invention described herein and a complementary nucleotide sequence to any one of the above.

As used herein, the term "other food or beverage ingredient" refers to any substance suitable for consumption by an animal, preferably any substance suitable for consumption by a human, when provided as part of a food or beverage. Examples include, but are not limited to, grain from other plant species, sugar, etc, but excluding water.

Plants of the invention typically have one or more genetic variations which each result in reduced levels of at least one hordein, more preferably at least B, C and D-hordeins. As used herein, the term "genetic variation which each results in reduced levels of at least one hordein" refers to any polymorphism of a barley plant that reduces hordein production. The genetic variation may comprise, for example, a deletion of a hordein gene(s) or part thereof, or a mutation which reduce barley gene transcription. Examples of such genetic variations are present in Risø 56, Risø 527 and Risø 1508 and Ethiopia R118. Hence, such plants may be used as parental plants to produce the plants of the invention. A plant of the invention may result from the progeny from a cross between any of these barley mutants. In a preferred embodiment, a plant of the invention is not the progeny from a cross between Risø 56 and Risø 1508 comprising the hor2 and lys3 mutations present in these lines and which is wild-type for the gene encoding D-hordein. In an embodiment, the plant encodes γ3-hordein comprising amino acids whose sequence is provided as SEQ ID NO:58, such as a γ3-hordein comprising amino acids whose sequence is provided as SEQ ID NO:83. For instance, the plant may have a functional wild type γ3-hordein gene such as the γ3-hordein gene of barley cultivar Bomi, Sloop, Baudin, Yagan, Hindmarsh, or Commander. In an embodiment, the plant is not the progeny from a cross between Risø 527 and Rise 1508.

As used herein, unless stated to the contrary, the phrase "about" refers to any reasonable range in light of the value in question. In a preferred embodiment, the term "about" refers to +/−10%, more preferably +/−5%, more preferably +/−1%, the specified value.

Unless specified otherwise, when referring to weight and a percentage, the units are w/w.

The term "and/or", e.g., "X and/or Y" shall be understood to mean either "X and Y" or "X or Y" and shall be taken to provide explicit support for both meanings or for either meaning.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Prolamins and Hordeins

Cereal prolamins (known as gliadins in wheat, hordeins in barley, secalins in rye, avenins in oats, and zeins in maize) are the main endosperm storage proteins in all cereal grains, with the exception of oats and rice (Shewry and Halford, 2002). Hordeins represent 35-50% of the total protein in barley seeds (Jaradat, 1991). They are classified into four groups, A (also known as γ hordein), B, C, and D, in order of decreasing mobility (Field et al., 1982). B, C, D and γ-hordeins are encoded by the Hor2, Hor1, Hor3, and Hor5 loci, respectively, on chromosome 1H which is schematically represented in FIG. 1.

The B hordeins are the main protein fraction, differing from C hordeins in their sulphur content (Kreis and Shewry, 1989). B hordeins account for 70-80% of the total and C hordeins for 10-20% (Davies et al., 1993). The A hordeins are not generally considered to be a storage fraction whereas D hordeins are homologous to the high-molecular-weight glutenins. Hordeins, along with the rest of the related cereal prolamins, are not expressed in the zygotic embryo itself, unlike other storage proteins such as napins; they are believed to be expressed exclusively in the starchy endosperm during the middle-to-late stages of seed development.

Examples of barley hordein amino acid sequences and genes encoding them are provided in WO 2009/021285.

A malt-based beverage provided by the present invention involves alcohol beverages (including distilled beverages) and non-alcohol beverages that are produced by using malt as a part or whole of their starting material. Examples include beer, happoshu (low-malt beer beverage), whisky, low-alcohol malt-based beverages (e.g., malt-based beverages containing less than 1% of alcohols), and non-alcohol beverages.

Malting is a process of controlled steeping and germination followed by drying of the barley grain. This sequence of events is important for the synthesis of numerous enzymes that cause grain modification, a process that principally depolymerizes the dead endosperm cell walls and mobilizes the grain nutrients. In the subsequent drying process, flavour and colour are produced due to chemical browning reactions. Although the primary use of malt is for beverage production, it can also be utilized in other industrial processes, for example as an enzyme source in the baking industry, or as a flavouring and colouring agent in the food industry, for example as malt or as a malt flour, or indirectly as a malt syrup, etc.

In one embodiment, the present invention relates to methods of producing a malt composition. The method preferably comprises the steps of:

(i) providing grain of a barley plant of the invention,
(ii) steeping said grain,
(iii) germinating the steeped grains under predetermined conditions and
(iv) drying said germinated grains.

For example, the malt may be produced by any of the methods described in Hoseney (Principles of Cereal Science and Technology, Second Edition, 1994: American Association of Cereal Chemists, St. Paul, Minn.). However, any other suitable method for producing malt may also be used with the present invention, such as methods for production of speciality malts, including, but limited to, methods of roasting the malt. One non-limiting example is described in Example 6.

Malt may be prepared using only grain produced from barley plants of the invention or in mixtures comprising other grains.

Malt is mainly used for brewing beer, but also for the production of distilled spirits. Brewing comprises wort production, main and secondary fermentations and post-treatment. First the malt is milled, stirred into water and heated. During this "mashing", the enzymes activated in the malting degrade the starch of the kernel into fermentable sugars. The produced wort is clarified, yeast is added, the mixture is fermented and a post-treatment is performed.

In another embodiment, wort compositions can be prepared from the malt. Said wort may be first and/or second and/or further wort. In general a wort composition will have a high content of amino nitrogen and fermentable carbohydrates, mainly maltose. Typically, wort is prepared by incubating malt with water, i.e. by mashing. During mashing, the malt/water composition may be supplemented with additional carbohydrate-rich compositions, for example barley, maize or rice adjuncts. Unmalted cereal adjuncts usually contain no active enzymes, and therefore rely on malt or exogenous enzymes to provide enzymes necessary for sugar conversion.

In general, the first step in the wort production process is the milling of malt in order that water may gain access to grain particles in the mashing phase, which is fundamentally an extension of the malting process with enzymatic depolymerization of substrates. During mashing, milled malt is incubated with a liquid fraction such as water. The temperature is either kept constant (isothermal mashing) or gradually increased. In either case, soluble substances produced in malting and mashing are extracted into said liquid fraction before it is separated by filtration into wort and residual solid particles denoted spent grains. This wort may also be denoted first wort. After filtration, a second wort is obtained. Further worts may be prepared by repeating the procedure. Non-limiting examples of suitable procedures for preparation of wort is described in Hoseney (supra).

The wort composition may also be prepared by incubating barley plants of the invention or parts thereof with one or more suitable enzyme, such as enzyme compositions or enzyme mixture compositions, for example Ultraflo or Cereflo (Novozymes). The wort composition may also be prepared using a mixture of malt and unmalted barley plants or parts thereof, optionally adding one or more suitable enzymes during said preparation. In addition, prolyl-endopeptidase enzymes which specifically destroy the toxic amino linkages involved in coeliac disease could be added during the fermentation of the wort to reduce the toxicity of the residual hordeins (De Angelis et al., 2007; Marti et al., 2005; Stepniak et al., 2006).

Grain Processing

Barley grain of the invention can be processed to produce a food ingredient, beverage ingredient, food or beverage, or non-food product using any technique known in the art.

In one embodiment, the product is whole grain flour (an ultrafine-milled whole grain flour, such as an ultrafine-milled whole grain flour; a whole grain flour, or a flour made from about 100% of the grain). The whole grain flour includes a refined flour constituent (refined flour or refined flour) and a coarse fraction (an ultrafine-milled coarse fraction).

Refined flour may be flour which is prepared, for example, by grinding and bolting cleaned barley. The Food and Drug Administration (FDA) requires flour to meet certain particle size standards in order to be included in the category of refined barley flour. The particle size of refined flour is described as flour in which not less than 98% passes through a cloth having openings not larger than those of woven wire cloth designated "212 micrometers (U.S. Wire 70)".

The coarse fraction includes at least one of: bran and germ. For instance, the germ is an embryonic plant found within the barley kernel. The germ includes lipids, fiber, vitamins, protein, minerals and phytonutrients, such as flavonoids. The bran includes several cell layers and has a significant amount of lipids, fiber, vitamins, protein, minerals and phytonutrients, such as flavonoids. Further, the coarse fraction may include an aleurone layer which also includes lipids, fiber, vitamins, protein, minerals and phytonutrients, such as flavonoids. The aleurone layer, while technically considered part of the endosperm, exhibits many of the same characteristics as the bran and therefore is typically removed with the bran and germ during the milling process. The aleurone layer contains proteins, vitamins and phytonutrients, such as ferulic acid.

Further, the coarse fraction may be blended with the refined flour constituent. Preferably, the coarse fraction is homogenously blended with the refined flour constituent. Homogenously blending the coarse fraction and refined flour constituent may help reduce stratification of the particles by size during shipping. The coarse fraction may be mixed with the refined flour constituent to form the whole grain flour, thus providing a whole grain flour with increased nutritional value, fiber content, and antioxidant capacity as compared to refined flour. For example, the coarse fraction or whole grain flour may be used in various amounts to replace refined or whole grain flour in baked goods, snack products, and food products. The whole grain flour of the present invention (i.e.-ultrafine-milled whole grain flour) may also be marketed directly to consumers for use in their homemade baked products. In an exemplary embodiment, a granulation profile of the whole grain flour is such that 98% of particles by weight of the whole grain flour are less than 212 micrometers.

In further embodiments, enzymes found within the bran and germ of the whole grain flour and/or coarse fraction are inactivated in order to stabilize the whole grain flour and/or coarse fraction. It is contemplated by the present invention that inactivated may also mean inhibited, denatured, or the like. Stabilization is a process that uses steam, heat, radiation, or other treatments to inactivate the enzymes found in the bran and germ layer. Naturally occurring enzymes in the bran and germ will catalyze changes to compounds in the flour, adversely affecting the cooking characteristics of the flour and the shelf life. Inactivated enzymes do not catalyze changes to compounds found in the flour, therefore, flour that has been stabilized retains its cooking characteristics and has a longer shelf life. For example, the present invention may implement a two-stream milling technique to grind the coarse fraction. Once the coarse fraction is separated and stabilized, the coarse fraction is then ground through a grinder, preferably a gap mill, to form a coarse fraction having a particle size distribution less than or equal to about 500 micrometers. In an exemplary embodiment, the gap mill tip speed normally operates between 115 m/s to 144 m/s, the high tip speed generates heat. The heat generated during the process and the airflow lead to a decrease in the microbial load of the coarse fraction. In further embodiments, prior to grinding in a gap mill, the coarse fraction may have an average aerobic plate count of 95,000 colony forming units/gram (cfu/g) and an average coliform count of 1,200 cfu/g. After passing through the gap mill the coarse fraction may have an average aerobic plate count of 10,000 cfu/g and an average coliform count of 900 cfu/g. Thus, the microbial load may be noticeably decreased in the coarse fraction of the present invention. After sifting, any ground coarse fraction having a particle size greater than 500 micrometers may be returned to the process for further milling.

In additional embodiments, the whole grain flour or the coarse fraction may be a component of a food product. For example, the food product may be a bagel, a biscuit, a bread, a bun, a croissant, a dumpling, an English muffin, a muffin, a pita bread, a quickbread, a refrigerated/frozen dough products, dough, baked beans, a burrito, chili, a taco, a tamale, a tortilla, a pot pie, a ready to eat cereal, a ready to eat meal, stuffing, a microwaveable meal, a brownie, a cake, a cheesecake, a coffee cake, a cookie, a dessert, a pastry, a sweet roll, a candy bar, a pie crust, pie filling, baby food, a baking mix, a batter, a breading, a gravy mix, a meat extender, a meat substitute, a seasoning mix, a soup mix, a gravy, a roux, a salad dressing, a soup, sour cream, a noodle, a pasta, ramen noodles, chow mein noodles, lo mein noodles, an ice cream inclusion, an ice cream bar, an ice cream cone, an ice cream sandwich, a cracker, a crouton, a doughnut, an egg roll, an extruded snack, a fruit and grain bar, a microwaveable snack product, a nutritional bar, a pancake, a par-baked bakery product, a pretzel, a pudding, a granola-based product, a snack chip, a snack food, a snack mix, a waffle, a pizza crust, animal food or pet food.

In alternative embodiments, the whole grain flour or coarse fraction may be a component of a nutritional supplement. For instance, the nutritional supplement may be a product that is added to the diet containing one or more ingredients, typically including: vitamins, minerals, herbs, amino acids, enzymes, antioxidants, herbs, spices, probiotics, extracts, prebiotics and fiber. The whole grain flour or coarse fraction of the present invention includes vitamins, minerals, amino acids, enzymes, and fiber. For instance, the coarse fraction contains a concentrated amount of dietary fiber as well as other essential nutrients, such as B-vitamins, selenium, chromium, manganese, magnesium, and antioxidants, which are essential for a healthy diet. For example 22 grams of the coarse fraction of the present invention delivers 33% of an individual's daily recommend consumption of fiber. Further, 14 grams is all that is needed to deliver 20% of an individuals daily recommend consumption of fiber. Thus, the coarse fraction is an excellent supplemental source for consumption of an individual's fiber requirement. Therefore, in a present embodiment, the whole grain flour or coarse fraction may be a component of a nutritional supplement. The nutritional supplement may include any known nutritional ingredients that will aid in the overall health of an individual, examples include but are not limited to vitamins, minerals, other fiber components, fatty acids, antioxidants, amino acids, peptides, proteins, lutein, ribose, omega-3 fatty acids, and/or other nutritional ingredients.

In additional embodiments, the whole grain flour or coarse fraction may be a fiber supplement or a component thereof. Many current fiber supplements such as *psyllium* husks, cellulose derivatives, and hydrolyzed guar gum have limited nutritional value beyond their fiber content. Additionally, many fiber supplements have a undesirable texture and poor taste. Fiber supplements made from the whole grain flour or coarse fraction may help deliver fiber as well as protein, and antioxidants. The fiber supplement may be delivered in, but is not limited to the following forms: instant beverage mixes, ready-to-drink beverages, nutritional bars, wafers, cookies, crackers, gel shots, capsules, chews, chewable tablets, and pills. One embodiment delivers the fiber supplement in the form of a flavored shake or malt type beverage, this embodiment may be particularly attractive as a fiber supplement for children.

In an additional embodiment, a milling process may be used to make a multi-grain flour, multi-barley flour, or a multi-grain coarse fraction. For example, bran and germ from one type of barley may be ground and blended with ground endosperm or whole grain barley flour of another type of barley. Alternatively bran and germ of one type of grain may be ground and blended with ground endosperm or whole grain flour of another type of grain. In an additional embodiment, bran and germ from a first type of barley or grain may be blended with bran and germ from a second type of barley or grain to produce a multi-grain coarse fraction. It is contemplated that the present invention encompasses mixing any combination of one or more of bran, germ, endosperm, and whole grain flour of one or more grains. This multi-grain, multi-barley approach may be used to make custom flour and capitalize on the qualities and nutritional contents of multiple types of grains or barleys to make one flour.

The whole grain flour of the present invention may be produced via a variety of milling processes. An exemplary embodiment involves grinding grain in a single stream without separating endosperm, bran, and germ of the grain into separate streams. Clean and tempered grain is conveyed to a first passage grinder, such as a hammermill, roller mill, pin mill, impact mill, disc mill, air attrition mill, gap mill, or the like. In one embodiment, the grinder may be a gap mill. After grinding, the grain is discharged and conveyed to a sifter. Any sifter known in the art for sifting a ground particle may be used. Material passing through the screen of the sifter is the whole grain flour of the present invention and requires no further processing. Material that remains on the screen is referred to as a second fraction. The second fraction requires additional particle reduction. Thus, this second fraction may be conveyed to a second passage grinder. After grinding, the second fraction may be conveyed to a second sifter. Material passing through the screen of the second sifter is the whole grain flour of the present invention. The material that remains on the screen is referred to as the fourth fraction and requires further processing to reduce the particle size. The fourth fraction on the screen of the second sifter is conveyed back into either the first passage grinder or the second passage grinder for further processing via a feedback loop. In an alternative embodiment of the invention, the process may include a plurality of first pass grinders to provide a higher system capacity.

It is contemplated that the whole grain flour, coarse fraction and/or grain products of the present invention may be produced by any milling process known in the art. Further, it is contemplated that the whole grain flour, coarse fraction and/or grain products of the present invention may be modified or enhanced by way of numerous other processes such as: fermentation, instantizing, extrusion, encapsulation, toasting, roasting, or the like.

Polynucleotides which Down-Regulate the Production of a Hordein

In one embodiment, grain of the invention, and/or used in the methods of the invention, is from a transgenic barley plant which comprises a transgene which encodes a polynucleotide which down-regulates the production of at least one hordein in the grain. Examples of such polynucleotides include, but are not limited to, antisense polynucleotide, a sense polynucleotide, a catalytic polynucleotide, an artificial microRNA or a duplex RNA molecule. When present in the grain, each of these polynucleotides result in a reduction in hordein mRNA available for translation.

Antisense Polynucleotides

The term "antisense polynucletoide" shall be taken to mean a DNA or RNA, or combination thereof, molecule that is complementary to at least a portion of a specific mRNA molecule encoding a hordein and capable of interfering with a post-transcriptional event such as mRNA translation. The use of antisense methods is well known in the art (see for example, G. Hartmann and S. Endres, Manual of Antisense Methodology, Kluwer (1999)). The use of antisense techniques in plants has been reviewed by Bourque (1995) and Senior (1998). Senior (1998) states that antisense methods are now a very well established technique for manipulating gene expression.

An antisense polynucleotide in a barley plant of the invention will hybridize to a target polynucleotide under physiological conditions. As used herein, the term "an antisense polynucleotide which hybridises under physiological conditions" means that the polynucleotide (which is fully or partially single stranded) is at least capable of forming a double stranded polynucleotide with mRNA encoding a protein, such as a barley hordein under normal conditions in a barley cell.

Antisense molecules may include sequences that correspond to the structural genes or for sequences that effect control over the gene expression or splicing event. For example, the antisense sequence may correspond to the targeted coding region of the genes of the invention, or the 5'-untranslated region (UTR) or the 3'-UTR or combination of these. It may be complementary in part to intron sequences, which may be spliced out during or after transcription, preferably only to exon sequences of the target gene. In view of the generally greater divergence of the UTRs, targeting these regions provides greater specificity of gene inhibition.

The length of the antisense sequence should be at least 19 contiguous nucleotides, preferably at least 50 nucleotides, and more preferably at least 100, 200, 500 or 1000 nucleotides. The full-length sequence complementary to the entire gene transcript may be used. The length is most preferably 100-2000 nucleotides. The degree of identity of the antisense sequence to the targeted transcript should be at least 90% and more preferably 95-100%. The antisense RNA molecule may of course comprise unrelated sequences which may function to stabilize the molecule.

Catalytic Polynucleotides

The term catalytic polynucleotide/nucleic acid refers to a DNA molecule or DNA-containing molecule (also known in the art as a "deoxyribozyme") or an RNA or RNA-containing molecule (also known as a "ribozyme") which specifically recognizes a distinct substrate and catalyzes the chemical modification of this substrate. The nucleic acid bases in the catalytic nucleic acid can be bases A, C, G, T (and U for RNA).

Typically, the catalytic nucleic acid contains an antisense sequence for specific recognition of a target nucleic acid, and a nucleic acid cleaving enzymatic activity (also referred to herein as the "catalytic domain"). The types of ribozymes that are particularly useful in this invention are the hammerhead ribozyme (Haseloff and Gerlach, 1988, Perriman et al., 1992) and the hairpin ribozyme (Shippy et al., 1999).

The ribozymes in barley plants of the invention and DNA encoding the ribozymes can be chemically synthesized using methods well known in the art. The ribozymes can also be prepared from a DNA molecule (that upon transcription, yields an RNA molecule) operably linked to an RNA polymerase promoter, e.g., the promoter for T7 RNA polymerase or SP6 RNA polymerase. When the vector also contains an RNA polymerase promoter operably linked to the DNA molecule, the ribozyme can be produced in vitro upon incubation with RNA polymerase and nucleotides. In a separate embodiment, the DNA can be inserted into an expression cassette or transcription cassette. After synthesis, the RNA molecule can be modified by ligation to a DNA molecule having the ability to stabilize the ribozyme and make it resistant to RNase.

As with antisense polynucleotides described herein, the catalytic polynucleotides should also be capable of hybridizing a target nucleic acid molecule (for example an mRNA encoding a barley hordein) under "physiological conditions", namely those conditions within a barley cell.

RNA Interference

RNA interference (RNAi) is particularly useful for specifically inhibiting the production of a particular protein. Although not wishing to be limited by theory, Waterhouse et al. (1998) have provided a model for the mechanism by which dsRNA (duplex RNA) can be used to reduce protein production. This technology relies on the presence of dsRNA molecules that contain a sequence that is essentially identical to the mRNA of the gene of interest or part thereof, in this case an mRNA encoding a polypeptide according to the invention. Conveniently, the dsRNA can be produced from a single promoter in a recombinant vector or host cell, where the sense and antisense sequences are flanked by an unrelated sequence which enables the sense and antisense sequences to hybridize to form the dsRNA molecule with the unrelated sequence forming a loop structure. The design and production of suitable dsRNA molecules for the present invention is well within the capacity of a person skilled in the art, particularly considering Waterhouse et al. (1998), Smith et al. (2000), WO 99/32619, WO 99/53050, WO 99/49029, and WO 01/34815.

In one example, a DNA is introduced that directs the synthesis of an at least partly double stranded (duplex) RNA product(s) with homology to the target gene to be inactivated. The DNA therefore comprises both sense and antisense sequences that, when transcribed into RNA, can hybridize to form the double-stranded RNA region. In a preferred embodiment, the sense and antisense sequences are separated by a spacer region that comprises an intron which, when transcribed into RNA, is spliced out. This arrangement has been shown to result in a higher efficiency of gene silencing. The double-stranded region may comprise one or two RNA molecules, transcribed from either one DNA region or two. The presence of the double stranded molecule is thought to trigger a response from an endogenous plant system that destroys both the double stranded RNA and also the homologous RNA transcript from the target plant gene, efficiently reducing or eliminating the activity of the target gene.

The length of the sense and antisense sequences that hybridise should each be at least 19 contiguous nucleotides, preferably at least 30 or 50 nucleotides, and more preferably at least 100, 200, 500 or 1000 nucleotides. The full-length sequence corresponding to the entire gene transcript may be used. The lengths are most preferably 100-2000 nucleotides. The degree of identity of the sense and antisense sequences to the targeted transcript should be at least 85%, preferably at least 90% and more preferably 95-100%. The RNA molecule may of course comprise unrelated sequences which may function to stabilize the molecule. The RNA molecule may be expressed under the control of a RNA polymerase II or RNA polymerase III promoter. Examples of the latter include tRNA or snRNA promoters.

Preferred small interfering RNA ("siRNA") molecules comprise a nucleotide sequence that is identical to about 19-21 contiguous nucleotides of the target mRNA. Preferably, the target mRNA sequence commences with the dinucleotide AA, comprises a GC-content of about 30-70% (preferably, 30-60%, more preferably 40-60% and more preferably about 45%-55%), and does not have a high percentage identity to any nucleotide sequence other than the target in the genome of the barley plant in which it is to be introduced, e.g., as determined by standard BLAST search.

microRNA

MicroRNA regulation is a clearly specialized branch of the RNA silencing pathway that evolved towards gene regulation, diverging from conventional RNAi/PTGS. MicroRNAs are a specific class of small RNAs that are encoded in gene-like elements organized in a characteristic inverted repeat. When transcribed, microRNA genes give rise to stem-looped precursor RNAs from which the microRNAs are subsequently processed. MicroRNAs are typically about 21 nucleotides in length. The released miRNAs are incorporated into RISC-like complexes containing a particular subset of Argonaute proteins that exert sequence-specific gene repression (see, for example, Millar and Waterhouse, 2005; Pasquinelli et al., 2005; Almeida and Allshire, 2005).

Cosuppression

Another molecular biological approach that may be used is co-suppression. The mechanism of co-suppression is not well understood but is thought to involve post-transcriptional gene silencing (PTGS) and in that regard may be very similar to many examples of antisense suppression. It involves introducing an extra copy of a gene or a fragment thereof into a plant in the sense orientation with respect to a promoter for its expression. The size of the sense fragment, its correspondence to target gene regions, and its degree of sequence identity to the target gene are as for the antisense sequences described above. In some instances the additional copy of the gene sequence interferes with the expression of the target plant gene. Reference is made to WO 97/20936 and EP 0465572 for methods of implementing co-suppression approaches.

Nucleic Acid Constructs

Nucleic acid constructs useful for producing transgenic plants can readily be produced using standard techniques.

When inserting a region encoding an mRNA the construct may comprise intron sequences. These intron sequences may aid expression of the transgene in the plant. The term "intron" is used in its normal sense as meaning a genetic segment that is transcribed but does not encode protein and which is spliced out of an RNA before translation. Introns may be incorporated in a 5'-UTR or a coding region if the transgene encodes a translated product, or anywhere in the transcribed region if it does not. However, in a preferred embodiment, any polypeptide encoding region is provided as a single open reading frame. As the skilled addressee would be aware, such open reading frames can be obtained by reverse transcribing mRNA encoding the polypeptide.

To ensure appropriate expression of the gene encoding an mRNA of interest, the nucleic acid construct typically comprises one or more regulatory elements such as promoters, enhancers, as well as transcription termination or polyadenylation sequences. Such elements are well known in the art.

The transcriptional initiation region comprising the regulatory element(s) may provide for regulated or constitutive expression in the plant. Preferably, expression at least occurs in cells of the seed.

A number of constitutive promoters that are active in plant cells have been described. Suitable promoters for constitutive expression in plants include, but are not limited to, the cauliflower mosaic virus (CaMV) 35S promoter, the Figwort mosaic virus (FMV) 35S, the sugarcane bacilliform virus promoter, the *commelina* yellow mottle virus promoter, the light-inducible promoter from the small subunit of the ribulose-1,5-bis-phosphate carboxylase, the rice cytosolic triosephosphate isomerase promoter, the adenine phosphoribosyltransferase promoter of *Arabidopsis*, the rice actin I gene promoter, the mannopine synthase and octopine synthase promoters, the Adh promoter, the sucrose synthase promoter, the R gene complex promoter, and the chlorophyll α/β binding protein gene promoter. These promoters have been used to create DNA vectors that have been expressed in plants; see, e.g., WO 84/02913. All of these promoters have been used to create various types of plant-expressible recombinant DNA vectors.

The promoter may be modulated by factors such as temperature, light or stress. Ordinarily, the regulatory elements will be provided 5' of the genetic sequence to be expressed. The construct may also contain other elements that enhance transcription such as the nos 3' or the ocs 3' polyadenylation regions or transcription terminators.

The 5' non-translated leader sequence can be derived from the promoter selected to express the heterologous gene sequence, and can be specifically modified if desired so as to increase translation of mRNA. For a review of optimizing expression of transgenes, see Koziel et al. (1996). The 5' non-translated regions can also be obtained from plant viral RNAs (Tobacco mosaic virus, Tobacco etch virus, Maize dwarf mosaic virus, Alfalfa mosaic virus, among others) from suitable eukaryotic genes, plant genes (wheat and maize chlorophyll a/b binding protein gene leader), or from a synthetic gene sequence. The present invention is not limited to the use of constructs wherein the non-translated region is derived from the 5' non-translated sequence that accompanies the promoter sequence. The leader sequence could also be derived from an unrelated promoter or coding sequence. Leader sequences useful in context of the present invention comprise the maize Hsp70 leader (U.S. Pat. Nos. 5,362,865 and 5,859,347), and the TMV omega element.

The termination of transcription is accomplished by a 3' non-translated DNA sequence operably linked in the chimeric vector to the polynucleotide of interest. The 3' non-translated region of a recombinant DNA molecule contains a polyadenylation signal that functions in plants to cause the addition of adenylate nucleotides to the 3' end of the RNA. The 3' non-translated region can be obtained from various genes that are expressed in plant cells. The nopaline synthase 3' untranslated region, the 3' untranslated region from pea small subunit Rubisco gene, the 3' untranslated region from soybean 7S seed storage protein gene are commonly used in this capacity. The 3' transcribed, non-translated regions containing the polyadenylate signal of *Agrobacterium* tumor-inducing (Ti) plasmid genes are also suitable.

Typically, the nucleic acid construct comprises a selectable marker. Selectable markers aid in the identification and screening of plants or cells that have been transformed with the exogenous nucleic acid molecule. The selectable marker gene may provide antibiotic or herbicide resistance to the barley cells, or allow the utilization of substrates such as mannose. The selectable marker preferably confers hygromycin resistance to the barley cells.

Preferably, the nucleic acid construct is stably incorporated into the genome of the plant. Accordingly, the nucleic acid comprises appropriate elements which allow the molecule to be incorporated into the genome, or the construct is placed in an appropriate vector which can be incorporated into a chromosome of a plant cell.

One embodiment of the present invention includes the use of a recombinant vector, which includes at least transgene outlined herein, inserted into any vector capable of delivering the nucleic acid molecule into a host cell. Such a vector contains heterologous nucleic acid sequences, that is nucleic acid sequences that are not naturally found adjacent to nucleic acid molecules of the present invention and that preferably are derived from a species other than the species from which the nucleic acid molecule(s) are derived. The vector can be either RNA or DNA, either prokaryotic or eukaryotic, and typically is a virus or a plasmid.

A number of vectors suitable for stable transfection of plant cells or for the establishment of transgenic plants have been described in, e.g., Pouwels et al., Cloning Vectors: A Laboratory Manual, 1985, supp. 1987; Weissbach and Weissbach, Methods for Plant Molecular Biology, Academic Press, 1989; and Gelvin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

Transgenic Plants

Transgenic barley plants, as defined in the context of the present invention include plants (as well as parts and cells of said plants) and their progeny which have been genetically modified using recombinant techniques to cause production of at least one polynucleotide and/or polypeptide in the desired plant or plant organ. Transgenic plants can be produced using techniques known in the art, such as those generally described in A. Slater et al., Plant Biotechnology—The Genetic Manipulation of Plants, Oxford University Press (2003), and P. Christou and H. Klee, Handbook of Plant Biotechnology, John Wiley and Sons (2004).

In a preferred embodiment, the transgenic plants are homozygous for each and every gene that has been introduced (transgene) rogeny do not segregate for the desired phenotype. The transgenic plants may also be heterozygous for the introduced transgene(s), such as, for example, in F1 progeny which have been grown from hybrid seed. Such plants may provide advantages such as hybrid vigour, well known in the art. Four general methods for direct delivery of a gene into cells have been described: (1) chemical methods (Graham et al., 1973); (2) physical methods such as microinjection (Capecchi, 1980); electroporation (see, for example, WO 87/06614, U.S. Pat. Nos. 5,472,869, 5,384,253, WO 92/09696 and WO 93/21335); and the gene gun (see, for example, U.S. Pat. Nos. 4,945,050 and 5,141,131); (3) viral vectors (Clapp, 1993; Lu et al., 1993; Eglitis et al., 1988); and (4) receptor-mediated mechanisms (Curiel et al., 1992; Wagner et al., 1992).

Acceleration methods that may be used include, for example, microprojectile bombardment and the like. One example of a method for delivering transforming nucleic acid molecules to plant cells is microprojectile bombardment. This method has been reviewed by Yang et al., Particle Bombardment Technology for Gene Transfer, Oxford Press, Oxford, England (1994). Non-biological particles (microprojectiles) that may be coated with nucleic acids and delivered into cells by a propelling force. Exemplary particles include those comprised of tungsten, gold, platinum, and the like. A particular advantage of microprojectile bombardment, in addition to it being an effective means of reproducibly transforming monocots, is that neither the isolation of protoplasts, nor the susceptibility of *Agrobacterium* infection are required. An illustrative embodiment of a method for delivering DNA into *Zea mays* cells by acceleration is a biolistics α-particle delivery system, that can be used to propel particles coated with DNA through a screen, such as a stainless steel or Nytex screen, onto a filter surface covered with corn cells cultured in suspension. A particle delivery system suitable for use with the present invention is the helium acceleration PDS-1000/He gun is available from Bio-Rad Laboratories.

For the bombardment, cells in suspension may be concentrated on filters. Filters containing the cells to be bombarded are positioned at an appropriate distance below the microprojectile stopping plate. If desired, one or more screens are also positioned between the gun and the cells to be bombarded.

Alternatively, immature embryos or other target cells may be arranged on solid culture medium. The cells to be bombarded are positioned at an appropriate distance below the microprojectile stopping plate. If desired, one or more screens are also positioned between the acceleration device and the cells to be bombarded. Through the use of techniques set forth herein one may obtain up to 1000 or more foci of cells transiently expressing a marker gene. The number of cells in a focus that express the exogenous gene product 48 hours post-bombardment often range from one to ten and average one to three.

In bombardment transformation, one may optimize the pre-bombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the flight and velocity of either the macro- or microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmids. It is believed that pre-bombardment manipulations are especially important for successful transformation of immature embryos.

In another alternative embodiment, plastids can be stably transformed. Method disclosed for plastid transformation in higher plants include particle gun delivery of DNA containing a selectable marker and targeting of the DNA to the plastid genome through homologous recombination (U.S. Pat. Nos. 5,451,513, 5,545,818, 5,877,402, 5,932,479, and WO 99/05265).

Accordingly, it is contemplated that one may wish to adjust various aspects of the bombardment parameters in small scale studies to fully optimize the conditions. One may particularly wish to adjust physical parameters such as gap distance, flight distance, tissue distance, and helium pressure. One may also minimize the trauma reduction factors by modifying conditions that influence the physiological state of the recipient cells and that may therefore influence transformation and integration efficiencies. For example, the osmotic state, tissue hydration and the subculture stage or cell cycle of the recipient cells may be adjusted for optimum transformation. The execution of other routine adjustments will be known to those of skill in the art in light of the present disclosure.

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art (see, for example, U.S. Pat. Nos. 5,177,010, 5,104,310, 5,004,863, 5,159,135). Further, the integration of the T-DNA is a relatively precise process resulting in few rearrangements. The region of DNA to be transferred is defined by the border sequences, and intervening DNA is usually inserted into the plant genome.

Modern *Agrobacterium* transformation vectors are capable of replication in *E. coli* as well as *Agrobacterium*, allowing for convenient manipulations as described (Klee et al., In: Plant DNA Infectious Agents, Hohn and Schell, eds., Springer-Verlag, New York, pp. 179-203 (1985). Moreover, technological advances in vectors for *Agrobacterium*-mediated gene transfer have improved the arrangement of genes and restriction sites in the vectors to facilitate construction of vectors capable of expressing various polypeptide coding genes. The vectors described have convenient multi-linker regions flanked by a promoter and a polyadenylation site for direct expression of inserted polypeptide coding genes and are suitable for present purposes. In addition, *Agrobacterium* containing both armed and disarmed Ti genes can be used for the transformations. In those plant varieties where *Agrobacterium*-mediated transformation is efficient, it is the method of choice because of the facile and defined nature of the gene transfer.

A transgenic plant formed using *Agrobacterium* transformation methods typically contains a single genetic locus on one chromosome. Such transgenic plants can be referred to as being hemizygous for the added gene. More preferred is a transgenic plant that is homozygous for the added structural gene; i.e., a transgenic plant that contains two added genes, one gene at the same locus on each chromosome of a chromosome pair. A homozygous transgenic plant can be obtained by sexually mating (selfing) an independent segregant transgenic plant that contains a single added gene, germinating some of the seed produced and analyzing the resulting plants for the gene of interest.

It is also to be understood that two different transgenic plants can also be mated to produce offspring that contain two independently segregating exogenous genes. Selfing of appropriate progeny can produce plants that are homozygous for both exogenous genes. Back-crossing to a parental plant and out-crossing with a non-transgenic plant are also contemplated, as is vegetative propagation. Descriptions of other breeding methods that are commonly used for different traits and crops can be found in Fehr, In: Breeding Methods for Cultivar Development, Wilcox J. ed., American Society of Agronomy, Madison Wis. (1987).

Transformation of plant protoplasts can be achieved using methods based on calcium phosphate precipitation, polyethylene glycol treatment, electroporation, and combinations of these treatments. Application of these systems to different plant varieties depends upon the ability to regenerate that particular plant strain from protoplasts. Illustrative methods for the regeneration of cereals from protoplasts are described (Fujimura et al., 1985; Toriyama et al., 1986; Abdullah et al., 1986).

Other methods of cell transformation can also be used and include but are not limited to introduction of DNA into plants by direct DNA transfer into pollen, by direct injection of DNA into reproductive organs of a plant, or by direct injection of DNA into the cells of immature embryos followed by the rehydration of desiccated embryos.

The regeneration, development, and cultivation of plants from single plant protoplast transformants or from various transformed explants is well known in the art (Weissbach et al., In: Methods for Plant Molecular Biology, Academic Press, San Diego, Calif., (1988). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene is well known in the art. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired exogenous nucleic acid is cultivated using methods well known to one skilled in the art.

Methods for transforming dicots, primarily by use of *Agrobacterium tumefaciens*, and obtaining transgenic plants have been published for cotton (U.S. Pat. Nos. 5,004,863, 5,159,135, 5,518,908); soybean (U.S. Pat. Nos. 5,569,834, 5,416,011); *Brassica* (U.S. Pat. No. 5,463,174); peanut (Cheng et al., 1996); and pea (Grant et al., 1995).

Methods for transformation of cereal plants such as barley for introducing genetic variation into the plant by introduction of an exogenous nucleic acid and for regeneration of plants from protoplasts or immature plant embryos are well known in the art, see for example, CA 2,092,588, AU 61781/94, AU 667939, U.S. Pat. No. 6,100,447, PCT/US97/10621, U.S. Pat. Nos. 5,589,617, 6,541,257, and WO 99/14314. Preferably, transgenic barley plants are produced by *Agrobacterium tumefaciens* mediated transformation procedures. Vectors carrying the desired nucleic acid construct may be introduced into regenerable barley cells of tissue cultured plants or explants, or suitable plant systems such as protoplasts.

The regenerable barley cells are preferably from the scutellum of immature embryos, mature embryos, callus derived from these, or the meristematic tissue.

To confirm the presence of the transgenes in transgenic cells and plants, a polymerase chain reaction (PCR) amplification or Southern blot analysis can be performed using methods known to those skilled in the art. Expression products of the transgenes can be detected in any of a variety of ways, depending upon the nature of the product, and include Western blot and enzyme assay. One particularly useful way to quantitate protein expression and to detect replication in different plant tissues is to use a reporter gene, such as GUS. Once transgenic plants have been obtained, they may be grown to produce plant tissues or parts having the desired phenotype. The plant tissue or plant parts, may be harvested, and/or the seed collected. The seed may serve as a source for growing additional plants with tissues or parts having the desired characteristics.

Production of Mutant Plants

There are many techniques known in the art which can be used to produce barley with reduced levels of hordeins by mutating endogenous hordeins genes, including, but not limited to, TILLING, zinc finger nuclease, TAL effector nuclease (TALEN), and Clustered Regularly Interspaced Short Palindromic Repeats (CRSPR).

Tilling

Plants of the invention can be produced using the process known as TILLING (Targeting Induced Local Lesions IN Genomes). In a first step, introduced mutations such as novel single base pair changes are induced in a population of plants by treating seeds (or pollen) with a chemical mutagen, and then advancing plants to a generation where mutations will be stably inherited. DNA is extracted, and seeds are stored from all members of the population to create a resource that can be accessed repeatedly over time.

For a TILLING assay, PCR primers are designed to specifically amplify a single gene target of interest. Specificity is especially important if a target is a member of a gene family or part of a polyploid genome. Next, dye-labeled primers can be used to amplify PCR products from pooled DNA of multiple individuals. These PCR products are denatured and reannealed to allow the formation of mismatched base pairs. Mismatches, or heteroduplexes, represent both naturally occurring single nucleotide polymorphisms (SNPs) (i.e., several plants from the population are likely to carry the same polymorphism) and induced SNPs (i.e., only rare individual plants are likely to display the mutation). After heteroduplex formation, the use of an endonuclease, such as Cel I, that recognizes and cleaves mismatched DNA is the key to discovering novel SNPs within a TILLING population.

Using this approach, many thousands of plants can be screened to identify any individual with a single base change as well as small insertions or deletions (1-30 bp) in any gene or specific region of the genome. Genomic fragments being assayed can range in size anywhere from 0.3 to 1.6 kb. At 8-fold pooling, 1.4 kb fragments (discounting the ends of fragments where SNP detection is problematic due to noise) and 96 lanes per assay, this combination allows up to a million base pairs of genomic DNA to be screened per single assay, making TILLING a high-throughput technique.

TILLING is further described in Slade and Knauf (2005) and Henikoff et al., (2004).

In addition to allowing efficient detection of mutations, high-throughput TILLING technology is ideal for the detection of natural polymorphisms. Therefore, interrogating an unknown homologous DNA by heteroduplexing to a known sequence reveals the number and position of polymorphic sites. Both nucleotide changes and small insertions and deletions are identified, including at least some repeat number polymorphisms. This has been called Ecotilling (Comai et al., 2004).

Each SNP is recorded by its approximate position within a few nucleotides. Thus, each haplotype can be archived based on its mobility. Sequence data can be obtained with a relatively small incremental effort using aliquots of the same amplified DNA that is used for the mismatch-cleavage assay. The left or right sequencing primer for a single reaction is chosen by its proximity to the polymorphism. Sequencher software performs a multiple alignment and discovers the base change, which in each case confirmed the gel band.

Ecotilling can be performed more cheaply than full sequencing, the method currently used for most SNP discovery. Plates containing arrayed ecotypic DNA can be screened rather than pools of DNA from mutagenized plants. Because detection is on gels with nearly base pair resolution and background patterns are uniform across lanes, bands that are of identical size can be matched, thus discovering and genotyping SNPs in a single step. In this way, ultimate sequencing of the SNP is simple and efficient, made more so by the fact that the aliquots of the same PCR products used for screening can be subjected to DNA sequencing.

Genome Editing Using Site-Specific Nucleases

Genome editing uses engineered nucleases composed of sequence specific DNA binding domains fused to a non-specific DNA cleavage module. These chimeric nucleases enable efficient and precise genetic modifications by inducing targeted DNA double stranded breaks that stimulate the cell's endogenous cellular DNA repair mechanisms to repair the induced break. Such mechanisms include, for example, error prone non-homologous end joining (NHEJ) and homology directed repair (HDR).

In the presence of donor plasmid with extended homology arms, HDR can lead to the introduction of single or multiple transgenes to correct or replace existing genes.

In the absence of donor plasmid, NHEJ-mediated repair yields small insertion or deletion mutations of the target that cause gene disruption.

Engineered nucleases useful in the methods of the present invention include zinc finger nucleases (ZFNs) and transcription activator-like (TAL) effector nucleases (TALEN).

Typically nuclease encoded genes are delivered into cells by plasmid DNA, viral vectors or in vitro transcribed mRNA. The use of fluorescent surrogate reporter vectors also allows for enrichment of ZFN- and TALEN-modified cells. As an alternative to ZFN gene-delivery systems, cells can be contacted with purified ZFN proteins which are capable of crossing cell membranes and inducing endogenous gene disruption.

Complex genomes often contain multiple copies of sequences that are identical or highly homologous to the intended DNA target, potentially leading to off-target activity and cellular toxicity. To address this, structure (Miller et al., 2007; Szczepek et al., 2007) and selection based (Doyon et al., 2011; Guo et al., 2010) approaches can be used to generate improved ZFN and TALEN heterodimers with optimized cleavage specificity and reduced toxicity.

A zinc finger nuclease (ZFN) comprises a DNA-binding domain and a DNA-cleavage domain, wherein the DNA binding domain is comprised of at least one zinc finger and is operatively linked to a DNA-cleavage domain. The zinc finger DNA-binding domain is at the N-terminus of the protein and the DNA-cleavage domain is located at the C-terminus of said protein.

A ZFN must have at least one zinc finger. In a preferred embodiment, a ZFN would have at least three zinc fingers in order to have sufficient specificity to be useful for targeted genetic recombination in a host cell or organism. Typically, a ZFN having more than three zinc fingers would have progressively greater specificity with each additional zinc finger.

The zinc finger domain can be derived from any class or type of zinc finger. In a particular embodiment, the zinc finger domain comprises the $Cis_2His_2$ type of zinc finger that is very generally represented, for example, by the zinc finger transcription factors TFIIIA or Sp1. In a preferred embodiment, the zinc finger domain comprises three $Cis_2His_2$ type zinc fingers. The DNA recognition and/or the binding specificity of a ZFN can be altered in order to accomplish targeted genetic recombination at any chosen site in cellular DNA. Such modification can be accomplished using known molecular biology and/or chemical synthesis techniques. (see, for example, Bibikova et al., 2002).

The ZFN DNA-cleavage domain is derived from a class of non-specific DNA cleavage domains, for example the DNA-cleavage domain of a Type II restriction enzyme such as FokI (Kim et al., 1996). Other useful endonucleases may include, for example, HhaI, HindIII, Nod, BbvCI, EcoRI, BglI, and AlwI.

A linker, if present, between the cleavage and recognition domains of the ZFN comprises a sequence of amino acid residues selected so that the resulting linker is flexible. Or, for maximum target site specificity, linkerless constructs are made. A linkerless construct has a strong preference for binding to and then cleaving between recognition sites that are 6 bp apart. However, with linker lengths of between 0 and 18 amino acids in length, ZFN-mediated cleavage occurs between recognition sites that are between 5 and 35 bp apart. For a given linker length, there will be a limit to the distance between recognition sites that is consistent with both binding and dimerization. (Bibikova et al., 2001). In a preferred embodiment, there is no linker between the cleavage and recognition domains, and the target locus comprises two nine nucleotide recognition sites in inverted orientation with respect to one another, separated by a six nucleotide spacer.

In order to target genetic recombination or mutation according to a preferred embodiment of the present invention, two 9 bp zinc finger DNA recognition sequences must be identified in the host DNA. These recognition sites will be in an inverted orientation with respect to one another and separated by about 6 bp of DNA. ZFNs are then generated by designing and producing zinc finger combinations that bind DNA specifically at the target locus, and then linking the zinc fingers to a DNA cleavage domain.

ZFN activity can be improved through the use of transient hypothermic culture conditions to increase nuclease expression levels (Doyon et al., 2010) and co-delivery of site-specific nucleases with DNA end-processing enzymes (Certo et al., 2012). The specificity of ZFN-mediated genome editing can be improved by use of zinc finger nickases (ZFNickases) which stimulate HDR without activation the error-prone NHE-J repair pathway (Kim et al., 2012; Wang et al., 2012; Ramirez et al., 2012; McConnell Smith et al., 2009).

A transcription activator-like (TAL) effector nuclease (TALEN) comprises a TAL effector DNA binding domain and an endonuclease domain.

TAL effectors are proteins of plant pathogenic bacteria that are injected by the pathogen into the plant cell, where they travel to the nucleus and function as transcription factors to turn on specific plant genes. The primary amino acid sequence of a TAL effector dictates the nucleotide sequence to which it binds. Thus, target sites can be predicted for TAL effectors, and TAL effectors can be engineered and generated for the purpose of binding to particular nucleotide sequences.

Fused to the TAL effector-encoding nucleic acid sequences are sequences encoding a nuclease or a portion of a nuclease, typically a nonspecific cleavage domain from a type II restriction endonuclease such as FokI (Kim et al., 1996). Other useful endonucleases may include, for example, HhaI, HindIII, Nod, BbvCI, EcoRI, BglI, and AlwI. The fact that some endonucleases (e.g., FokI) only function as dimers can be capitalized upon to enhance the target specificity of the TAL effector. For example, in some cases each FokI monomer can be fused to a TAL effector sequence that recognizes a different DNA target sequence, and only when the two recognition sites are in close proximity do the inactive monomers come together to create a functional enzyme. By requiring DNA binding to activate the nuclease, a highly site-specific restriction enzyme can be created.

A sequence-specific TALEN can recognize a particular sequence within a preselected target nucleotide sequence present in a cell. Thus, in some embodiments, a target nucleotide sequence can be scanned for nuclease recognition sites, and a particular nuclease can be selected based on the target sequence. In other cases, a TALEN can be engineered to target a particular cellular sequence.

Genome Editing Using Programmable RNA-Guided DNA Endonucleases

Distinct from the site-specific nucleases described above, the clustered regulatory interspaced short palindromic repeats (CRISPR)/Cas system provides an alternative to ZFNs and TALENs for inducing targeted genetic alterations. In bacteria, the CRISPR system provides acquired immunity against invading foreign DNA via RNA-guided DNA cleavage.

CRISPR systems rely on CRISPR RNA (crRNA) and transactivating chimeric RNA (tracrRNA) for sequence-specific silencing of invading foreign DNA. Three types of CRISPR/Cas systems exist: in type II systems, Cas9 serves as an RNA-guided DNA endonuclease that cleaves DNA upon crRNA-tracrRNA target recognition. CRISPR RNA base pairs with tracrRNA to form a two-RNA structure that guides the Cas9 endonuclease to complementary DNA sites for cleavage.

The CRISPR system can be portable to plant cells by co-delivery of plasmids expressing the Cas endonuclease and the necessary crRNA components. The Cas endonuclease may be converted into a nickase to provide additional control over the mechanism of DNA repair (Cong et al., 2013).

CRISPR loci are a distinct class of interspersed short sequence repeats (SSRs) that were first recognized in *E. coli* (Ishino et al., 1987; Nakata et al., 1989). Similar interspersed SSRs have been identified in *Haloferax mediterranei, Streptococcus pyogenes, Anabaena,* and *Mycobacterium tuberculosis* (Groenen et al., 1993; Hoe et al., 1999; Masepohl et al., 1996; Mojica et al., 1995).

The CRISPR loci differ from other SSRs by the structure of the repeats, which have been termed short regularly spaced repeats (SRSRs) (Janssen et al., 2002; Mojica et al., 2000). The repeats are short elements that occur in clusters, that are always regularly spaced by unique intervening sequences with a constant length (Mojica et al., 2000). Although the repeat sequences are highly conserved between strains, the number of interspersed repeats and the sequences of the spacer regions differ from strain to strain (van Embden et al., 2000).

The common structural characteristics of CRISPR loci are described in Jansen et al., (2002) as (i) the presence of multiple short direct repeats, which show no or very little sequence variation within a given locus; (ii) the presence of non-repetitive spacer sequences between the repeats of similar size; (iii) the presence of a common leader sequence of a few hundred basepairs in most species harbouring multiple CRISPR loci; (iv) the absence of long open reading frames within the locus; and (v) the presence of one or more cas genes.

CRISPRs are typically short partially palindromic sequences of 24-40 bp containing inner and terminal inverted repeats of up to 11 bp. Although isolated elements have been detected, they are generally arranged in clusters (up to about 20 or more per genome) of repeated units spaced by unique intervening 20-58 bp sequences. CRISPRs are generally homogenous within a given genome with most of them being identical. However, there are examples of heterogeneity in, for example, the Archaea (Mojica et al., 2000).

As used herein, the term "cas gene" refers to one or more cas genes that are generally coupled associated or close to or in the vicinity of flanking CRISPR loci. A comprehensive review of the Cas protein family is presented in Haft et al. (2005). The number of cas genes at a given CRISPR locus can vary between species.

EXAMPLES

Example 1. Materials and Methods

Plant Material

Barley line cv Sloop (wild-type) was obtained from the Australian Winter Cereals Collection (Tamworth, Australia). Risø 56 (expressing no B-hordeins) and Risø 1508 (expressing no C-hordeins and decreased D- and B-hordeins) (Doll, 1973; Doll, 1983) were obtained from the Nordic Germplasm Bank (Alnarp, Sweden). Risø 1508 was an ethyleneimine induced mutant carrying a mutation in the lys3a gene on chromosome 5H which reduced accumulation of C-hordeins. Each of these lines are publically available. Plants were grown in glasshouse conditions at 25° C. days and 20° C. nights and harvested seeds inspected to exclude contamination. For malting and brewing experiments, plants of cultivars Sloop, Risø 56 and Risø 1508 were grown side by side at CSIRO Ginninderra Experimental Station, Canberra, in the field, and 10 kg grain of each harvested. The grains were malted and 20 L batches of beer brewed using standard techniques.

Prolamin Extraction from Flour

To extract prolamins (alcohol-soluble proteins), grain was milled to wholemeal flour using standard techniques. Prolamins in aqueous washed wholemeal flour (10 g) were dissolved in 55% (v/v) propan-2-ol (HPLC grade), 2% (w/v) dithiothreitol (DTT) by incubation at 65° C. for 45 min, and precipitated with two volumes of propan-2-ol at −20° C. overnight. The precipitated prolamins were dissolved in 8 M urea, 1% DTT, 25 mM triethanolamine-HCl (pH 6), and purified by fast protein liquid chromatography (FPLC) on a 4 mL Resource RPC column (GE Healthcare, Sydney, NSW, Australia) eluted with a 30 mL linear gradient (at 2 mL/min) from 3% to 60% acetonitrile in 1% (v/v) trifluoroacetic acid (TFA).

Filter-Aided Sample Preparation (FASP) Method

Fifty µL of hordein extract was transferred to a PALL Nanosep 10 MWCO filter. 200 µL of 8 M urea (Sigma) in 0.1 M Tris/HCl pH 8.5 (UA) was added and the mixture centrifuged at 14000 rpm for 15 min at about 20° C. The flow-through from the tube was discarded. A further 200 µl of UA was added to the filter unit and re-centrifuged at 14,000 rpm for 15 min. 100 µIAA solution (0.05 M iodoacetamide in UA) was added and the sample mixed at 600 rpm in a thermo-mixer set at 20° C. for 1 min and then incubated without mixing for 20 min. 100 µl of UA was added to the filter unit and centrifuged at 14,000×g for 15 min. This step was repeated twice. 100 µl of 0.05M NH$_4$HCO$_3$ (ammonium bicarbonate, ABC) in water was added to the filter unit and centrifuged at 14,000×g for 10 min. This step was repeated twice. 40 µl ABC with 15 µL of trypsin stock (1.5 µg/µl, Sigma) was added and each sample mixed at 600 rpm in a thermo-mixer for 1 min. The filter units were incubated in a wet chamber at 37° C. for 4-18 h for enzyme digestion. The filter units were transferred to new collection tubes and centrifuged at 14,000 rpm, for 10 min. 40 μl ABC was added and the filter units centrifuged again at 14,000 rpm for 10 min. This step was repeated once. The flow through fraction was acidified by adding 15 μL of 5% formic acid and lyophilised. The extracted, dried peptides were resuspended in 30 μL 0.5% formic acid for analysis by MRM.

Preparation of Wort and Beer

Barley was malted in a Joe White Micromalting System in several 800 g tins.

The steeping regime involved: 8 h soaking, 9 h rest, 5 h soaking at 17° C. (Sloop); 8 h soaking, 10 h rest, 5 h soaking at 17° C. (Risø 56); and 7 h soaking, 8 h rest, 3 h soaking at 17° C. (Risø 1508). Germination occurred over 94 h at 16° C. for Sloop and 15° C. for the two hordein deletion mutants. The kiln program was over 21 h between 50-80° C. The kilned malt was mashed as detailed in Colgrave et al. (2012). After the indicated amylase rest time, the mash was bought to the boil and boiled for 1 h to produce the wort. During boiling, the boiling wort was bittered with Tettnang hops to achieve 21-22 IBUs. The wort was cooled overnight to 20° C. and then fermented with Fermentis US-05 yeast at 18-20° C. to completion after about 2 weeks. The unfiltered beer was kegged, and force carbonated before bottling.

Analysis of Beer

A selection of 60 commercial beers were obtained as listed in Supplementary Table 1 of Colgrave et al. (2012). Triplicate samples (1 mL) were taken from two different bottles of each and degassed to remove $CO_2$ under reduced pressure. Aliquots (100 μL) of degassed beer were taken and were reduced by addition of 20 μL of 50 mM DTT under $N_2$ for 30 min at 60° C. To these solutions, 20 μL of 100 mM iodoacetamide (IAM) was added and the samples were incubated for 15 min at room temperature. To each solution 5 μL of 1 mg/mL trypsin (Sigma) or chymotrypsin (Sigma) was added and the samples incubated at 37° C. overnight. The digested peptide solution was acidified by addition of 10 μL of 5% formic acid and passed through a 10 kDa MW filter (Pall, Australia). The filtrate was lyophilized and reconstituted in 1% formic acid and stored at 4° C. until analysis.

Analysis of Undigested Wort and Beer

Wort and beer (0.1 mL) derived from the wild-type (Sloop) barley and hordein deletion mutants were passed through a 10 kDa molecular weight cut-off filter (Pall) by centrifugation at 14,000 rpm for 30 min to produce a peptide fraction amenable to LC-MS/MS. The peptide fraction (10 μL) was analysed on the QStar Elite mass spectrometer.

Q-TOF MS

Samples were chromatographically separated on a Shimadzu nano HPLC system (Shimadzu Scientific, Rydalmere, Australia) using a Vydac MS C18 300 Å, column (150 mm×0.3 mm) with a particle size of 5 μm (Grace Davison, Deerfield, USA) using a linear gradient of 2-42% solvent B over 20 min at a flow rate of 3 μL/min. The mobile phases consisted of solvent A (0.1% formic acid) and solvent B (0.1% formic acid/90% acetonitrile/10% water). A QStar Elite QqTOF mass spectrometer (Applied Biosystems) was used in standard MS/MS data-dependent acquisition mode with a nano-electrospray ionization source. Survey MS spectra were collected (m/z 400-1800) for 1 s followed by three MS/MS measurements on the most intense parent ions (10 counts/second threshold, 2+ to 5+ charge state, and m/z 100-1600 mass range for MS/MS), using the manufacturer's 'Smart Exit'. Parent ions previously targeted were excluded from repetitive MS/MS acquisition for 30 seconds (mass tolerance of 100 mDa).

Linear Ion Trap (Triple Quadrupole) MS

Reduced and alkylated tryptic peptides were analyzed on an Applied Biosystems 4000 QTRAP mass spectrometer (Applied Biosystems, Framingham, Mass., USA) equipped with a TurboV ionization source operated in positive ion mode. Samples were chromatographically separated on a Shimadzu Nexera UHPLC (Shimadzu) using a Phenomenex Kinetex C18 (2.1 mm×10 cm) column with a linear gradient of 5-45% acetonitrile (ACN) over 15 min with a flow rate of 400 μL/min. The eluent from the HPLC was directly coupled to the mass spectrometer. Data were acquired and processed using Analyst 1.5 Software™. Information Dependent Acquisition (IDA) analyses were performed using an enhanced MS (EMS) scan over the mass range 350-1500 as the survey scan and triggered the acquisition of tandem mass spectra. The top two ions of charge state 2-5 that exceeded a defined threshold value (100,000 counts) were selected and first subjected to an enhanced resolution (ER) scan prior to acquiring an enhanced product scan (EPI) over the mass range 125-1600.

Analysis of Mass Spectra and Database Searching

ProteinPilot™ 4.0 software (Applied Biosystems) with the Paragon Algorithm was used for the identification of proteins. Tandem mass spectrometry data was searched against in silico tryptic or chymotryptic digests of Triticeae proteins of the Uniprot (version 2011/05) and NCBI (version 2011/05) databases. All search parameters were defined as iodoacetamide modified with cysteine alkylation, with either trypsin or chymotrypsin as the digestion enzyme. Modifications were set to the "generic workup" and "biological" modification sets provided with this software package, which consisted of 126 possible modifications, for example, acetylation, methylation and phosphorylation. The generic workup modifications set contains 51 potential modifications that may occur as a result of sample handling, for example, oxidation, dehydration and deamidation. Peptides with one missed cleavage were included in the analysis.

Construction and Application of a Custom-Built Cereal Database

A non-redundant custom cereal seed storage protein database was constructed by including all reported protein sequences from nucleotide entries in NCBI, TIGR Gene Indices, or TIGR Plant Transcript Assemblies belonging to *Triticum, Hordeum, Avena, Secale* and *Triticosecale* species. The nucleotide sequences, for the above species, were translated in six frames, trimmed to keep only the longest open reading frame. The resulting protein sequence set was then made non-redundant. Only sequences with 100% match from start to finish were collapsed together, to maintain all variations. Lastly, these files were filtered to retain only entries containing the words gluten, gliadin, glutenin, hordein, avenin or secalin. Tandem mass spectrometry data was searched against the custom cereal database.

Protein Alignment and Identification of Prototypic Peptides

All known hordein proteins in the Uniprot database and predicted hordein proteins in the TIGR database were aligned. Within each family (B, C, D or γ), peptides that were common were selected as representative of the family. MRM transitions were determined for each peptide where the precursor ion (Q1) m/z was based on the size and expected charge and the fragment ion (Q3) m/z values were predicted using known fragmentation patterns and/or the data collected in the characterization workflows. Up to six transitions were used in the preliminary analyses and the MRM transitions were refined and the top two MRM transitions were selected per peptide for use in the final method, wherein the most intense MRM transition was used as a quantifier and the second most intense transition was used as a qualifier.

MRM Mass Spectrometry

MRM experiments were used for quantification of the hordein-derived tryptic peptides. For both IDA- and MRM-triggered MS/MS experiments, the scan speed was set to 1000 Da/s and peptides were fragmented in the collision cell with nitrogen gas using rolling collision energy dependent on the size and charge of the precursor ion. Quantification of hordein peptides was achieved using scheduled MRM scanning experiments using a 120 s detection window for each MRM transition and a s cycle time. The first quadrupole was used to select the mass-to-charge ratio (m/z) of the analyte, the so-called precursor ion. The precursor ion was then transmitted to the collision cell (the second quadrupole). Collision-induced dissociation (CID) occurs resulting in the production of fragment ions that were transmitted to the third quadrupole. A second stage of mass selection occurs specifically targeting the m/z values of the known fragment ions. The two stages of mass selection are known as Q1 and Q3 referring to the quadrupole in which they occur. The Q1 to Q3 transition is thus known as the MRM transition and is highly specific and selective for the analyte of choice.

Relative Quantification of Hordeins

The relative quantification of each hordein was performed by integrating the peak area of the most intense MRM transition for each peptide. The average peak area was determined by taking the mean of two replicate injections (on different days) from bottles A and B (representing the biological replicates). The results are presented as the percentage of each hordein protein relative to the average hordein content of all gluten-containing beers.

Example 2. Characterization of Hordeins in Barley Flour

Hordeins extracted from barley flour (wild-type cv Sloop) by solubilisation into an alcohol solution were purified by FPLC as described in Example 1. The purified hordein fractions were reduced, alkylated and subjected to either trypsin or chymotrypsin digestion. Following enzymatic digestion, the sub-10 kDa fraction was analyzed by LC-MS/MS to identify the hordeins present in the purified prolamin fraction from flour to provide the complete suite of hordein proteins that might be expected to be found in beer brewed from this flour. Using a 1% false discovery rate (FDR), a total of 144 proteins were identified after trypsin digestion and a total of 55 proteins were identified after chymotrypsin digestion.

Table 1 lists the hordein protein products detected from flour following tryptic digestion. Among the most abundant proteins detected were the previously reported B3-hordein (Accession No. P06471, Kristoffersen et al., 2000), γ-3-hordein (P80198, Fasoli et al., 2010) and the predicted γ-1-hordein (P17990, Cameron-Mills et al., 1988). Likewise, D-hordein (Uniprot: Q84LE9, Gu et al., 2003) was detected in abundance. Other proteins of lesser abundance were detected including two γ-hordeins and a B1-hordein that were not present in either the NCBI or Uniprot databases (Table 1). These proteins were identified by searching a custom-built database comprising translated cereal proteins from nucleotide entries in NCBI, TIGR Gene Indices, or TIGR Plant Transcript Assemblies. Several peptides matching to predicted γ-gliadins and glutenins (from wheat) and avenin-like protein-A (from wheat and goat-grass) were detected. The avenin-like A proteins were reported to be present in beer (Picariello et al., 2011) based on the detection of a 15 amino acid peptide (QQCCQPLAQISEQAR, SEQ ID NO: 5) resulting from tryptic digestion of a 16-17 kDa protein band isolated by SDS-PAGE. The peptide sequence matched a sequence in a single protein from barley as determined by BLASTp searching, along with an additional 13 amino acid (aa) peptide matching to the same predicted protein sequence (Uniprot: F2EGD5). An 11 aa (MVLQTLPSMCR, SEQ ID NO: 6) peptide mapping to an avenin-like A protein (Uniprot: Q2A782) from *Aegilops cylindrica* (jointed goatgrass) was also detected. A subsequent search of the translated EST database (TIGR) revealed a *H. vulgare* protein that explained the 11 aa peptide. Based on the homology between the predicted avenin-like protein-A and γ-hordein proteins, these were included in subsequent analyses.

Single peptide identifications hinted at the presence of C-hordeins within the hordein fraction, however, sequence alignment of known C-hordein proteins revealed an absence of tryptic cleavage sites within these glutamine-rich proteins. Consequently, chymotryptic digest of the hordein fraction yielded identification of C-hordeins with up to 80% sequence coverage (Table 2), highlighting the need for an alternative digestion strategy to characterize this class of hordeins.

TABLE 1

Prolamin proteins identified in FPLC purified fraction of barley flour after trypsin digestion.

| Uniprot Accession | NCBI Accession | TIGR Accession | Name | Score | Coverage | Peptides |
|---|---|---|---|---|---|---|
| — | — | BE454297 | B3-hordein *** | 57.03 | 87.1 | 52 |
| P80198 | 1708280 | TA29416_4513 | γ-hordein-3 | 38.40 | 54.0 | 32 |
| Q84LE9 | 75147012 | TA30219_4513 | D-hordein ** | 34.70 | 55.6 | 41 |
| P17990 | 123464 | — | γ-hordein-1 | 27.70 | 74.7 | 23 |
| — | — | TA30139_4513 | γ-hordein *** | 18.95 | 45.5 | 24 |
| Q40026 | 75220903 | TA29493_4513 | B1-hordein ** | 8.58 | 46.6 | 19 |
| Q4G3S1 | 122220129 | — | B3-hordein * | 5.55 | 15.7 | 10 |
| P06472 | 123460 | — | C-hordein * | 4.56 | 23.9 | 4 |
| C7FB16 | 255348358 | — | B-hordein ** | 4.00 | 22.4 | 22 |
| Q2A782 | 122238432 | — | Avenin-like A * | 4.00 | 14.4 | 2 |
| F2XAR6 | 327365751 | — | γ-gliadin ** | 3.89 | 9.5 | 3 |
| — | — | TA29452_4513 | B1-hordein *** | 3.87 | 52.2 | 18 |
| P17991 | 123461 | — | C-hordein * | 3.87 | 95.8 | 3 |
| — | — | AJ433315 | γ-hordein *** | 3.53 | 99.1 | 19 |

TABLE 1-continued

Prolamin proteins identified in FPLC purified fraction of barley flour after trypsin digestion.

| Uniprot Accession | NCBI Accession | TIGR Accession | Name | Score | Coverage | Peptides |
|---|---|---|---|---|---|---|
| P06471 | 123459 | HVB3HORD | B3-hordein | 2.00 | 73.1 | 42 |
| B9VSH7 | 222538169 | — | D-hordein (similar to HMW glutenin) ** | 2.00 | 16.1 | 9 |
| Q3YAF9 | 122217636 | — | B-hordein ** | 2.00 | 21.7 | 8 |
| B5A818 | — | — | B-hordein (similar to LMW glutenin) ** | 2.00 | 27.2 | 7 |
| D4HNB5 | — | — | B-hordein (similar to LMW glutenin) ** | 2.00 | 13.2 | 4 |
| Q8S3W0 | 75159492 | — | D-hordein (similar to HMW glutenin) ** | 2.00 | 5.0 | 6 |
| F2EGD5 | 326501830 | — | Avenin-like A * | 2.00 | 16.2 | 2 |

Accession numbers for each protein are listed:
* indicates protein identification supporting annotated transcript evidence (Uniprot);
** indicates protein identification supporting genome-derived predicted protein (Uniprot);
*** indicates novel protein identified in database search against unannotated TIGR ESTs.

TABLE 2

Prolamin proteins identified in FPLC purified fraction of barley flour after chymotrypsin digestion.

| Uniprot Accession | NCBI Accession | TIGR Accession | Name | Score | Coverage | Peptides |
|---|---|---|---|---|---|---|
| P06471 | 123459 | HVB3HORD | B3-hordein | 85.95 | 86.4 | 51 |
| Q84LE9 | 75147012 | TA30219_4513 | D-hordein ** | 54.28 | 36.2 | 28 |
| Q41210 | 75102504 | — | C-hordein ** | 50.10 | 88.7 | 44 |
| P80198 | 1708280 | TA29416_4513 | γ-hordein-3 | 36.38 | 69.9 | 19 |
| Q40053 | 19001 | — | C-hordein (Hor1-17) ** | 28.93 | 83.9 | 41 |
| — | — | TA30139_4153 | γ-hordein *** | 21.31 | 59.2 | 11 |
| P06470 | 123458 | — | B1-hordein | 10.13 | 25.1 | 14 |
| Q0PIV6 | 110832715 | — | B-hordein ** | 10.00 | 62.4 | 22 |
| P17990 | 123464 | — | γ-hordein-1 * | 8.00 | 50.9 | 7 |
| P17992 | 123462 | — | C-hordein * | 6.02 | 65.1 | 7 |
| Q571R2 | 75271341 | — | C-hordein (similar to σ-gliadin) * | 4.00 | 61.3 | 3 |
| — | — | TA29452_4513 | B1-hordein *** | 2.13 | 59.4 | 14 |
| C7FB16 | 255348358 | — | B-hordein ** | 2.02 | 61.9 | 15 |
| — | — | TA28105_4153 | Similar to C-hordein *** | 2.01 | 53.4 | 1 |
| — | — | BG416634_F0 | B3-hordein *** | 2.00 | 81.5 | 32 |
| — | — | BI950745_F1 | B3-hordein *** | 2.00 | 33.6 | 15 |
| — | — | TA29459_4513 | B-hordein (similar to GBSS Wx-TmA) *** | 2.00 | 60.9 | 12 |
| Q5PU42 | 56126405 | — | B-hordein (similar to LMW glutenin) ** | 2.00 | 22.6 | 6 |
| Q4G3S5 | 57118089 | — | B3-hordein * | 2.00 | 24.0 | 6 |

Accession numbers for each protein are listed:
* indicates protein identification supporting annotated transcript evidence (Uniprot);
** indicates protein identification supporting genome-derived predicted protein (Uniprot);
*** indicates novel protein identified in database search against unannotated TIGR ESTs.

Example 3. Characterization of Hordeins in Wort and Beer

Analysis of wort, the liquid extracted from the mashing process during brewing, and beer were then conducted and a similar suite of prolamins were identified (Table 3). A total of 27 proteins were identified in wort and 79 in beer, with the most abundant proteins being non-specific lipid transfer protein 1 (LTP1) and the α-amylase trypsin inhibitors (CMd, CMb, CMa). The gluten proteins identified in wort included the avenin-like A protein (18 peptides), γ-hordein-3 (10 peptides) and D-hordein (4 peptides) that were previously observed in the enriched hordein fraction. It was interesting to note, however, that >50% of the peptides were semi-tryptic (cleaved at one end at a site other than Lys/Arg), suggesting that significant degradation of the proteins had occurred during the brewing process. The avenin-like A protein (GenBank Accession No. BE195337) identified from the EST database search was detected with >60% sequence coverage (12 peptides) increasing the confidence of this protein identification.

C-hordein proteins were noticeably absent in beer, but to ensure this was not a false positive owing to the low number of tryptic sites, a chymotryptic digest was performed which affirmed the absence of C-hordeins in beer (Table 3). The absence of C-hordeins was presumably related to their insolubility in water. C-hordeins consist of multiple octa-peptide repeats with a consensus sequence of PQQPFPQQ (SEQ ID NO: 7) rendering them highly insoluble. Many of the C-hordein degradation products are identified in wort but did not survive the brewing and filtration steps leading to the production of beer.

In order to characterize peptide fragments, the wort and beer were passed through a 10 kDa molecular weight cut-off filter and analyzed without enzymatic digestion. 1D-PAGE analysis revealed that the filtration step was efficient in removing proteins from beer. MS analysis revealed the presence of several truncated or degraded hordein products. Table 4 lists the peptide fragments identified. In addition to hordein peptides, peptides derived from a large number of barley proteins including serpin-Z4, non-specific lipid transfer protein 1, α-amylase, β-amylase, hordoindoles (B1, B2) and GAPDH were identified in wort and beer (listed Table 4 and Supplementary Table 2 of Colgrave et al., 2012). Of interest, was the large number of C-hordein fragments observed in wort with only trace levels of C-hordein peptides detected in beer.

The characterization of beer in the absence of enzymatic digestion clearly demonstrates that in addition to intact hordeins, a large number of partially degraded hordein fragments are present and these may also contribute to coeliac toxicity. Many of these peptide fragments contained runs of Gln and Pro that may elicit an immunological response in coeliacs. Examples of potential immunogenic peptides detected are FVQPQQQPFPLQPHQP (avenin-like A; GenBank: TA31086, SEQ ID NO: 8), YPEQP QQPFPWQQPT (γ-1-hordein; P17990, SEQ ID NO: 9), LERPQQLFPQWQPLPQQPP (γ-3-hordein; P80198, SEQ ID NO: 10) and LIIPQQPQQPFPLQPHQP (C-hordein; P17991, SEQ ID NO: 11), where the underlined sequence bears high homology with immunogenic peptides reported previously (Tye-Din et al., 2010; Kahlenberg et al., 2006).

TABLE 3

Prolamin proteins identified in wort and beer.

| Uniprot Accession | NCBI Accession | TIGR Accession | Name | Score | Coverage | Peptides |
|---|---|---|---|---|---|---|
| Prolamins identified in wort (trypsin digestion) | | | | | | |
| F2EGD5 | 326501830 | — | Avenin-like A * | 29.33 | 41.6 | 18 |
| P80198 | 1708280 | TA29416_4513 | γ-hordein-3 | 18.05 | 33.2 | 10 |
| — | — | BE195337 | Avenin-like A *** | 14.00 | 47.0 | 9 |
| Q84LE9 | 75147012 | TA30219_4513 | D-hordein ** | 8.08 | 8.9 | 4 |
| Prolamins identified in beer (trypsin digestion) | | | | | | |
| P80198 | 1708280 | TA29416_4513 | γ-hordein-3 | 55.62 | 53.6 | 33 |
| Q84LE9 | 75147012 | TA30219_4513 | D-hordein ** | 30.16 | 22.2 | 23 |
| P06471 | 18914 | HVB3HORD | B3-hordein | 17.81 | 24.6 | 9 |
| P17990 | 123464 | — | γ-hordein-1 * | 16.98 | 31.9 | 9 |
| — | — | BE195337 | Avenin-like A *** | 15.66 | 64.6 | 12 |
| F2EGD5 | 326501830 | — | Avenin-like A * | 8.06 | 35.3 | 8 |
| Q4G3S5 | 57118089 | — | B3-hordein * | 5.48 | 12.6 | 6 |
| Q40026 | 75220903 | TA29493_4513 | B1-hordein ** | 2.01 | 8.6 | 7 |
| Q94IL5 | 75250230 | — | D-hordein (similar to HMW glutenin) ** | 2.00 | 4.6 | 8 |
| Prolamins identified in beer (chymotryptic digestion) | | | | | | |
| P80198 | 1708280 | TA29416_4513 | γ-hordein-3 | 19.75 | 56.1 | 12 |
| Q40022 | 829269 | — | B1-hordein * | 13.80 | 51.4 | 9 |
| Q84LE9 | 75147012 | TA30219_4513 | D-hordein ** | 12.00 | 26.0 | 6 |
| P17990 | 123464 | — | γ-hordein-1 * | 5.59 | 22.5 | 3 |
| F5A7G6 | — | — | B-hordein (similar to LMW glutenin) ** | 2.00 | 23.2 | 5 |
| Q6EEZ0 | — | — | γ-hordein-3 ** | 2.00 | 25.8 | 2 |

Accession numbers for each protein are listed:
* indicates protein identification supporting annotated transcript evidence (Uniprot);
** indicates protein identification supporting genome-derived predicted protein (Uniprot);
*** indicates novel protein identified in database search against unannotated TIGR ESTs.

TABLE 4

Peptides derived from hordein proteins detected in the sub-10 kDa fraction of beer. Epitopes in bold show high sequence homology with the gluten epitopes recognised by the Mendez R4 MAb raised against rye prolamins (QQPFP (SEQ ID NO: 12), QQQFP (SEQ ID NO: 13), LQPFP (SEQ ID NO: 14), QLPFP (SEQ ID NO: 15))[a]. These peptides may elicit an immune response in CD patients.

| Name[b] | Conf | Peptide | m/z | Mass | Δm (ppm) |
|---|---|---|---|---|---|
| D-hordein (Q84LE9**) | 99 | RVVDQQLVGQLPWSTG (SEQ ID NO: 16) | 891.99 | 1781.97 | 13.41 |
| | 99 | VVDQQLVGQLPWSTGL (SEQ ID NO: 17) | 870.45 | 1738.89 | 19.72 |

TABLE 4-continued

Peptides derived from hordein proteins detected in the sub-10 kDa fraction of beer. Epitopes in bold show high sequence homology with the gluten epitopes recognised by the Mendez R4 MAb raised against rye prolamins (QQPFP (SEQ ID NO: 12), QQQFP (SEQ ID NO: 13), LQPFP (SEQ ID NO: 14), QLPFP (SEQ ID NO: 15))[a]. These peptides may elicit an immune response in CD patients.

| Name[b] | Conf | Peptide | m/z | Mass | Δm (ppm) |
|---|---|---|---|---|---|
| | 99 | VVDQQLVGQLPWSTG (SEQ ID NO: 18) | 813.93 | 1625.85 | 5.17 |
| | 99 | VVDQQLVGQLPW (SEQ ID NO: 19) | 691.38 | 1380.74 | 2.46 |
| | 99 | QLVGQLPWSTGL (SEQ ID NO: 20) | 649.85 | 1297.68 | 16.25 |
| | 99 | QLVGQLPWSTG (SEQ ID NO: 21) | 593.30 | 1184.59 | 22.03 |
| | 99 | LVGQLPWSTGLQM (SEQ ID NO: 22) | 715.37 | 1428.73 | 12.46 |
| | 99 | LVGQLPWSTGL (SEQ ID NO: 23) | 585.83 | 1169.65 | 5.55 |
| | 99 | LVGQLPWSTG (SEQ ID NO: 24) | 529.28 | 1056.54 | 14.86 |
| | 99 | VGQLPWSTGLQM (SEQ ID NO: 25) | 658.83 | 1315.64 | 14.06 |
| | 99 | VGQLPWSTGL (SEQ ID NO: 26) | 529.28 | 1056.54 | 16.75 |
| | 99 | (p)QLAAQLPAMCRLEGS[HexNAc] (SEQ ID NO: 27) | 887.41 | 1772.80 | 22.05 |
| | 99 | VVRQYEQQTEVPSKGGSFYPGGTAPP (SEQ ID NO: 28) | 927.12 | 2778.35 | 5.79 |
| γ-3-hordein (P80198) | 99 | FVLPQQQAQFKVVGS (SEQ ID NO: 29) | 838.46 | 1674.90 | 4.24 |
| | 99 | FVLPQQQAQF (SEQ ID NO: 30) | 603.31 | 1204.61 | 12.54 |
| | 99 | AIVMQQQVQQQVGHGF (SEQ ID NO: 31) | 899.43 | 1796.85 | 26.60 |
| | 99 | LERPQQLFPQWQPLPQQPP (SEQ ID NO: 32) | 776.41 | 2326.19 | 12.21 |
| | 99 | LFPQWQPLPQQPP (SEQ ID NO: 33) | 788.41 | 1574.82 | 6.03 |
| | 99 | LQQLGQGMPIQL (SEQ ID NO: 34) | 663.85 | 1325.69 | 16.98 |
| | 95 | VVGSLVIQT (SEQ ID NO: 35) | 458.27 | 914.53 | 9.84 |
| γ-3-hordein (P179999*) | 99 | LQQPQHQFPQPTQQFPQRPn (SEQ ID NO: 36) | 777.39 | 2329.15 | 8.16 |
| | 99 | YPEQPQQFFPWQQPT (SEQ ID NO: 37) | 935.93 | 1869.84 | 16.15 |
| | 99 | GVVQPQQLAQME (SEQ ID NO: 38) | 664.31 | 1326.61 | 41.08 |
| | 99 | [p]QPQHQFPQPTQQFPQRP (SEQ ID NO: 39) | 691.33 | 2070.98 | 9.90 |
| Avenin-like A (BE195337*) | 99 | FVQPQQQVP**VEITR (SEQ ID NO: 40) | 834.94 | 1667.87 | 19.61 |
| | 99 | FVQPQQQVPVEI (SEQ ID NO: 41) | 706.37 | 1410.72 | 18.78 |

TABLE 4-continued

Peptides derived from hordein proteins detected in the sub-10 kDa fraction of beer. Epitopes in bold show high sequence homology with the gluten epitopes recognised by the Mendez R4 MAb raised against rye prolamins (QQPFP (SEQ ID NO: 12), QQQFP (SEQ ID NO: 13), LQPFP (SEQ ID NO: 14), QLPFP (SEQ ID NO: 15))[a]. These peptides may elicit an immune response in CD patients.

| Name[b] | Conf | Peptide | m/z | Mass | Δm (ppm) |
|---|---|---|---|---|---|
| C-hordein (P17991*) | 98.2 | LIIPQQPQQPFPLQPHQP (SEQ ID NO: 42) | 1053.59 | 2105.17 | 14.82 |
|  | 99 | IIPQQPQQPFPLQPHQP (SEQ ID NO: 43) | 997.05 | 1992.08 | 13.40 |
| B3-hordein (P06471) | 98.4 | VQVQIPFVHPSI (SEQ ID NO: 44) | 682.38 | 1362.74 | 16.22 |
| Avenin-like A (F2EGD5*) | 99 | SFGQPQQQVPVEVMR (SEQ ID NO: 45) | 865.43 | 1728.84 | 13.0 |
| C-hordein (Q40053*) | 95.8 | IIPQQPFPLQPQPFPQQPQQPLPQPQQP (SEQ ID NO: 46) | 1081.25 | 3240.73 | 11.08 |
| C-hordein (TA28105*) | 96.4 | IPLQPQ[Dea]QPFP**QQPP (SEQ ID NO: 47) | 808.40 | 1614.79 | 30.53 |

[a]Kahlenberg et al. (2006).
[b]Accession numbers for each protein are listed: * indicates protein identification supporting annotated transcript evidence (Uniprot);  indicates protein identification supporting genome-derived predicted protein (Uniprot); * indicates novel protein identified in database search against unannotated TIGR ESTs.

Example 4. Relative Quantitation of Hordeins in Beer by MRM Mass Spectrometry The proteomic characterization of purified hordeins and beer in Examples 2 and 3 enabled the elucidation of the major hordein proteins present in barley. Multiple reaction monitoring (MRM) was identified as a useful tool for the quantitation of peptides and proteins. In this method, following tryptic digestion of the proteins, proteolytic fragments were chromatographically separated by HPLC and analysed by MRM mass spectrometry. The first quadrupole (Q1) selected the first peptide m/z value (precursor mass) and transmited this ion to the collision cell (Q2). Collision-induced dissociation resulted in the production of fragment ion series relating to the amino-acid sequence of the proteolytic fragments. Diagnostic fragment ions were then selected in the third quadrupole (Q3) and transmitted to the detector allowing quantitation of the peptides of interest. Typically three MRM transitions per peptide were used and at least two peptides per protein.

From each of the protein families, a single isoform was selected to monitor the gluten content of beers brewed from selectively-bred barley lines (see below). Multiple tryptic peptides (≥2 peptides/protein) were selected for development of a quantitative assay. Where these peptides had previously been detected in the discovery experiments, the peptide m/z and fragment ion information was used to determine the MRM transition to be used. A number of peptides that were not initially identified were included in the MRM assay so that a minimum of two peptides per protein were used. In these instances, the retention times were not known and the MRM transitions could not be scheduled in the first pass experiments. The peptide retention times were determined and subsequent experiments used scheduled MRM transitions.

Beer derived from a single elite Australian malting barley ("Sloop") was used for the development and refinement of the MRM method as it contained the full complement of hordein proteins, whereas the barley variants (Risø 56 and Risø 1508) were expected to be low in, or devoid of, B- and C-hordeins. When beers brewed from samples of wild-type and two hordein mutant barley grains (Risø 56 and Risø 1508) were analysed using MRM analysis, the eight selected peptides (three MRM transitions per peptide) were all clearly observed for wild-type barley beer. The Risø 56 beer showed an approximate three-fold decrease in the amount of the D-hordein peptides and the B-hordein peptides were noticeably absent. The Risø 1508 beer showed a further decrease in the amount of each peptide measured, but a trace amount of avenin-like A protein was observed.

The reproducibility of the analytical method was assessed by examining the single cultivar barley beer ("Sloop"). Firstly, the beer was subjected to multiple freeze-thaw cycles (either 1, 10, 20 or 50 cycles) and no significant change (co-efficient of variation, CV, of <15%) was observed in the peak area for each of the monitored MRM transitions even after 50 cycles. Secondly, the digestion efficiency was examined by six replicate digestions yielding a CV of <15%. The analytical reproducibility was assessed by performing four replicate injections of each digest with a CV of <15%. Finally, the variation in hordein content between two different bottles of beer was assessed and found to be <10%.

Analysis of Commercial Beers

Further validation of the MRM method of quantifying hordeins in beer was provided by analyzing the gluten content of a selection of 60 commercial beers, including labeled low gluten and gluten-free beers. Duplicate samples from separate bottles were treated by reduction, alkylation and digestion (Example 1) and were analyzed by MRM mass spectrometry. FIG. 2 shows the relative quantitation of the avenin-like A proteins (A), B-hordeins (B, C), D-hordeins (D) and γ-hordeins (E) in the commercial beers relative to Sloop. Relative to the average values for the non-gluten-free beers, the commercial beers were observed to vary in the type (hordein families present) and the amount (between 1-380% cf. average for any given hordein protein). Eight of the beers (Nos. 17, 47, 49, 50, 51, 52, 58 and 60) were labeled as gluten-free as they were brewed from sorghum malt, teff, rice, millet or maize. These cereals lack the gluten proteins present in barley and wheat. The MRM assay confirmed that they were devoid of the hordein proteins and hordein-related protein (avenin-like A) targeted.

Beers 17 and 50-52 were sorghum-based, beer 47 did not specify what it is made from, beer 49 was millet-based, beer 58 was brewed from sorghum malt, teff and rice and beer 60 was a non-cereal derived beer. In the examination of two beers (57 and 59) that have been classified as low-gluten (<10 ppm), the relative hordein content was not dissimilar to the average hordein content across the range of beers tested. Beer 57 showed low avenin-like A protein levels (~50% cf. average), but surprisingly showed significant levels of peptides derived from the B1- (>300% cf. average), D- (~105%) and γ3-hordeins (~62%). Beer 59, showed low, but significant levels of B1-, D- and γ-hordeins (55%, 42% and 92% respectively) and equivalent levels of the avenin-like A protein to those observed in the gluten-containing beers.

Conclusions

Beers made from barley contained gluten derived from the grain used in the brewing process. The gluten level in beer may be measured using ELISA, however, there are many limitations associated with accurate measurement of hordeins using current ELISA technology. In the Examples above, a mass spectrometric assay was developed to characterize the complete suite of hordeins in purified hordein preparations, wort and beer and to perform relative quantitation of the most abundant hordein proteins. The assay using mass spectrometry was robust and sensitive for the measurement of hordein (gluten) in flour, wort and beer and could readily be applied to malt.

Example 5. Identification of a Null Mutation in the Hor3 Gene of Barley

The barley D-hordein polypeptide of 105 kDa is encoded by the Hor3 gene on the long arm of chromosome 1H (Gu et al., 2003). A wild-race of barley designated Ethiopian R118 was identified as not accumulating D-hordeins (Brennan et al., 1998) and was obtained from a publicly available germplasm collection at The John Innes Centre Public Collections (Accession No. 3771). This line was a wild race of barley, highly unsuited for commercial production of grain.

Grains of Ethiopia R118 were sown in the greenhouse. The resultant plants were observed to be segregating for the 2-row and 6-row phenotypes and for black, pigmented seeds and green seeds. A two-row line which produced green seeds was selected and crossed to cv Sloop. F2 half-seeds that were negative for production of D-hordein were selected. Plants of this line were back-crossed to the wild-type Sloop and an F2 plant which was null for D-hordein was again selected. This plant was backcrossed to Sloop and a progeny plant backcrossed again to produce a BC2 line which was negative for D-hordein production in a genetic background which had about 87.5% of the genome of Sloop.

The gene encoding D-hordein was amplified from genomic DNA isolated from each of the Sloop BC2, D-hordein negative plants derived from Ethiopia R118 and the wild-type Sloop. This was by PCR with standard conditions and generated a series of 3 overlapping fragments. The primer pairs used in the amplifications were:

```
Fragment 1
                                        (SEQ ID NO: 60)
   5' Dhor1         GACACATATTCTGCCAAAACCCC
   and
                                        (SEQ ID NO: 61)
   3' Dhor3         ACGAGGGCGACGATTACCGC Fragment 2
                                        (SEQ ID NO: 62)
   5' Dhor1b        GAGATCAATTCATTGACAGTCCACC,
   and
                                        (SEQ ID NO: 63)
   3' Dhor1         CTTGTCCTGACTGCTGCGGAGAAA Fragment 3
                                        (SEQ ID NO: 64)
   5'Dhor2          GCAACAAGGACACTACCCAAGTATG,
   and
                                        (SEQ ID NO: 65)
   3' Dhor2         GCTGACAATGAGCTGAGACATGTAG
```

The amplification products were purified and the nucleotide sequence of each was determined. The assembled sequence from Sloop was 2838 bp long (SEQ ID NO: 72) and the sequence derived from Ethiopia R118 was 2724 bp long (SEQ ID NO: 73). The predicted ATG translation start codon for both proteins was at position 398-400 of the respective sequences. For Sloop, the termination codon was at nucleotide position 2641-2643, encoding a protein of 747 amino acid residues. Analysis of the sequence from Ethiopia R118 revealed that when compared to Sloop there was a C to G change at position 848 (position 450 relative to the start codon) that introduced an in-frame TAG stop codon into the Hor3 gene that resulted in truncation of the polypeptide at position 150 in the protein (FIG. 3). This truncated the D-hordein polypeptide before the proline and glutamine rich domain that contains epitopes identified as immunogenic to coeliacs.

This nucleotide substitution abolished a KpnI site that was present in the wild-type nucleotide sequence in cultivar Sloop and allowed the development of a co-dominant CAPS marker. For this purpose, a DNA fragment of 272 bp was amplified using the primers 5' Dhor-marker (GGCAATAC-GAGCAGCAAAC, SEQ ID NO: 66) and 3' Dhor-marker (CCTCTGTCCTGGTTGTTGTC, SEQ ID NO: 67) (FIG. 4). The amplification products were then incubated with the restriction enzyme KpnI and electrophoresed on agarose gels. The fragment from wild-type barley Sloop was digested by KpnI to produce two fragments of 164 bp and 108 bp. In contrast, the 272 bp fragment from the D-null Ethiopia R118 was not digested. Therefore, this method clearly distinguished the wild-type and null alleles for the gene encoding D-hordein.

Example 6. Identification of a Molecular Marker for a Deletion Mutation at the Hor2 Locus of Barley The Hor2 locus on the short arm of chromosome 1H in barley comprises a family of about 20-30 genes, each encoding a B-hordein in the size range of about 36-kDa (Anderson et al., 2013). Riso 56 is a gamma-ray induced mutation which has a deletion of about 86 kb including all or nearly all of the B-hordein genes (Kreis et al., 1983). This mutation was used to generate a Hor2-lys3a double mutation as described previously by Tanner et al. (2010), expressing greatly reduced levels of total hordeins.

A molecular marker was designed and tested to detect the wild-type Hor2 locus and distinguish it from the Hor2-deleted locus, as follows using standard PCR conditions. The absence of a B1-hordein PCR band of 800 bp was diagnostic of the absence (deletion) of the Hor2 locus i.e. the presence of the mutant allele at Hor2. The primer pairs used in the amplifications were:

```
                                      (SEQ ID NO: 68)
    3' B1 Hor       TCGCAGGATCCTGTACAACG (SEQ ID NO: 69)
    5'B1 Hor        CAACAATGAAGACCTTCCTC
```

A control PCR reaction which produced a characteristic PCR band at 450 bp was also carried out on each DNA sample, indicating the presence of the gamma-hordein locus and ensured the quality of the sample DNA was sufficient for the Hor2 reaction, using primer pairs:

```
                                      (SEQ ID NO: 70)
    5' gamma Hor 3   CGAGAAGGTACCATTACTCCAG (SEQ ID NO: 71)
    3' gamma 3 full  AGTAACAATGAAGGTCCATCG
```

Example 7. Generation of a Triple Null Barley Mutant

F5 plants of the Hor2-lys3a double mutant barley line identified as G1* in WO2009/021285 were grown in the glasshouse to produce F6 progeny. F6 plants were then grown in the field to produce F7 progeny. To combine the Hor2-lys3a mutations with the Hor3 null mutation, plants of the F7 generation were crossed with the D-hordein negative BC$_2$ plants derived from Ethiopia R118 (Example 5) and the F1 progeny selfed to produce F2 seeds. F2 seeds were cut in half and the germ-half germinated and the seedlings screened by B- and D-hordein PCR as in Examples 5 and 6 and for gamma-hordein. The remaining half of each seed comprising the endosperm was ground in a solution containing 8M urea, 1% DTT and the extracted proteins separated by SDS-PAGE. The absence of characteristic protein bands at approximately 50 kDa indicating the absence of the C-hor proteins. Three hordein triple-nulls, designated T1, T2, and T3 were identified from about 300 F2 seeds. The expected frequency for the combination of three recessive mutations, each in the homozygous state, by Mendelian genetics was 1/64, presuming that the Hor2 (B-hordeins) and Hor3 (D-hordeins) loci are separated far enough on chromosome 1H to recombine readily.

The three plants which were homozygous for each of the three mutations (Hor2-lys3a-Hor2) designated T1, T2 and T3 were maintained and propagated through up to three generations of single-seed descent, selecting the 12 heaviest seeds in each generation. Average seed weights of F3 seeds from these lines were: T1, 38.2 mg; T2, 37.0 mg; T3, 39 mg. Seed yield per line (grams of seed per 20 heads) and plant heights were measured. Plants which produced poorly filled heads were discarded. Two F4 lines were selected: T2-4-8 and T2-6-A5 and further trialed in the field. Of these, T2-4-8 was selected as having slightly better grain yield and designated as barley ULG3.0.

An important phenotype for barley grain, related to grain size and shape and an indicator of grain yield, is the percentage of grains which do not pass through sieves with a mesh size of 2.8, 2.5, 2.2 and 2.0 mm, in particular the 2.8 mm sieve. Smaller grain makes the processing and malting less efficient relative to wild-type barley. This phenotype is referred to as "2.8 mm screenings" and is indicated as the percentage of grains that do not pass through the particular sieve. For wild-type cultivars such as Sloop, the 2.8 mm screening parameter is typically 95-98%. For hordein-deficient lines such as the Hor2-lys3a double mutant (ULG2.0), the 2.8 mm screening parameter was generally about 53%. Sometimes, depending on the growth conditions e.g. drought, it was less than 10% and the majority of grains could pass through the 2.5 mm sieve. For ULG3.0, the 2.8 mm screening parameter was about 54%. Average weights (mg) of field grown grains were: Sloop, 53.6+/−0.9, ULG2.0, 33.5+/−0.4; ULG3.0, 39.1+/−0.3. ULG3.0 therefore provided 69% of the grain yield compared to ULG2.0 at 50% relative to the wild-type Sloop (100%). ULG3.0 therefore represented a substantial improvement in grain yield compared to the ULG2.0 line. However, the 2.8 mm screening parameter remained a problem for barley ULG3.0.

Example 8. Generation of a Further Triple Null Barley Mutants with Increased Yield Although the ULG3.0 barley line produced increased grain yield compared to ULG2.0, it was still desirable to increase that further. Therefore, plants of ULG3.0 were crossed with plants of wild-type cultivars Sloop, Baudin and Yagan, and with plants of hordein triple null lines identified containing 50% of each parent germplasm. These hordein triple-null lines were intercrossed, and also crossed to wild-type cultivars Hindmarsh and Commander. Progeny comprising all three null mutations were backcrossed twice to plants of Sloop, Baudin, Hindmarsh and Commander and more homozygous lines produced by single-seed descent. One resultant line of the many that were produced was selected and designated as barley ULG3.1.

From the intercrosses with the Sloop, Yagan and Baudin plants, a second round of intercrosses was performed to combine the genetic backgrounds of all three parent cultivars starting with plants which each comprised the triple null mutations. From the intercrossed F1 plants, all of the progeny were expected to comprise all three mutations. About 1000 F2 seed per pedigree were planted in rows in the field, and F2 plants selected which were relatively shorter and produced F3 seed that were larger, with well-filled heads. Both early and late maturing plants were selected. In a following generation grown in the field, lines were selected which additionally exhibited relatively high grain amylase, relatively high harvest index and head length, optimal height (semi-dwarf), lack of lodging and disease resistance to powdery mildew. From the 1500 families, about 20 of the best were selected. Data for the 20 best lines is provided in Table 5. Individual seed weights (kernel weight) were improved beyond that of ULG 3.0 of 41.8 mg/seed with the highest seed weight of 48.4 mg/seed being observed for line P12072-2. This improvement in seed size was accompanied by increased harvest index, a measure of efficiency of seed formation, above 40% with the highest harvest index of 46.5% being measured in line P12124-1. Most importantly, the percentage 2.8 mm screenings also improved from 53.5% for ULG3.0 to over 80% with a high of 97.3% for line P12140-1.

One selected line was fixed by a single-seed generation to produce plants that were homozygous for the three null alleles at Hor2-lys3a-Hor3 and designated ULG3.2. The 2.8 mm screening parameter for ULG3.2 was in the range of 80-93% in several replications when grown in the field compared to about 97% for Sloop, 85% for Hindmarsh, 96% for wild-type cultivar Oxford, and 98% for Maratime.

Average seed weights and thicknesses were: ULG2.0, 33.4 mg, 2.4 mm; ULG3.0, 41.8 mg, 2.5 mm; ULG3.2, 47.2 mg, 2.8 mm.

TABLE 5

Second selection of ULG 3.2 lines June 2012.

| Plant ID No | Mean tiller | Mean head | Harvest index (%) | No of Tillers | Kernel weight | % 2.8 mm Screening |
|---|---|---|---|---|---|---|
| P12072-2 | 84.7 | 8.3 | 39.0% | 9 | 48.4 | 88.3 |
| P12132-1 | 83.0 | 8.2 | 43.9% | 5 | 47.5 | 92.7 |
| P12048-1 | 75.0 | 7.0 | 39.4% | 8 | 47.2 | 86.7 |
| P12122-2 | 74.3 | 6.7 | 35.0% | 5 | 47.2 | 96.5 |
| P12049-1 | 70.0 | 6.3 | 38.7% | 12 | 46.5 | 93.6 |
| P12125-1 | 78.0 | 7.7 | 42.0% | 10 | 46.2 | 95.3 |
| P12140-1 | 105.7 | 9.0 | 32.4% | 15 | 45.9 | 97.3 |
| P12055-2 | 57.0 | 5.8 | 36.3% | 5 | 45.7 | 91.9 |
| P12088-2 | 72.7 | 6.3 | 42.6% | 8 | 45.4 | 90.7 |
| P12125-2 | 71.7 | 5.3 | 45.3% | 8 | 45.0 | 95.0 |
| P12043-2 | 86.7 | 9.0 | 29.5% | 12 | 44.7 | 85.4 |
| P12050-1 | 64.3 | 6.0 | 36.5% | 4 | 44.4 | 93.6 |
| P12148-1 | 93.3 | 7.3 | 35.0% | 14 | 44.2 | 90.0 |
| P12149-1 | 103.3 | 8.0 | 34.7% | 15 | 44.0 | 91.2 |
| P12124-1 | 79.3 | 7.3 | 46.5% | 8 | 43.7 | 96.8 |
| P12152-2 | 98.3 | 9.0 | 34.8% | 9 | 43.5 | 91.5 |
| P12049-3 | 76.3 | 6.3 | 40.0% | 7 | 43.2 | 92.4 |
| P12100-2 | 79.3 | 6.3 | 46.5% | 15 | 43.2 | 88.3 |
| P12126-1 | 73.0 | 6.0 | 37.0% | 10 | 43.1 | 98.0 |
| P12122-1 | 64.7 | 6.0 | 45.4% | 5 | 42.8 | 90.8 |
| P12048-2 | 65.0 | 5.7 | 41.8% | 4 | 42.5 | 93.9 |
| P12148-2 | 90.3 | 6.3 | 33.3% | 7 | 42.5 | 94.9 |
| P12159-2 | 82.7 | 7.7 | 33.6% | 12 | 42.4 | 83.5 |
| P12139-1 | 113.7 | 8.3 | 33.9% | 8 | 42.2 | 88.1 |
| P12159-1 | 96.3 | 8.8 | 31.9% | 14 | 41.7 | 94.1 |
| P12139-2 | 89.3 | 7.7 | 34.4% | 5 | 41.3 | 96.8 |
| P12064-2 | 82.3 | 7.2 | 40.8% | 11 | 41.2 | 92.4 |
| P12120-2 | 75.0 | 6.8 | 39.6% | 18 | 41.0 | 84.0 |
| Selection criterion |  | >4 < 10 | >35% | 5 > 20 | >40 | >80% |

Example 9. Measurement of Hordein Levels in Triple Null Barley Mutants

Determination of Hordein Content of ULG3.0 Flour by Multiple Reaction Monitoring Mass Spectrometry (MRM MS)

To measure the hordein content accurately, the MRM MS assay was used, as follows. Grains or half-grains were milled to produce flour which, as wholemeal flour, had the same composition as the entire grain. The prolamin polypeptides from 20 mg flour samples were extracted using 200 µL of a solution containing 55% (v/v) isopropanol and 2% (w/v) dithiothreitol (DTT). An aliquot of the extract, equivalent to 5 mg flour, was subjected to buffer exchange into 8M urea in 0.1 M Tris-HCl, pH 8.5, by centrifuging thrice, using a 10 kDa MW cut-off filter unit. The cysteines in the polypeptides were alkylated by addition of 100 µL of 50 mM iodoacetamide and incubation for 1 hr at room temperature. The buffer was exchanged to 100 µL of 50 mM ammonium bicarbonate, pH 8.5, and polypeptides digested with 10 µL (20 µg) of trypsin for 18 hr at 37° C. The peptides were collected by filtration through the 10 kDa filter, dried and reconstituted in 30 µL of 1% (v/v) formic acid. Peptides were separated by liquid chromatography on a Shimadzu Nexera HPLC with Phenomemenex column (Kinetex, 1.7 µm, C18, 100×2.1 mm) with a gradient from 5% B to 40% B over 10 min at a flow rate of 0.4 mL/min. Solvent A was 0.1% (v/v) aqueous formic acid, solvent B was 90% (v/v) acetonitrile containing 0.1% (v/v) formic acid. The HPLC eluate was directly coupled to the mass spectrometer and MRM analysis was performed on a 4000 QTRAP mass spectrometer targeting hordein-derived tryptic peptides. Data was analysed using Analyst v1.5 software and MultiQuant v2.0.2 software using (peak area integration).

FIG. 5 shows the data obtained for selected B-hordeins, C-hordein, D-hordein, gamma-3-hordein (G3) and gamma-1-hordein (G1). FIG. 5 presents the mean peak area for each peptide MRM transition normalized to the level in Sloop (100%), for four replicate injections from each half-grain from control barley (wild-type, cv Sloop), hordein single-null lines: Risø 56, Risø 1508 and the D-null line derived from Ethiopia R118, the hordein double-null line ULG2.0 and the triple-null lines T2-4-8 and T2-6-A5 (circled). One prototypic peptide was chosen to represent each hordein family, namely: for B-hordein, TLPTMCSVNVPLYR (SEQ ID NO: 48); for D-hordein, DVSPECRPVALSQVVR (SEQ ID NO: 49); for C-hordein, LPQKPFPVQQPF (SEQ ID NO: 50); for G3-hordein, QQCCQQLANINEQSR (SEQ ID NO: 50) and for G1-hordein, CTAIDSIVHAIFMQQGR (SEQ ID NO: 51). These peptides appear frequently and at relatively high abundance in wild-type barley, and were chosen on that basis.

It was seen that the triple-null ULG3.0 grain from line T2-4-8 and second triple-null line T2-6-A5 did not have detectable levels of B-, C-, D-, or, most surprisingly, gamma-1-hordein. That is, less than 1% of the level was observed relative to wild-type. In the same way, gamma-2-hordein was not detected in the ULG3.0 grain. There was a relatively low level of gamma-3-hordein (circled), present at a level of about 20% compared to the level of G3 in Sloop. Gamma-3 hordein is a minor hordein; the gamma-3 hordein content of Sloop is much less than 1% of the total hordein content. The single-null and double-null grains did not accumulate the appropriate hordein, e.g. RisØ56 and ULG2.0 did not accumulate B-hordeins as expected, and RisØ1508 and ULG2.0 did not accumulate C-hordeins as expected. The D-null grain exhibited wild-type levels of B- and C-hordeins but did not accumulate D-hordein.

When the analysis was repeated using several different peptide sequences, in particular the D-hordein peptide AQQ-LAAQLPAMCR (SEQ ID NO: 85) which is present in the wild-type D-hordein protein towards the C-terminus, well after the position of the stop codon in the B-hordein mutant, similar results were obtained (FIG. 6). The avenin-like A protein was also absent from the flour.

It was clear that grain obtained from the hordein triple nulls T2-4-8 and T2-6-A5 did not contain detectable levels of B-, C-, D-hordeins and selected gamma-1 (P17990) and gamma-2 hordeins. The observation for the gamma-1 and gamma-2 hordeins was most unexpected to the inventors, as the triple null mutant lines were not known to contain any mutations that would entirely silence the corresponding genes.

The low hordein content of the ULG3.0 grain as determined by MRM was confirmed by a two-dimensional gel electrophoresis method, as follows. Fifty µg of alcohol soluble protein from extracts of flour from each of hordein null lines T2-4-8 and T2-6-A5 as well as control barley cv Risø 56, each spiked with 1 µg of the landmark polypeptide standards BSA, soy trypsin inhibitor and horse myoglobin were stained with 0.006% (w/v) Colloidal Coomassie G250 according to Tanner et al. (2013) and compared to standard proteins of 20, 30, 40, 50, 60, 80, and kDa (M; Benchmark Protein Ladder, Invitrogen). Spots were cut out of the 2D gel and the following proteins from the control Risø 56 were identified by mass spectrometry of tryptic peptides: C-hordein, gamma-2-hordein (γ2), gamma-3-hordein (γ3) and gamma-1-hordein (γ1), The predicted positions of gamma-1-, gamma-2, and gamma-3-hordeins in the gels from the ULG3.0 grain were identified by comparison with the Risø 56 gel. Only gamma-3-hordein was observed in ULG3.0 flour, the other three polypeptides were not detected. The gamma-3 hordein concentration of each spot were measured by three methods: 1) As a percentage of all spot volumes from the 50 μg of protein: ULG3.0 average γ3 content was 13.5±1.6 ppm; 2) Relative to the spot intensity of 1 μg of BSA: ULG3.0 average γ3 content was 10.9±1.3 ppm; 3) Relative to the spot volume (intensity x area) of 1 μg of BSA: ULG3.0 average γ3 content was 3.4±0.41 ppm.

The low hordein content of the ULG3.0 grain as determined by MRM was further confirmed by an ELISA method, as follows. Twenty mg of wholemeal flour samples or the endosperm half of grains were crushed and washed thrice in 0.5 ml of MilliQ water by shaking at 30/sec for 3×30 sec in a 96 well Vibration Mill (Retsch Gmbh, Rheinische) and centrifuged at 14,000 rpm for 5 min. Prolamins in the flours were extracted into an alcoholic solution consisting of 0.5 ml of 50% (v/v) isopropanol/1% (w/v) DTT, for the control lines Sloop, Rise56, Risø1508, and for ULG2.0, the hordein triple-null lines T1, T2, and T3, and the single seed descent progeny from T2-4-8 and T2-6-A5. Protein concentrations were determined according to Bradford (1976) and 40 ng (1900 ng for the triple-null grains) of alcohol soluble protein diluted with a solution containing ELISA systems diluents with a constant excess of 0.2 mM $H_2O_2$ added to quench any DTT remaining from the initial extract. Diluted protein solutions were added to ELISA plate wells (ELISASystems, Windsor, Queensland, AUSTRALIA), washed and developed at 37° C. for 15 minutes according to the manufacturer's instructions. The amount of hordein in the control extracts was calibrated against a standard of 0-50 ng of Sloop total hordein. Hordein content of the triple-nulls was calibrated against a standard of 0-5 ng of ULG2.0 total hordein. The Sloop and ULG2.0 hordeins were prepared as described by Tanner et al. (2010).

By the ELISA method, the total hordein content of double-null flour samples was 2.9% relative to the wild-type cv Sloop, whereas the remaining hordein content of the two selected hordein triple-null lines, T2-4-8 and T2-6-A5 were 3.9 and 1.5 ug/g (parts per million, ppm; Table 6) both significantly below the FSANZ legislated level of 20 ppm for gluten in gluten free food and approximately 15,000 fold lower than in the wild-type cv Sloop grain.

Determination of Hordein Content of ULG3.0 Beer by Multiple Reaction Monitoring Mass Spectrometry (MRM MS)

The hordein content of beer brewed from barley ULG3.0 grain was measured by MRM MS, detecting specific peptide sequences, using the methods as described in Examples 3 and 4 with slight modifications. The data are presented in FIG. 7. The assays showed the lack of avenin-like A protein, B1- and B3-hordeins, D-hordein and reduced levels of gamma-1-hordein and gamma-3-hordein, in that these were not detected above the background noise in the mass spectrometry (FIG. 7). The assays also showed the absence of C-hordein.

TABLE 6

Summary of hordein content of hordein single-, double- and triple-null lines.

| Line | mg Hordein/gm flour | % of Sloop |
|---|---|---|
| Sloop | 56.6 ± 3.3 | 100% |
| Risø56 | 33.3 ± 1.1 | 58.8% |
| Risø1508 | 4.9 ± 0.26 | 8.7% |
| ULG2.0 | 1.67 ± 0.07 | 2.9% |
| T2-4-8 (ULG3.0) | 0.0039 ± 0.0017 | 0.007% |
| T2-6-A5 | 0.0015 ± 0.0004 | 0.0027% |

Determination of Hordein Content of ULG3.1 and ULG3.2 Flours by MRM MS

The hordein content of flour milled from grains of the ULG3.1 line and 10 candidate lines for ULG3.2 was determined by MRM MS as described for the ULG3.0 grain. Half-grains were milled to flour and the prolamin proteins from 20 mg flour (n=4 replicates) were extracted, alkylated, trypsin digested and analysed by MRM MS as described above. The data are plotted in FIG. 8, which show the mean peak area for each peptide (sum of three MRM transitions) from each half-grain of ULG3.1 and lines arising from the double parental intercross lines designated 043-2-148-2. These are plotted in comparison with control barley (wild-type cultivars Sloop, Baudin, Commander and Hindmarsh) and the triple-null line T2-4-8. The peak area is shown for a selected prototypic peptide, representative of each hordein family, Uniprot accession and amino acid sequences as follows:

A-F2EGD5_QQCCQPLAQISEQAR
(SEQ ID NO: 52; from F2EGD5, central to avenin-like A protein)

B1-Q40020_VFLQQQCSPVR
(SEQ ID NO: 53; close to the N-terminus of B1-hordein)

B3-Q4G3S1_VFLQQQCSPVPMPQR
(SEQ ID NO: 54)

C-Q40055_QLNPSHQELQSPQQPFLK
(SEQ ID NO: 55; close to the N-terminus of C-hordein)

D-Q84LE9_ELQESSLEACR
(SEQ ID NO: 56; from Q84LE9, before the stop codon at Y150)

G1-P17990_APFVGVVTGVGGQ
(SEQ ID NO: 57; from P17990, C-terminal peptide),
and

G3-P80198_QQCCQQLANINEQSR
(SEQ ID NO: 58; from P80198, central to γ3-hordein).

The level of D-hordein in the bi-parental intercross grains shown in FIG. 8 was similar to that in grain from ULG2.0 and the hordein triple null lines T2-4-8 and T2-6-A5, near zero, confirming the observation by 2D PAGE that D-hordein was not detected in grains from the T2-4-8 and T2-6-A5 lines. The level of gamma-1-hordein in these bi-parental intercrossed grain was also similar to that in ULG2.0 and the hordein triple null lines T2-4-8 and T2-6-A5. Several ULG3.2 lines had near zero level of the peptide APFVGVVTGVGGQ (SEQ ID NO: 59). Gamma-1-hordein was not detected by 2D PAGE of T2-4-8 and T2-6-A5 lines. The level of gamma-3-hordein in the bi-parental intercross grains was also similar to that in ULG2.0 and the hordein triple null lines except for line 124.1 (ULG3.2) in which it was very low. Gamma-3-hordein was also detected at reduced levels by 2D PAGE of the T2-4-8 and T2-6-A5 lines.

Interestingly, a synergistic effect was seen of the Hor2 and lys3a mutations in reducing the D-hordein content in ULG2.0 even though no Hor3 mutation (D-hordein) was present. In a similar fashion, the presence of all three mutations (Hor2-lys3a-Hor3) had a synergistic effect on reducing accumulation of the gamma-1- and gamma-2-hordeins as defined by the peptides above.

Example 10. Generation of Hull-Less Triple Null Barley Mutants

The barley grains for selections ULG3.0, ULG3.1 and ULG3.2 were all hulled, which is of benefit to the brewing industry as the spent husks form a filtration bed during the final stages of wort filtration (lautering). However, barley grain hulls have large numbers of tiny silica spikes and therefore the hulls need to be removed by pearling before human consumption. An alternative approach is to produce hull-less grains by genetic means. Therefore, plants of ULG3.0 were crossed with a hull-less barley variety designated Barleymax II (WO2011/011833) and a hull-less, hordein B-, C-, D- triple null mutant (Hor2-lys3a-Hor3) plant selected which was wild-type for the SSIIa gene.

Some F6 hordein triple-null hull-less selections (eg A7_1) contained less than 0.1 ppm total hordein in flour after three rounds of single seed descent.

Example 11. Mutagenesis of Barley

To isolate mutants in selected genes in barley, ethylmethanesulfonate (EMS) mutagenesis was carried out as described by Caldwell (2004). Approximately 45,000 (1.5 kg) grain of ULG3.0 were mutagenised as follows: the grain was imbibed in 2.5 L of distilled water for 4 hr at room temperature with aeration. The water was changed every hour for the duration of imbibition. The seeds were then incubated in 2.5 L of freshly prepared 30 mM EMS in 0.1 M phosphate buffer (pH7) for 16 h at room temperature with aeration. The seeds were then washed with 2.5 L of 100 mM sodium thiosulphate for 10 min at room temperature. The washing with thiosulphate was repeated, and the grains then rinsed thoroughly with 2×2 L of distilled water for 30 min at room temperature with aeration. The seeds were air-dried overnight on absorbent filter paper under a flowing air stream, prior to planting in the field the next day. Bulk M2 seeds were harvested, pooled and analysed for mutants. The mutational frequency after such treatment was approximately 1 mutant in a gene of interest per 1000 seeds. The seeds were screened for the loss of expression of the gamma-3 hordein by dot blot on half-grains using a gamma-3 hordein specific monoclonal antibody, and 40 grains which yielded a negative signal were identified from several tens of thousands of M2 grains. The lack of gamma-3 hordein in these grains was confirmed by Western blotting using the monoclonal antibody, and by mass spectrometry for a specific peptide (SEQ ID NO:58). The half-grains comprising the embryo from each negative grain were plated on media to allow for germination. The embryos in most of the half-grains did not germinate but a few did.

Example 12. Production of Beer from Low Hordein Barley

Brewing trials were carried out using malt produced from ULG2.0 grain by standard methods, and compared with the control wild-type barley cv. Gairdner. Gairdner is a high yielding mid to late maturing semi-dwarf 2-row barley variety grown widely throughout the Australian cereal growing regions. It produces good grain size under favourable conditions, producing moderate extract levels, fermentability and diastatic power, and therefore represents an industry "standard" so is ideal for its use as a control in brewing evaluation trials. The malt produced from ULG2.0 had a slightly higher moisture content of 5.7% compared to Gairdner malt (5.0%) and in appearance was significantly different to Gairdner malt, in that the grain appeared dented and shriveled. The Diastatic Power (DP) of the ULG2.0 malt was 54WK, much lower than the DP for Gairdner at 299WK. Malted barley generally has a DP of at least 250 KW. However, the ULG2.0 malt was negative for starch after 20 min mash time and achieved an LG result of 1.7° Plato.

The malt was milled by two passes through a 2-roller mill and achieved satisfactory cracking of the grain. The malt would be best suited for more complex milling in a six roller mill due to its grain morphology. Alternatively, a hammer mill in conjunction with a mash filter could be used, rather than a lauter tun for wort separation. The milled product was mashed by standard methods, at an initial temperature of 65° C. for 20 min, then 74° C. for 5 min, with the addition of extra sparge liquor. Overall, the shriveled morphology of the ULG2.0 malt made it difficult to mill and mash satisfactorily in comparison to regular malt. The mashed products were then lautered, where again the shriveled morphology of ULG2.0 caused difficulties. The lautering bed fell apart with chanelling so the run off needed to be stopped and the lautering bed re-raked. A considerable amount of potential extract was lost during the lautering process due to the inefficient milling, achieving an all in kettle value of 10.96° and 11.12° Plato when the target was to achieve 14° Plato. The pH, EBC colour and beta-glucan levels were acceptable. The milling deficiency also meant there was not an efficient formation of a bed of husks to act as a filter medium, contributing to a lower the expected extract. The clarity of run-off was initially very hazy, due to poor bed formation, although the wort clarity improved to be acceptable by 30 L of runoff.

The resultant wort was fermented with yeast strain *Saccharomyces uvarum* A at 18.5° C. for 120 hr. The fermentation profile was normal, there was no extended lag phase at the start of fermentation, although significant levels of diacetyl remained even after an extended diacetyl rest phase was given after the end of fermentation gravity was reached. Diacetyl rest is where the beer is left at higher fermentation temperatures prior to chilling the beer to 0° C. to allow the yeast to reabsorb and metabolise diacetyl. Generally 24 hr at end of fermentation is required to allow the yeast time to break this product down. This did not occur with both of the ULG2.0 trial brews. Isomerised hop extract was added at 30 mg/L and the liquor clarified with addition of Silica Hydrogel. The finished bright beer had a lower physical stability than the control brew. Initial chill haze was considered high and the forced chill haze results were outside of normal specifications. However, the chill haze did not form particulates.

The finished beer was subjected to sensory analysis by a panel of trained brewers, and despite the difficulties in the milling and lautering processes, the results were surprisingly good given the issues associated with the brewing performance of the malt. DMS (dimethyl sulphide) was the predominate flavour; however this was not seen as objectionable. The presence of DMS is often considered a flavour fault in Australian beer but is generally well accepted in European, particularly German beers. The brewers' comments were that the ULG2.0 beers were not too dissimilar to the control beers and that they were very passable as a beer, and reminiscent of German Beers. There was no overt "grainy" or "cereal" type flavours and no harshness or astringency with the ULG2.0 beer as can be typical of commercial beers marketed as "Gluten free". Overall the flavour profile was acceptable and reasonable.

Beer was made from barley grain of ULG3.0 by the same method as for ULG2.0, and is made from barley grain of ULG3.2. Malting of the ULG3.0 grain was improved relative to the ULG3.0 grain, mainly because the milling step was improved due to the grain being less shriveled. The beer made from ULG3.0 was of a good quality with an acceptable and reasonable flavor. The improved grain morphology (size and shape) of the grain from ULG3.2 provides for easier milling and lautering in the brewing process, providing beer with less than 1 ppm of total hordeins.

Example 13. Production of Food Using ULG Barley

Two small-scale (10 g) breads are baked using the ULG3.0 and ULG3.2 barley lines. Small-scale loaves are baked for test purposes, but the method can be readily scaled up to commercial quantities. One bread is made with 100% ULG barley flour as the flour ingredient, milled as described above, while the second bread is made with a blend of 30% flour and 70% commercial non-gluten flour such as rice flour as the flour ingredient. Flour (13.02 g) and the other ingredients are mixed into a dough, to peak dough development time in a 35-g mixograph. The recipe to be used, based on the 13.02 g of flour in each case is: flour 100%, salt 2%, dry yeast 1.5%, vegetable oil 2%, and improver 1.5%. The water addition level is based on the micro Z-arm water absorption values that are adjusted for the full formula. The moulding and panning are done in two-stage proofing steps at 40° C. and 85% room humidity. Baking is done in a Rotel oven for 14 min at 190° C.

The breads comprise a gluten content of less than 20 ppm and are suitable for human consumption by subjects having CD.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The present application claims priority from AU 2013902140 filed 13 Jun. 2013, and AU 2013902565 filed 11 Jul. 2013, the entire contents of both of which are incorporated herein by reference.

All publications discussed and/or referenced herein are incorporated herein in their entirety.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

REFERENCES

Abdullah et al. (1986) Biotechnology 4:1087.
Almeida and Allshire (2005) TRENDS Cell Biol 15: 251-258. Anderson et al. (2000) Nature Medicine 6:337-342.
Anderson et al. (2013) Genome 56:179-185.
Bibikova et al. (2001) Mol. Cell. Biol. 21: 289-287.
Bibikova et al. (2002) Genetics 161:1169-1175.
Bourque (1995) Plant Sci. 105: 125-149. Brandt et al. (1990) Eur J Biochem 194:499-505.
Brennan et al. (1998) J Cereal Sci. 28:291-299.
Caldwell (2004) The Plant Journal 40:143-150.
Cameron-Mills et al., (1998). Plant Mol Biol 11: 449-461.
Capecchi (1980) Cell 22:479-488. Catassi et al. (1994) Lancet 343:200-203.
Certo et al. (2012) Nat Methods 8:941-943.
Cheng et al. (1996) Plant Cell Rep. 15:653-657.
Clapp (1993) Clin. Perinatol. 20:155-168.
Colgrave et al., (2012) J. Proteome Res. 11: 386-396.
Comai et al. (2004) Plant J 37: 778-786.
Curiel et al. (1992) Hum. Gen. Ther. 3:147-154.
Davies et al. (1993) Cell Biology International Reports 17:195-202.
De Anglis et al. (2007) J Food Protection 70:135-144.
Doll (1983) Barley seed proteins and possibilities for their improvement. In "Seed Proteins: Biochemistry, Genetics, Nutritional Value", Gottschalk W, Muller H P (eds). Martinus Nijhoff, The Hague:207-223.
Doll et al (1973) Barley Genetics Newsletter 3:12-13.
Dostalek et al. (2006). Food Additives and Contaminants 23:1074-1078.
Doyon et al. (2010) Nat. Methods 7:459-460.
Doyon et al. (2011) Nat. Methods 8:74-79.
Eglitis et al. (1988) Biotechniques 6:608-614.
Fasoli et al., (2010). J. Proteome Res. 9: 5262-6269.
Field et al. (1982) Theoretical and Applied Genetics 62:329-336.
Fowell et al. (2006) Qjm-an International Journal of Medicine 99:453-460.
Fujimura et al. (1985) Plant Tissue Culture Letters 2:74.
Graham et al. (1973) Virology 54:536-539.
Grant et al. (1995) Plant Cell Rep. 15:254-258.
Green (2009) Journal of the American Medical Association 302:1225-1226.
Green and Jabri (2006) Annual Review of Medicine 57:207-221.
Groenen et al. (1993) Mol. Microbiol. 10:1057-1065.
Gu et al. (2003) Genome 46:1084-1097.
Guo et al. (2010) J. Mol. Biol. 400:96-107
Haft et al. (2005) Computational Biology 1(6):e60
Haseloff and Gerlach (1988) Nature 334:585-591.
Hausch et al. (2002) Gastroenterology 122:A180.
Henikoff et al. (2004) Plant Physiol 135: 630-636.
Hoe et al. (1999) Emerg. Infect. Dis. 5:254-263.
Ishino et al. (1987) J. Bacteriol. 169:5429-5433.
Janssen et al. (2002) OMICS J. Integ. Biol. 6:23-33.
Jaradat (1991) Theor Appl Genet 83:164-168.
Kahlenberg et al. (2006) European Food Research Technology. 222:78-82.
Kasarda et al. (1984) PNAS 81:4712-4716.
Kikuchi et al., (2003). Theor Appl Genetics 108: 73-78.
Kim et al. (1996) Proc. Natl. Acad. Sci. USA 93:1156-1160
Kim et al. (2012) Genome Res. 22:1327-1333.
Koziel et al. (1996) Plant Mol. Biol. 32:393-405.
Kreis and Shewry (1989) BioEssays 10:201-207.
Kreis et al. (1983) Cell: 34:161-167.
Kristoffersen et al., (2000) Electrophoresis 21: 3693-3700.

Kupper (2005) Gastroenterology 128:S121-127.
Lanzini et al. (2009) Alimentary Pharmacology & Therapeutics 29:1299-1308.
Lee et al. (2007). Journal of Human Nutrition and Dietetics 20:423-430.
Lu et al. (1993) J. Exp. Med. 178:2089-2096.
Marti et al. (2005) J Pharmacol Exp Therapeut 312:19-26.
Masepohl et al. (1996) Biochim. Biophys. Acta 1307:26-30.
McConnell Smith et al. (2009) PNAS 106:5099-5104.
Millar and Waterhouse (2005) Funct Integr Genomics 5:129-135.
Miller et al. (2007) Nat. Biotechnol. 25:778-785.
Mojica et al. (1995) Mol. Microbiol. 17:85-93.
Mojica et al. (2000) Mol. Microbiol. 36:244-246.
Moravcova et al. (2009). Journal of Chromatography a 1216:3629-3636.
Nakata et al. (1989) J. Bacteriol. 171:3553-3556.
Ohlund et al. (2010). Journal of Human Nutrition and Dietetics 23:294-300.
Pasquinelli et al. (2005) Cuff Opin Genet Develop 15: 200-205.
Perriman et al. (1992) Gene 113: 157-163.
Picariello et al. (2011). Food Chemistry 124:1718-1726.
Ramirez et al. (2012) Nucleic Acids Res. 40:5560-5568.
Rubio-Tapia et al. (2010). American Journal of Gastroenterology 105:1412-1420.
Senior (1998) Biotech. Genet. Engin. Revs. 15: 79-119.
Shan et al. (2002). Science 297:2275-2279.
Shewry (1995) Biological Reviews of the Cambridge Philosophical Society 70:375-426.
Shewry and Halford (2002) Journal of Experimental Botany 53:947-958.
Shewry and Tatham (1990) Biochemical Journal 267:1-12.
Shewry, et al., (1999) The prolamins of the Triticeae. In Seed Proteins, Klewer: London, 1999; pp 35-78.
Shippy et al. (1999) Mol. Biotech. 12: 117-129.
Skovbjerg et al. (2005) Diabetologia 48:1416-1417.
Skovbjerg et al., (2004). Biochim. et Biophys. Acta—Mol. Bas. of Dis. 1690:220-230.
Slade and Knauf (2005) Transgenic Res 14: 109-115.
Smith et al. (2000) Nature 407: 319-320.
Stepniak et al. (2006) Am J Physiol-Gastrointest Liver Physiol 291:621-629.
Szczepek et al. (2007) Nat. Biotechnol. 25:786-793.
Tanner et al. (2013) Plos One: 8: e56456.
Tanner et al., (2010). Aliment Pharmacol Ther. 32: 1184-1191.
Tjon et al. (2010) Immunogenetics 62:641-651.
Toriyama et al. (1986) Theor. Appl. Genet. 205:34.
Tye-Din et al. (2010) Science Translational Medicine 2:41-51.
van Embden et al. (2000) J. Bacteriol. 182:2393-2401.
Wagner et al. (1992) Proc. Natl. Acad. Sci. USA 89:6099-6103.
Wang et al. (2012) Genome Res. 22:1316-1326.
Waterhouse et al. (1998) Proc. Natl. Acad. Sci. USA 95: 13959-13964.
Wijngaard and Arendt (2007) Brewer & Distiller International 3: 31-32.
Wild et al. (2010). Alimentary Pharmacology & Therapeutics 32:573-581.

---

The invention claimed is:

1. A method of producing a food or malt-based beverage ingredient, or a food or a malt-based beverage, from barley grain comprising 50 ppm or less hordeins, the method comprising:
   (i) processing barley grain comprising 50 ppm or less hordeins to produce malt, wort, flour or wholemeal, and/or
   (ii) mixing barley grain comprising 50 ppm or less hordeins, or malt, wort, flour or wholemeal produced from said grain, with at least one other food or beverage ingredient,
   wherein:
   a) the barley grain is homozygous for a genetic variation of the Hor2 locus where most or all of the B-hordein encoding genes in the Hor2 locus have been deleted relative to the Hor2 locus of wild-type barley grain, or wherein the malt, wort, flour or wholemeal produced from said grain comprises DNA which comprises the genetic variation of the Hor2 locus where most or all of the B-hordein encoding genes in the Hor2 locus have been deleted relative to the Hor2 locus of wild-type barley grain,
   b) the barley grain is homozygous for a genetic variation at the Hor3 locus of barley which results in the grain lacking D-Hordein, or wherein the malt, wort, flour or wholemeal produced from said grain comprises DNA which comprises the genetic variation at the Hor3 locus of barley which results in the grain lacking D-hordein, and c) the barley grain is homozygous for a genetic variation at the Lys3 locus of barley which results in the grain lacking C-hordeins, or wherein the malt, wort, flour or wholemeal produced from said grain comprises DNA which comprises the genetic variation at the Lys3 locus which results in the grain lacking C-hordeins, thereby producing the food or malt-based beverage ingredient, or food or malt-based beverage.

2. The method of claim 1, wherein the grain, malt, wort, flour or wholemeal comprises 20 ppm or less hordeins.

3. The method of claim 1, wherein the average weight of the grain is at least 35 mg.

4. The method according to claim 1, wherein at least 80% of the grain do not pass through a 2.8 mm sieve.

5. The method according to claim 1, wherein the grain is from a plant which has a harvest index of about 40% to about 60%.

6. The method according to claim 1, wherein the grain has a length to thickness ratio of less than 5.

7. The method according to claim 1, wherein the flour or wholemeal produced from the grain comprises 10 ppm or less hordeins.

8. The method according to claim 1, wherein the grain, or malt, wort, flour or wholemeal produced from said grain lacks:
   i) B-hordeins comprising a sequence of amino acids provided as SEQ ID NO:53, and
   ii) B-hordeins comprising a sequence of amino acids provided as SEQ ID NO:54.

9. The method according to claim 1, wherein the genetic variation at the Hor3 locus of barley which results in the grain lacking D-Hordein is a null allele of the gene encoding D-hordein which comprises a stop codon, splice site mutation, frame-shift mutation, insertion, deletion or encoding a truncated D-hordein, or where most or all of the D-hordein encoding gene has been deleted.

10. The method according to claim 1, wherein the grain, malt, wort, flour or wholemeal comprises 1% or less, of the level of hordeins when compared to grain from a corresponding wild-type barley plant or malt, wort, flour or wholemeal produced in the same manner from grain from a corresponding wild-type barley plant.

11. The method according to claim 1, wherein the coeliac toxicity of flour produced from the grain is less than about 5% of flour produced from grain of a corresponding wild-type barley plant.

12. The method according to claim 1, wherein at least 50% of the grain germinates within 3 days following imbibition.

13. The method according to claim 1, wherein the food ingredient or malt-based beverage ingredient is flour, starch, malt, or wort, or wherein the food is leavened or unleavened breads, pasta, noodles, breakfast cereals, snack foods, cakes, pastries or foods containing flour-based sauces.

14. The method according to claim 1, wherein the malt-based beverage is beer or whiskey.

15. The method according to claim 1, wherein following consumption of the food or drink at least one symptom of coeliac's disease is not developed by a subject with said disease.

16. A barley grain comprising about 50 ppm or less hordeins, or a barley plant which produces grain comprising about 50 ppm or less hordeins, wherein:
   a) the grain is homozygous for a genetic variation of the Hor2 locus where most or all of the B-hordein encoding genes in the Hor2 locus have been deleted relative to the Hor2 locus of wild-type barley grain,
   b) the grain is homozygous for a genetic variation at the Hor3 locus which results in the grain lacking D-hordeins, and
   c) the grain is homozygous for a genetic variationat the Lys3 locus of barley which results in the grain lacking C-hordeins.

17. A method of producing barley grain comprising about 50 ppm or less hordeins, the method comprising;
   a) growing a barley plant of claim 16, and
   b) harvesting the grain of the barley plant.

18. The method of claim 1, wherein the barley grain, or malt, wort, flour or wholemeal produced from said grain, further has a level of less than 2% of a wild-type level of γ-hordeins comprising a sequence of amino acids provided as SEQ ID NO:57, wherein the level of less than 2% is relative to a wild-type barley grain, or malt, wort, flour or wholemeal produced from said grain, of the barley variety Bomi, Sloop, Baudin, Yagan, Hindmarsh, or Commander.

* * * * *